United States Patent [19]

Clark et al.

[11] Patent Number: 5,681,814
[45] Date of Patent: Oct. 28, 1997

[54] FORMULATED IGF-I COMPOSITION

[75] Inventors: Ross G. Clark, Pacifica; Douglas A. Yeung, Fremont; James Q. Oeswein, Moss Beach, all of Calif.

[73] Assignee: Genentech, Inc., South San Francisco, Calif.

[21] Appl. No.: 71,819

[22] Filed: Jun. 4, 1993

Related U.S. Application Data

[60] Continuation-in-part of Ser. No. 806,748, Dec. 13, 1991, abandoned, which is a division of Ser. No. 535,005, Jun. 7, 1990, Pat. No. 5,126,324.

[51] Int. Cl.$^6$ ............................. A61K 38/00; A01N 37/18
[52] U.S. Cl. ........................... 514/12; 514/2; 514/21
[58] Field of Search ........................... 514/2, 12, 21

[56] References Cited

U.S. PATENT DOCUMENTS

| | | | |
|---|---|---|---|
| 4,609,640 | 9/1986 | Morishita et al. | 514/12 |
| 4,857,505 | 8/1989 | Arendt | 514/12 |
| 4,988,675 | 1/1991 | Froesch | 514/4 |
| 5,126,324 | 6/1992 | Clark | 514/12 |
| 5,187,151 | 2/1993 | Clark et al. | |

FOREIGN PATENT DOCUMENTS

| | | |
|---|---|---|
| 123228 | 10/1984 | European Pat. Off. |
| 123304 | 10/1984 | European Pat. Off. |
| 128733 | 12/1984 | European Pat. Off. |
| 193372 | 9/1986 | European Pat. Off. |
| 193917 | 9/1986 | European Pat. Off. |
| 230869 | 8/1987 | European Pat. Off. |
| 261599 | 3/1988 | European Pat. Off. |
| 267015 | 5/1988 | European Pat. Off. |
| 288451 | 10/1988 | European Pat. Off. |
| 308238 | 3/1989 | European Pat. Off. |
| 312208 | 4/1989 | European Pat. Off. |
| 327503 | 8/1989 | European Pat. Off. |
| 58/224687 | 12/1983 | Japan. |
| 57/026625 | 2/1992 | Japan. |
| 2193891 | 2/1988 | United Kingdom. |
| 2160528 | 3/1988 | United Kingdom. |
| WO 87/01038 | 2/1987 | WIPO. |
| WO 89/05822 | 6/1989 | WIPO. |
| WO 91/03253 | 3/1991 | WIPO. |
| WO 93/23071 | 11/1993 | WIPO. |

OTHER PUBLICATIONS

*The Merck Index*, 11th edition, ed. Susan Budavari (Merck & Co., Inc., Rahway, NJ 1989), p. 49.
Merck Index, 11th ed. p. 1207.
J. Zapf et al., *J. Clin. Inv.*, 77, 1768–1775 (1986).
Guler et al., "S.C. Infusion of Recombinant Human Insulin–like Growth Factor I (rhIGF I) Stimulates Growth of Hypophysectomized Rats Continously During 18 Days", *1st European Congress of Endocrinology*, Copenhagen, Jensen & Christiansen, eds., 103:12–390, (Jun. 21–25, 1987).
Guler et al. "Effects of recombinant insulin–Like growth factor I on insulin secretion and renal function in normal human subjects", *Proc. Natl. Acad. Sci. USA*, 86: 2868–2872 (1989).
Schoenle et al., "Comparison of in vivo effects of insulin–like growth factors I and II and of growth hormone in hypophysectomized rats", *Acta Endocrin.*, 108: 167–174 (1985).
Skottner et al., "Recombinant human insulin–like growth factor: testing the somatomedin hypothesis in hypophysectomized rats", *J. Endocr.*, 112: 123–132 (1987).
Skottner et al., "Growth Responses in a Mutant Dwarf Rat to Human Growth Hormone and Recombinant Human Insulin–Like Growth Factor I", *Endocrinology*, 124(5): 2519–2526 (1989).
Tanner et al., "Comparative rapidity of response of height, limb muscle, and limb fat to treatment with human growth hormone in patients with and without growth hormone deficiency", *Acta Endocrinol.*, 84: 681–696 (1977).
Uthne et al., "Effects of Human Somatomedin Preparations on Membrane Transport and Protein Synthesis in the Isolated Rat Diaphragm", *J. Clin. Endocrinol. Metab.*, 39: 548–554 (1974).
Guler et al., "Short–term metabolic effects of recombinant human insulin–like growth factor I in healthy adults", *N. Engl. J. Med.*, 317(3): 137–140 (1987).
Guler et al., "IGF I and II and recombinant human (RH) IGF I are hypoglycemic in the rat, mini–pig and men", *The Endocrine Society, 68th Annual Mtg*, #394, (1986).
Guler et al., "Recombinant human insulin–like growth factor I stimulates growth and has distinct effects on organ size in hypophysectomized rats", *Proc. Natl. Acad. Sci. USA*, 85: 4889–4893 (1988).
Froesch et al., "IGF I and II: in vitro and in vivo effects", *Endocrinology, Intl. Congress Series 655*, Labrie and Proulx, eds. Amsterdam: Excerpta Medica, 475–479 (1984).
Scheiwiller et al., "Growth restoration of insulin–deficient diabetic rats by recombinant human insulin–like growth factor I", *Nature*, 323: 169–171 (1986).
van Buul–Offers et al., "Biosynthetic Somatomedin C(SM–C/IGF–I) Increases the Length and Weight of Snell Dwarf Mice", *Pediatr. Res.*, 20(9): 825–827 (1986).
Niall, "Revised Primary Structure for Human Growth Hormone", *Nature, New Biology*, 230(11): 90–91 (1971).
Moore et al., "Equivalent potency and pharmacokinetics of recombinant human growth hormones with or without an N–terminal methionine", *Endocrinology*, 122(6): 2920–2926 (1988).

(List continued on next page.)

*Primary Examiner*—Toni R. Scheiner
*Assistant Examiner*—Sheela J. Huff
*Attorney, Agent, or Firm*—Janet E. Hasak

[57] ABSTRACT

A formulation for IGF-I is disclosed that is useful in treating hyperglycemic disorders and, in combination with growth hormone, in enhancing growth of a mammal. Also disclosed is a process for preparing a formulation of growth hormone and IGF-I from the IGF-I formulation. The IGF-I formulation comprises about 2–20 mg/ml of IGF-I, about 2–50 mg/ml of an osmolyte, about 1–15 mg/ml of a stabilizer, and a buffered solution at about pH 5–5.5, optionally with a surfactant.

8 Claims, 25 Drawing Sheets

OTHER PUBLICATIONS

Kaplan, *Growth Disorders in Children and Adolescents* 47–69, 131–139, 165–169 (Springfield, IL: Charles C. Thomas, 1964).

Salmon and Daughaday, "A Hormonally Controlled Serum Factor Which Stimulates Sulfate Incorporation by Cartilage In Vitro", *J. Lab. Clin. Med.*, 49(6): 825–836 (1957).

Phillips & Vassilopoulou–Sellin, "Somatomedins", (First of Two Parts), *N. Engl. J. Med.*, 302(7): 371–380 (Feb. 14, 1980).

Phillips & Vassilopoulou–Sellin, "Somatomedins", (Second of Two Parts), *N. Engl. J. Med.*, 302(8): 438–446 (Feb. 21, 1980).

Vetter et al., "Human Fetal and Adult Chondrocytes: Effects of insulinlike growth factors I and II, insulin and growth hormone on clonal growth", *J. Clin. Invest.*, 7: 1903–1908 (1986).

Cook et al., "Mitogenic Effects of Growth Hormone in Cultured Human Fibroblasts", *J. Clin. Invest.*, 81: 206–212 (1988).

Isgaard et al., "Pulsatile intravenous growth hormone (GH) infusion to hypophysectomized rats increases insulin–like growth factor I messenger ribonucleic acid in skeletal tissues more effectively than continuous GH infusion", *Endocrinology*, 123(6): 2605–2610 (1988).

Isaksson et al., "Growth hormone stimulates longitudinal bone growth directly", *Science*, 216: 1237–1239 (1982).

Russell and Spencer, "Local injections of human or rat growth hormone or of purified human somatomedin–C stimulate unilateral tibial epiphyseal growth in hypophysectomized rats", *Endocrinology*, 116(6): 2563–2567 (1985).

Schlechter et al., "A direct growth effect of growth hormone in rat hindlimb shown by arterial infusiion", *Am. J. Physiol.*, 250: E231–235 (1986).

Madsen et al., "Growth hormone stimulates the proliferation of cultured chondrocytes from rabbit ear and rat rib growth cartilage", *Nature*, 304: 545–547 (1983).

Schlechter et al., "Evidence suggesting that the direct growth–promoting effect of growth hormone on cartilage in vivo is mediated by local production of somatomedin", *Proc. Natl. Acad. Sci. USA*, 83: 7932–7934 (1986).

Nilsson et al., "Effects of unilateral arterial infusion of GH and IGF–I on tibial longitudinal bone growth in hypophysectomized rats", *Calcif. Tissue Int.*, 40: 91–96 (1987).

Otonkoski et al., "Effects of growth hormone and insulin–like growth factor I on endocrine function of human fetal islet–like cell clusters during long–term tissue culture", *Diabetes*, 37: 1678–1683 (1988).

Green et al., "A dual effector theory of growth–hormone action", *Differentiation*, 29: 195–198 (1985).

Zezulak and Green, "The Generation of Insulin–Like Growth Factor–1–Sensitive Cells by Growth Hormone Action", *Science*, 233: 551–553 (1986).

Young et al., "Growth hormone and testosterone can independently stimulate the growth of hypophysectomized prepubertal lambs without any alteration in circulating concentrations of insulin–like growth factors", *J. Endocrin.*, 121: 563–570 (1989).

Orlowski and Chernausek, "Discordance of Serum and Tissue Somatomedin Levels in Growth Hormone–Stimulated Growth in the Rat", *Endocrinol.*, 123(1): 44–49 (1988).

Trippel et al., "Effect of Somatomedin–C/Insulin–Like Growth Factor I and Growth Hormone on Cultured Growth Plate and Articular Chondrocytes", *Pediatr. Res.*, 25(1): 76–82 (1989).

Isgaard et al., "Effects of local administration of GH and IGF–1 on longitudinal bone growth in rats", *Am. J. Physiol.*, 250: E367–E372 (1986).

Robinson and Clark, "Growth Promoting Activity of IGF–1 in the Rat", *Acta Paediatr. Scand. Supp.*, 347: 93–103 (1988).

Ernst and Froesch, "Growth hormone dependent stimulation of osteoblast–like cells in serum–free cultures via local synthesis of insulin–like growth factor I," *Biochem. Biophy. Res. Commun.*, 151(1): 142–147 (1988).

Smith et al., "Growth Hormone Stimulates Insulin–like Growth Factor I Actions on Adult Articular Chondrocytes", *J. Orthop. Res.*, 7: 198–207 (1989).

Merchav et al., "Enhancement of Human Granulopoiesis In Vitro by Biosynthetic Insulin–like Growth Factor I/Somatomedin C and Human Growth Hormone", *J. Clin. Invest.*, 81: 791–797 (1988).

Lobie et al., "Growth Hormone Receptor Expression in the Rat Gastrointestinal Tract", *Endocrinol.*, 126: 299–306 (1990).

Lindahl et al., "Growth hormone in vivo potentiates the stimulatory effect of insulin–like growth factor–1 on colony in vitro on colony formation of epiphyseal chondrocytes isolated from hypophysectomized rats", *Endocrinol.*, 121(3): 1070–075 (1987).

van Neste et al., "Cellular distribution of somatogenic receptors and insulin–like growth factor–I mRNA in the rat liver", *J. Endocr.*, 199: 69–74 (1988).

Namba et al., "Insulin–Like Growth Factor–I Action on Growth Hormone Secretion and Messenger Ribonucleic Acid Levels: Interaction with Somatostatin", *Endocrinol.*, 124(4): 1794–1799 (1989).

Yamashita et al., "Regulation of Human Growth Hormone Gene Expression by Insulin–like Growth Factor I in Transfected Cells", *J. Biol. Chem.*, 262(27): 13254–13257 (1987).

Schwartz et al., "Growth hormone and insulin–like growth factors I and II produce distinct alterations in glucose metabolism in 3T3–F442A adipocytes", *Proc. Natl. Acad. Sci. USA*, 82: 8724–8728 (1985).

Horikawa et al., "Growth hormone and insulin–like growth factor I stimulate Leydig cell steroidogenesis", *Eur. J. Pharmacol.*, 166: 87–94 (1989).

Rosselot et al., "Effect of Growth Hormone and Insulin–Like Growth Factor I on Cell Proliferation and Metabolic Activity of Cultured Chondrocytes", *The Endocrine Society 72nd Annual Meeting*, abstract 202, p. 75, of Program and Abstracts released prior to the meeting in Atlanta, GA on Jun. 20, 23, 1990.

Watanabe et al., "Characterization of a specific insulin–like growth factor–/I/somatomedin–C receptor on high density, primary monolayer cultures of bovine articular chondrocytes: regulation of receptor concentration by somatomedin insulin and growth hormone", *J. Endocr.*, 107: 275–283 (1985).

Ikkos et al., "The Effect of Human Growth Hormone in Man", *Acta Endocrinol.* (Copenhagen), 32: 341–361 (1959).

Biglieri et al., "Sodium Retention with Human Growth Hormone and its Subfractions", *J. Clin. Encodrinol. Metab.*, 21(4): 361–370 (1961).

Remington's *Pharmaceutical Sciences*, 18th edition, chapter 62, p. 1170, definition of benzethonium chloride (1990).
Martindale, *The Extra Pharmacopeia*, 28th edition p.550, entry on benzethonium chloride.
*United States Pharmacopeia*, Official Monographs, 22nd edition, pp.146–147, entries on benzethonium chloride topical solution and tincture (1990).

*Handbook of Injectable Drugs*, 5th edition, pp. 246–251, entry on diphenhydramine HCl; pp. 396–397, entry on ketamine HCl; and pp. 695–696, entry on Vidarabine.
Woodall et al., "The Effect of the Frequency of Subcutaneous Insulin–Like Growth Factor I Administration on Weight Gain in Growth Hormone Deficient Mice", *Horm. Metabl. Res.*, 23: 581–584 (1991).

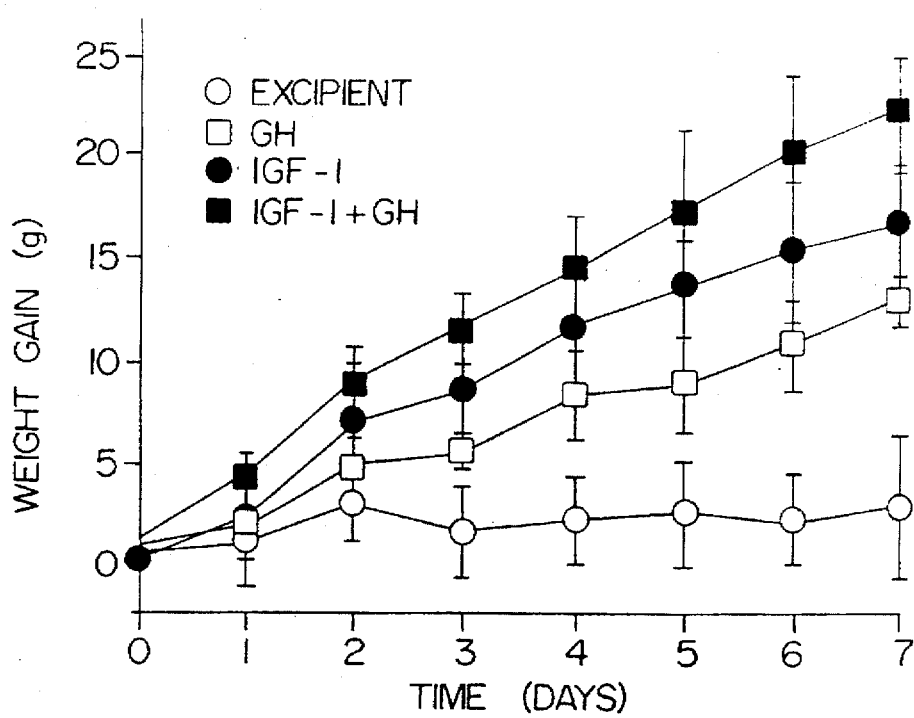
FIG. IA
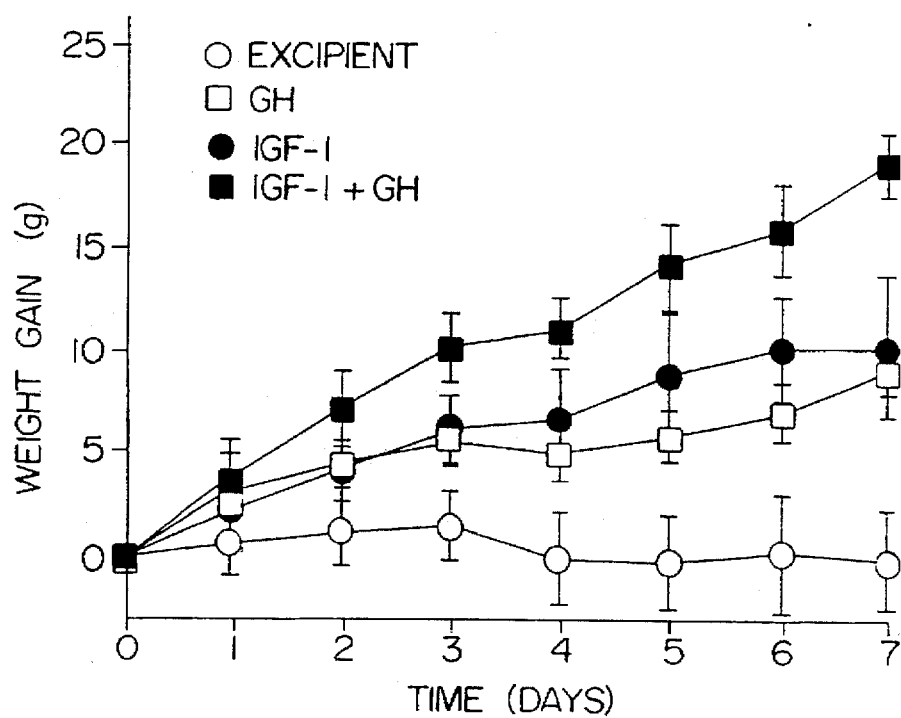
FIG. IB

FIG. 8B

FORMULATED IGF-I COMPOSITION

This application is a continuation-in-part application of U.S. Ser. No. 07/806,748 filed Dec. 13, 1991, now abandoned, which is a divisional application of U.S. Ser. No. 07/535,005 filed Jun. 7, 1990, now issued as U.S. Pat. No. 5,126,324.

BACKGROUND OF THE INVENTION

1. Field of the Invention

This invention relates to formulations containing IGF-I useful in treating all pathological or other conditions that can be ameliorated or improved using IGF-I, including treating hyperglycemia and enhancing growth (anabolism) in patients, particularly those exhibiting a retarded growth rate or weight loss using a combination of natural hormones.

2. Description of Related Art

Insulin-like growth factor I (IGF-I) is a polypeptide naturally occurring in human body fluids, for example, blood and human cerebral spinal fluid. Most tissues and especially the liver produce IGF-I together with specific IGF-binding proteins. These molecules are under the control of growth hormone (GH). Like GH, IGF-I is a potent anabolic protein. See Tanner et al., *Acta Endocrinol.*, 84: 681–696 (1977); Uthne et al., *J. Clin. Endocrinol. Metab.*, 39: 548–554 (1974)). IGF-I has been isolated from human serum and produced recombinantly. See, e.g., EP 123,228 and 128,733.

Various biological activities of IGF-I have been identified. Researchers have found that an intravenous bolus injection of IGF-I lowers blood glucose levels in humans. See Guler et al., *N. Engl. J. Med.*, 317: 137–140 (1987). Additionally, IGF-I promotes growth in several metabolic conditions characterized by low IGF-I levels, such as hypophysectomized rats [Guler et al., *Endocrinology*, 118: Supp 129 abstract, Skottner et al., *J. Endocr.*, 112: 123–132 (1987); Guler et al., *Proc. Natl. Acad. Sci. USA*, 85: 4889–4893 (1988); Froesch et al., in *Endocrinology, Intl. Congress Series* 655, ed. by Labrie and Proulx (Amsterdam: Excerpta Medica, 1984), p. 475–479], diabetic rats [Scheiwiller et al., *Nature*, 323: 169–171 (1986)], and dwarf rats [Skottner et al., *Endocrinology*, 124: 2519–2526 (1989)]. The kidney weight of hypophysectomized rats increases substantially upon prolonged infusions of IGF-I subcutaneously. Guler et al., *Proceedings of the 1st European Congress of Endocrinology*, 103: abstract 12–390 (Copenhagen, 1987). The kidneys of Snell dwarf mice and dwarf rats behaved similarly. van Buul-Offers et al., *Pediatr. Res.*, 20: 825–827 (1986); Skottner et al., *Endocrinology*, supra. An additional use for IGF-I is its administration to improve glomerular filtration and renal plasma flow in human patients. See EP 327,503 published Aug. 9, 1989; Guler et al., *Proc. Natl. Acad. Sci. USA*, 86: 2868–2872 (1989).

Human growth hormone (hGH) is a single-chain polypeptide consisting of 191 amino acids (molecular weight 21,500). Disulfide bonds link positions 53 and 165 and positions 182 and 189. Niall, *Nature, New Biology*, 230: 90 (1971). Human GH is a potent anabolic agent, especially due to retention of nitrogen, phosphorus, potassium, and calcium. Treatment of hypophysectomized rats with GH can restore at least a portion of the growth rate of an intact animal. Moore et al., *Endocrinology*, 122: 2920–2926 (1988). Among its most striking effects in hypopituitary (GH-deficient) subjects is accelerated linear growth of bone growth plate cartilage resulting in increased stature. Kaplan, *Growth Disorders in Children and Adolescents* (Springfield, Ill.: Charles C. Thomas, 1964).

In 1957, the mechanism of GH action was postulated as being due to GH inducing production of somatomedins (subsequently identified and named IGF-I) in the liver, which travel via the circulation to produce all the effects of GH. Salmon and Daughaday, *J. Lab. Clin. Med.*, 49: 825–836 (1957). Many studies investigating the relationships among GH, IGF-I, cartilage, cultured human fibroblasts, skeletal muscle, and growth have supported this somatomedin hypothesis. See, e.g., Phillips and Vassilopoulou-Sellin, *N. Engl. J. Med.*, 302: 372–380; 438–446 (1980); Vetter et al., *J. Clin. Invest.*, 7: 1903–1908 (1986); Cook et al., *J. Clin. Invest.*, 81: 206–212 (1988); Isgaard et al., *Endocrinology*, 123: 2605–2610 (1988); Schoenle et al., *Acta Endocrin.*, 108: 167–174 (1985).

Another theory holds that GH has a direct effect on chondrocytes that is not dependent on circulating IGF-I. For example, several in vivo studies have demonstrated longitudinal long bone growth in rats receiving hGH injected directly into the tibial growth plate [Isaksson et al., *Science*, 216: 1237–1239 (1982); Russell and Spencer, *Endocrinology*, 116: 2563–2567 (1985)] or the arterial supply to a limb [Schlechter et al., *Am. J. Physiol.*, 250: E231–235 (1986)]. Additionally it was found that proliferation of cultured lapine ear and rib chondrocytes in culture is stimulated by hGH [Madsen et al., *Nature*, 304: 545–547 (1983)], this being consistent with a direct GH effect or with an indirect effect of GH mediated by local GH-dependent IGF-I production. Such an autocrine or paracrine model for stimulation of growth has been supported by various lines of experimental evidence. Schlechter et al., *Proc. Natl. Acad. Sci. USA*, 83: 7932–7934 (1986); Nilsson et al., *Calcif. Tissue Int.*, 40: 91–96 (1987). Nilsson et al. showed that while unilateral arterial infusion of IGF-I did not produce a tibial longitudinal bone growth response in hypophysectomized rats, infusion of hGH did induce such growth. Moreover, the influence of GH on the functional maturation of human fetal islet cells in vitro could not be reproduced by adding IGF-I, suggesting a direct rather than a somatomedin-mediated action of GH for these particular cells. Otonkoski et al., *Diabetes*, 37: 1678–1683 (1988).

A third theory for GH and IGF-I actions is that GH promotes differentiation of stem cells, rendering them responsive to stimulation of proliferation by IGF-I. Green et al., *Differentiation*, 29: 195–198 (1985). Although support for this model of GH acting to produce IGF-I locally, called the dual effector theory, has been obtained for certain cell types [Zezulak and Green, *Science*, 233: 551–553 (1986)], its application to skeletal growth has not been established. It has been found that both GH and testosterone could stimulate skeletal growth in the hypophysectomized prepubertal lamb without alteration of circulating IGF-I concentrations, the results not precluding the possibility that the growth-promoting effect of GH was affected by local actions at the site of osteogenesis. Young et al., *J. Endocrin.*, 121: 563–570 (1989). Also, GH has been reported to stimulate tibial epiphyseal plate width in the hypophysectomized rat without increasing circulating IGF-I concentrations. Orlowski and Chernausek, *Endocrinol.*, 123: 44–49 (1988).

More recently, a study was undertaken to reproduce the "direct" in vitro GH effect on epiphyseal and articular chondrocytes to determine whether this effect is mediated by IGF-I in a local autocrine or paracrine fashion. Trippel et al., *Pediatr. Res.*, 25: 76–82 (1989). Human GH was found not to stimulate rabbit articular or epiphyseal chondrocytes or bovine epiphyseal chondrocytes, whereas IGF-I stimulated both mitotic and differentiated cell functions in both epiphyseal and articular chondrocytes. The authors state that the data suggest that the role of IGF-I in skeletal development is complex and may be diverse both in the cellular functions it regulates and the cell populations regulated, requiring further investigation to define the relationship of IGF-I to GH.

It has been reported that the growth response to co-addition of GH and IGF-I was not statistically different from that of GH alone when body weight gain, bone length, or tibial epiphyseal cartilage width was measured. Skottner et al., *J. Endocr.*, supra [iv infusion of bGH (10 mu/day) for 8 days and met-IGF-I (with specific activity of 3400 U/mg, 120 µg/day) for the last 4 days]; Isgaard et al., *Am. J. Physiol.*, 250: E367–E372 (1986) [5 µg of IGF-I and 1 µg of hGH injected locally daily for 5 days]. It was also found that IGF-I, when injected or infused subcutaneously or infused intravenously, is a weak growth promoter in hypophysectomized rats compared with hGH, even when infused in combination with small amounts of hGH. Robinson and Clark, *Acta Paediatr. Scand. Supp.*, 347: 93–103 (1988).

As regards osteoblast-like cells in culture, direct stimulation of their proliferation by hGH is at least partially mediated by IGF-I-like immunoreactivity [Ernst and Froesch, *Biochem. Biophy. Res. Commun.*, 151: 142–147 (1988)]; the authors found that IGF-I and hGH had additive effects on osteoblast proliferation only when the exogenous IGF-I concentration exceeded that of endogenously produced IGF-I by a large margin. Another in vitro study showed that purified human and synthetic IGF-I stimulated adult articular chondrocyte DNA and proteoglycan synthesis; GH had no effect on either process; and GH added in combination with IGF-I increased proteoglycan, cell-associated proteoglycan, and keratan sulfate synthesis over levels observed with IGF-I alone. Smith et al., *J. Orthop. Res.*, 7: 198–207 (1989). Separate administration of hGH and IGF-I was found to enhance human granulopoiesis, with the effect of hGH on marrow myeloid progenitors apparently mediated by paracrine IGF-I. Merchav et al., *J. Clin. Invest.*, 81: 791–797 (1988). Merchav et al. also noted that myeloid colony formation was significantly enhanced in cultures stimulated with combined limiting concentrations of both IGF-I and hGH, whereas combined maximal concentrations of both peptides did not exert an additive effect.

Also, based on recent immunohistochemical data regarding the GH receptor, it has been suggested that GH may act independently of or synergistically with hepatic IGF-I in carrying out its growth-promoting role in the gastrointestinal tract. Lobie et al., *Endocrinol.*, 126: 299–306 (1990). It has been shown that pretreatment of hypophysectomized rats with GH, but not with IGF-I, promotes the formation of chondrocyte colonies and makes the chondrocytes susceptible to IGF-I in vitro. Lindahl et al., *Endocrinol.*, 121: 1070–1075 (1987). The authors suggest that GH induces colony formation by IGF-I-independent mechanisms and that IGF-I is a second effector in GH action. Further, treatment of hypophysectomized animals with a single dose of hGH restored IGF-I mRNA in parenchymal and in non-parenchymal cells to the extent found in intact animals. van Neste et al., *J. Endocr.*, 119: 69–74 (1988).

However, it has also been reported that IGF-I directly suppresses GH gene transcription and GH secretion at the pituitary level in an inhibitory feedback control mechanism. Namba et al., *Endocrinol.*, 124: 1794–1799 (1989); Yamashita et al., *J. Biol. Chem.*, 262: 13254–13257 (1987). Additionally, it was reported that the maximum stimulation of glucose metabolism in 3T3 adipocytes achieved by hGH is only a fraction of that produced by various IGFs, indicating that extracellular IGFs do not mimic the effects of hGH on glucose metabolism in these adipocytes. Schwartz et al., *Proc. Natl. Acad. Sci. USA*, 82: 8724–8728 (1985). Moreover, human GH was found not to enhance further the IGF-I-stimulated Leydig cell steroidogenesis. Horikawa et al., *Eur. J. Pharmacol.*, 166: 87–94 (1989). Another negative finding was that the combination of chick growth hormone and human IGF-I did not stimulate cell proliferation and metabolic activity of cultured epiphyseal growth plate chondrocytes above human IGF-I alone. Rosselot et al., *The Endocrine Society 72nd Annual Meeting*, abstract 202, p. 75, of Program and Abstracts released prior to the meeting in Atlanta, Ga. on Jun. 20–23, 1990. It has also been reported that both hGH and hIGF-I can promote growth in the mutant dwarf rat, but they differ both quantitatively and qualitatively in their pattern of actions. Skottner et al., *Endocrinology*, supra. Additionally, a loss of IGF-I receptors in cultured bovine articular chondrocytes was found after pre-exposure of the cells to pharmacological doses of either hGH or bGH. Watanabe et al., *J. Endocr.*, 107: 275–283 (1985). The necessity for large amounts of GH is attributed to extremely low affinity of GH binding sites on these cells. The authors speculate that living organisms have a protection mechanism to avoid unnecessary overgrowth of the body resulting in down-regulation of the IGF-I receptors.

U.S. Pat. No. 4,857,505 issued Aug. 15, 1989 discloses use of an adduct of a growth hormone, growth factor, IGF-I, or fragment thereof covalently bonded to an activated polysaccharide for increased half-life, increased weight gain in animals, and increased milk production.

Known side effects of hGH treatment include sodium retention and expansion of extracellular volume [Ikkos et al., *Acta Endocrinol.* (Copenhagen), 32: 341–361 (1959); Biglieri et al., *J. Clin. Endocrinol. Metab.*, 21: 361–370 (1961)], as well as hyperinsulinemia and hyperglycemia. The major apparent side effect of IGF-I is hypoglycemia. Guler et al., *Proc. Natl. Acad. Sci. USA*, 1989, supra.

Various methods for formulating proteins or polypeptides have been described. These include EP 267,015 published May 11, 1988; EP 308,238 published Mar. 22, 1989; and EP 312,208 published Apr. 19, 1989, which disclose formulation of a polypeptide growth factor having mitogenic activity, such as transforming growth factor-β (TGF-β), in a polysaccharide such as methylcellulose; EP 261,599 published Mar. 30, 1988 disclosing human topical applications containing growth factors such as TGF-β; EP 193,917 published Sep. 10, 1986, which discloses a slow-release composition of a carbohydrate polymer such as a cellulose and a protein such as a growth factor; GB Pat. No. 2,160,528 granted Mar. 9, 1988, describing a formulation of a bioactive protein and a polysaccharide; and EP 193,372 published Sep. 3, 1986, disclosing an intranasally applicable powdery pharmaceutical composition containing an active polypeptide, a quaternary ammonium compound, and a lower alkyl ether of cellulose. See also U.S. Pat. No. 4,609,640 issued Sep. 2, 1986 disclosing a therapeutic agent and a water-soluble chelating agent selected from polysaccharides, celluloses, starches, dextroses, polypeptides, and synthetic polymers able to chelate Ca and Mg; and JP 57/026625 published Feb. 12, 1982 disclosing a preparation of a protein and water-soluble polymer such as soluble cellulose.

EP 123,304 published 31 Oct. 1984 discloses mixing tissue plasminogen activator with gelatin or Polysorbate 80, and JP 58/224,687 published 27 Dec. 1983 [Toryo, *Chem. Abs.*, 100: 197765r (1984)] discloses formulation of plasminogen-activating enzyme with PEG-3-sorbitan monooleate, dextrin, gelatin, mannitol, dextran, glycine, and hydrolyzed gelatin for stability.

Furthermore, preservatives containing a quaternary ammonium salt have been added to chemical drug formulations to prevent growth of bacteria. See, e.g., Remington's *Pharmaceutical Sciences*, 18th edition (definition of benzethonium chloride), Martindale, *The Extra Pharmacopeia*, 28th edition (p.550, entry on benzethonium chloride), *United States Pharmacopeia*, 22nd edition (pp. 146–147, entries on benzethonium chloride topical solution and tincture), *Handbook on Injectable Drugs*, 5th edition (p. 246, entry on diphenhydramine HCl, which contains 0.1% benzethonium chloride; pp. 396–397, entry on ketamine HCl, which contains 0.1 mg/ml of benzethonium chloride; and pp. 695–696, entry on Vidarabine, which contains 0.1 mg benzethonium chloride). Another example is the formulation of octreotide in benzalkonium chloride for nasal application as described in GB Appln. 2,193,891 published Feb. 24, 1988. The preservatives have been used in parenteral formulations at low concentrations, and in antiseptic washes for wound care at higher concentrations. In addition, a mixture of a physiologically active polypeptide with a quaternary ammonium compound and a lower alkyl ether of cellulose is disclosed, wherein the quaternary ammonium compound is added to improve stability and preservability. EP 193,372.

It is an object of the present invention to provide a formulation of IGF-I that is more potent as a hypoglycemic agent and better absorbed when administered subcutaneously than an existing IGF-I formulation.

It is another object to provide an IGF-I formulation useful along with a GH formulation in the treatment of patients.

It is yet another object to provide an IGF-I formulation useful for preparing a formulation of both IGF-I and GH, and methods for such preparation.

These and other objects will be apparent to those of ordinary skill in the art.

SUMMARY OF THE INVENTION

Accordingly, the present invention provides an IGF-I-containing composition comprising about 2–20 mg/ml of IGF-I, about 2–50 mg/ml of an osmolyte, about 1–15 mg/ml of a stabilizer, and a buffered solution at about pH 5–5.5. This composition has been found, preferably at pH 5.4, to be more potent as a hypoglycemic agent than a pH 6.0 citrate-buffered IGF-I formulation when administered subcutaneously, and to be better absorbed than the pH 6.0 formulation when administered subcutaneously.

Therefore, in a further aspect, the invention supplies a method for treating hyperglycemic disorders comprising administering to a mammal having such disorder an effective amount of the above IGF-I formulation, preferably subcutaneously.

In a still further aspect, the invention provides a process for preparing a formulation comprising mixing the above composition with a buffered solution comprising GH at pH about 6 in a dose (mg) ratio of from about 2:1 to 100:1 IGF-I:GH up to a dose no greater than about 5 mg/ml GH.

The literature shows that the role of IGF-I in skeletal development in conjunction with GH is complex, and evidence supporting various theories of GH action is contradictory and inconclusive. If GH acts via production of circulating IGF-I (the somatomedin hypothesis), then a maximal dose of GH would not be expected to be enhanced by administering IGF-I systemically. If GH acts locally to produce IGF-I, then it is unlikely that the high local concentrations of IGF-I predicted by this second theory could be reproduced by administering IGF-I systemically. If some actions of GH do not involve IGF-I generation, then adding GH might enhance the effect of IGF-I. However, in view of the confusion surrounding which of these three unresolved theories is correct, there was no clear basis to predict the outcome on body and bone growth of administering to a mammal a combination of GH and IGF-I.

Unexpectedly, a significantly greater daily body weight gain, increased longitudinal bone growth, and enhanced epiphyseal width of the tibia were achieved after combination treatment with IGF-I and GH as compared with the same doses of each of IGF-I and GH alone. Further, the additive effect of IGF-I and GH was not seen for all tissues, indicating a selectivity for whole body growth, bone, and cartilage. Moreover, IGF-I enhanced the growth-promoting effect of GH even at the maximum effective dose of GH, and can further enhance a low dose of GH to produce a maximal growth response. Thus, IGF-I may be used in combination with lower doses of GH to increase growth of those immature patients that have reached their maximum growth rate after treatment with maximal doses of GH alone and then experienced a fall in their annualized growth rate. This is an effect that is widespread in all growth-deficient patients after several months of treatment. The combination could also be used to maximize the growth response in patients who present late in development with growth retardation, and only have a few years of therapeutic intervention potential. Additionally, the combination can be used to treat those patients who exhibit side effects such as diabetogenic symptoms with maximum doses of GH or hypoglycemia with maximum doses of IGF-I.

In addition, the IGF-I formulation herein can be used by itself in the treatment of hyperglycemic disorders as noted above.

BRIEF DESCRIPTION OF THE DRAWINGS

FIGS. 1(A and B) represent graphs of cumulative body weight gain over seven days for each group of treated hypophysectomized adult male rats for two replicate studies 1 and 2, respectively, performed one month apart (means±SD).

FIG. 8A and 8B illustrate bar graphs of the growth rate in cm/year of patients of various growth inhibition etiologies having had either no previous treatment (Prev Rx No) or previous treatment (Prev Rx Yes) with hGH. N indicates the number of patients at the indicated dose level of hGH given in units of mg/kg. FIG. 8A is the data for the first year of hGH treatment and FIG. 8B is for the second year of hGH treatment.

DESCRIPTION OF THE PREFERRED EMBODIMENTS

A. Definitions

Figure 2:
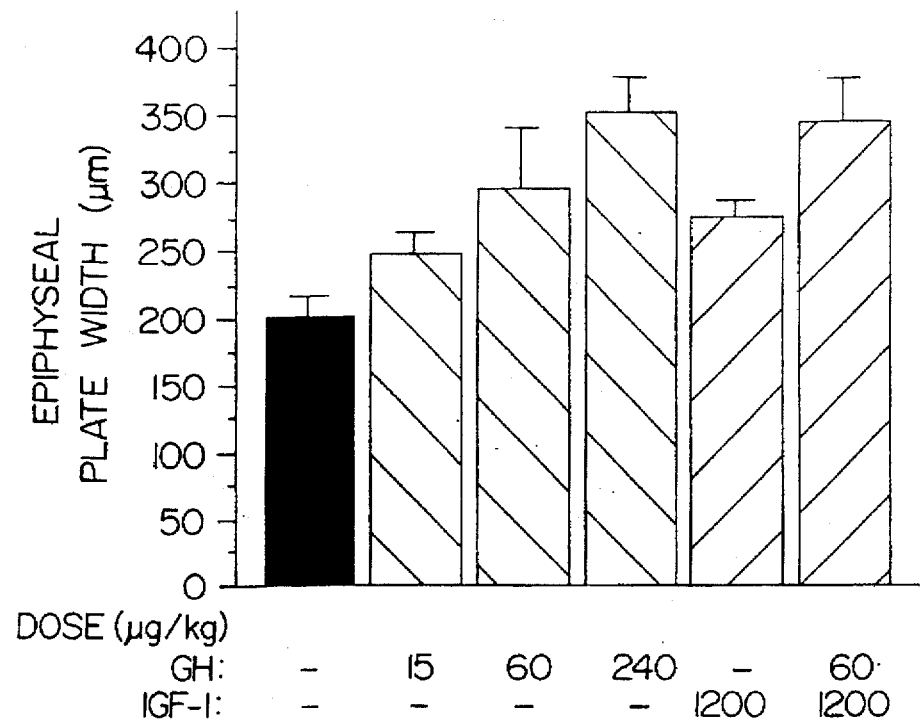
FIG. 2 shows a bar graph of the increase in width of epiphyseal bone growth plate after seven days of hGH and/or IGF-I treatment of hypophysectomized rats (means±SD).

As used herein, "mammal" signifies humans as well as animals, and includes animals of economic importance such as bovine, ovine, and porcine animals. The preferred mammal herein is a human. The term "non-adult" refers to mammals that are from perinatal age (such as low-birth-weight infants) up to the age of puberty, the latter being those that have not yet reached full growth potential.

As used herein, "IGF-I" refers to insulin-like growth factor from any species, including bovine, ovine, porcine, equine, and preferably human, in native-sequence or in variant form, and from any source, whether natural, synthetic, or recombinant. Preferred herein for animal use is that form of IGF-I from the particular species being treated, such as porcine IGF-I to treat pigs, ovine IGF-I to treat sheep, bovine IGF-I to treat cattle, etc. Preferred herein for human use is human native-sequence, mature IGF-I, more preferably without a N-terminal methionine, prepared, e.g., by the process described in EP 230,869 published Aug. 5, 1987; EP 128,733 published Dec. 19, 1984; or EP 288,451 published Oct. 26, 1988. More preferably, this native-sequence IGF-I is recombinantly produced and is available from Genentech, Inc., South San Francisco, Calif. for clinical investigations. Also preferred for use is IGF-I that has a specific activity greater than about 14,000 units/mg as determined by radioreceptor assay using placenta membranes, such as that available from KabiGen AB, Stockholm, Sweden.

The most preferred IGF-I variants are those described in PCT WO 87/01038 published Feb. 26, 1987 and in PCT WO 89/05822 published Jun. 29, 1989, i.e., those wherein at least the glutamic acid residue is absent at position 3 from the N-terminus of the mature molecule or those having a deletion of up to five amino acids at the N-terminus. The most preferred variant has the first three amino acids from the N-terminus deleted (variously designated as brain IGF, tIGF-I, des(1–3)-IGF-I, or des-IGF-I).

As used herein, "GH" refers to growth hormone from any species, including bovine, ovine, porcine, equine, and preferably human, in native-sequence or in variant form, and from any source, whether natural, synthetic, or recombinant. Preferred herein for animal use is that form of GH from the particular species being treated, such as porcine GH to treat pigs, ovine GH to treat sheep, bovine GH to treat cattle, etc. Preferred herein for human use is human native-sequence, mature GH with or without a methionine at its N-terminus. Also preferred is recombinant hGH, i.e., that produced by means of recombinant DNA technology. More preferred is methionyl human growth hormone (met-hGH) produced in *E. coli*, e.g., by the process described in U.S. Pat. No. 4,755,465 issued Jul. 5, 1988 and Goeddel et al., *Nature*, 282: 544 (1979). Met-hGH, which is sold under the trademark PROTROPIN® by Genentech, Inc., is identical to the natural polypeptide, with the exception of the presence of an N-terminal methionine residue. This added amino acid is a result of the bacterial protein synthesis process.

Another preferred hGH for human use is a recombinant hGH (rhGH), available to clinical and research investigators from Genentech, Inc. under the trademark Nutropin®, and commercially available from Eli Lilly, that lacks this methionine residue and has an amino acid sequence identical to that of the natural hormone. See Gray et al., *Biotechnology*, 2: 161 (1984). Both met-hGH and rhGH have equivalent potencies and pharmacokinetic values. Moore et al., supra.

As used herein, the term "growth" refers to the dynamics of statural growth experienced by an individual during infancy, childhood, and adolescence as depicted by a normal growth curve. Thus, growth herein refers to the growth of linear-producing bone plate driven by chondrocytes, as distinguished from the growth of osteoblast cells, derived from a different part of the bone. Restoration of normal growth patterns would allow the patient to approach a more satisfactory growth curve. Examples of patients that are relatively resistant to GH but require treatment to induce an anabolic effect include those with Turner's Syndrome, GH-deficient children who grow poorly in response to GH treatment, children who experience a slowing or retardation in their normal growth curve about 2–3 years before their growth plate closes, so that GH administered alone would no longer increase growth of the children, so-called short normal children, and patients where the IGF-I response to GH has been blocked chemically (i.e., by glucocorticoid treatment) or by a natural condition such as in adult patients or in catabolic patients where the IGF-I response to GH is naturally reduced.

B. Modes for Carrying Out the Invention

The IGF-I and GH are directly administered to the mammal by any suitable technique, including parenterally, intranasally, intrapulmonarily, or orally. They need not be administered by the same route and can be administered locally or systemically. The specific route of administration will depend, e.g., on the medical history of the patient, including any perceived or anticipated side or reduced anabolic effects using hGH or IGF-I alone, and the growth defect to be corrected. Examples of parenteral administration include subcutaneous, intramuscular, intravenous, intraarterial, and intraperitoneal administration. Most preferably, the administration is by continuous infusion (using, e.g., minipumps such as osmotic pumps), or by injection (using, e.g., intravenous or subcutaneous means). Preferably, the administration is subcutaneous for both IGF-I and GH. The administration may also be as a single bolus or by slow-release depot formulation.

Most preferably, the IGF-I is administered by injection, most preferably subcutaneously, at a frequency of, preferably, one-half, once, twice, or three times daily, most preferably daily. Most preferably, the GH is administered daily subcutaneously by injection. Co-injection of the IGF-I and GH is an optimal drug delivery system to ensure normal growth of the mammal, i.e., no overgrowth. Hence, delivery of hGH and IGF-I by injection will be the preferred form of administration for body growth/anabolism, as it will preserve normal body proportions.

In addition, the IGF-I is suitably administered together with its binding protein, for example, BP53, which is described in WO 89/09268 published Oct. 5, 1989, which is equivalent to U.S. Ser. No. 07/171,623 filed Mar. 22, 1988, now U.S. Pat. No. 5,258,287, and by Martin and Baxter, *J. Biol. Chem.*, 261: 8754–8760 (1986), the disclosures of which are incorporated herein by reference. This administration may be by the method described in U.S. Pat. No. 5,187,151. This protein is an acid-stable component of about 53 Kd on a non-reducing SDS-PAGE gel of a 125–150 Kd glycoprotein complex found in human plasma that carries most of the endogenous IGFs and is also regulated by GH. The IGF-I is also suitably coupled to a receptor or antibody or antibody fragment for administration. Similarly, the GH can be delivered coupled to another agent such as an antibody, an antibody fragment, or one of its binding proteins.

The IGF-I and GH composition(s) to be used in the therapy will be formulated and dosed in a fashion consistent with good medical practice, taking into account the clinical condition of the individual patient (especially the side effects of treatment with hGH or IGF-I alone or growth retardation after continuous GH treatment), the site of delivery of the IGF-I and GH composition(s), the method of administration, the scheduling of administration, and other factors known to practitioners. The "effective amounts" of each component for purposes herein are thus determined by such considerations and must be amounts that enhance growth of the treated patient over growth enhancement that is obtained using the same amount of IGF-I or GH individually.

As a general proposition, the total pharmaceutically effective amount of each of the IGF-I and GH administered parenterally per dose will be in the range of about 1 μg/kg/day to 100 mg/kg/day of patient body weight, although, as noted above, this will be subject to a great deal of therapeutic discretion. More preferably, this dose is at least 0.1 mg/kg/day, and most preferably at least 1 mg/kg/day for each hormone. If given continuously, the IGF-I and GH are each typically administered at a dose rate of about 1 μg/kg/hour to about 50 μg/kg/hour, either by 1–4 injections per day or by continuous subcutaneous infusions, for example, using a minipump. An intravenous bag solution may also be employed. The key factor in selecting an appropriate dose is the result obtained, as measured by increases in body weight gain, lean body mass, or statutory growth approximating the normal range, or by other criteria for measuring growth as defined herein as are deemed appropriate by the practitioner.

The IGF-I and GH are also suitably administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (U. Sidman et al., *Biopolymers*, 22, 547–556 (1983)), poly(2-hydroxyethyl methacrylate) (R. Langer et al., *J. Biomed. Mater. Res.*, 15: 167–277 (1981), and R. Langer, *Chem. Tech.*, 12: 98–105 (1982)), ethylene vinyl acetate (R. Langer et al., Id.) or poly-D-(−)-3-hydroxybutyric acid (EP 133, 988). Sustained-release IGF-I compositions also include liposomally entrapped IGF-I. Liposomes containing IGF-I are prepared by methods known per se: DE 3,218,121; Epstein et al., *Proc. Natl. Acad. Sci. U.S.A.*, 82: 3688–3692 (1985); Hwang et al., *Proc. Natl. Acad. Sci. U.S.A.*, 77: 4030–4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal IGF-I and GH therapy.

For parenteral administration, in one embodiment, the IGF-I and GH are formulated generally by mixing each at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the IGF-I and GH each uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; nonionic surfactants such as polysorbates, poloxamers, or PEG; and/or neutral salts, e.g., NaCl, KCl, $MgCl_2$, $CaCl_2$, etc.

The IGF-I and GH are each typically formulated individually in such vehicles at a concentration of about 0.1 mg/ml to 100 mg/ml, preferably 1–10 mg/ml, at a pH of about 4.5 to 8. Full-length IGF-I is generally stable at a pH of no more than about 6.5; des(1-3)-IGF-I is stable at about 3.2 to 5; hGH is stable at a higher pH of about 5.5–9. It will be understood that use of certain of the foregoing excipients, carriers, or stabilizers will result in the formation of IGF-I or GH salts.

In addition, the IGF-I and GH, preferably the full-length IGF-I, are suitably formulated together in a suitable carrier vehicle to form a pharmaceutical composition that does not contain cells. In one embodiment, the buffer used for formulation will depend on whether the composition will be employed immediately upon mixing or stored for later use. If employed immediately after mixing, a mixture of full-length IGF-I and GH can be formulated in mannitol, glycine, and phosphate, pH 4–6. If this mixture is to be stored, it is formulated in a buffer at a pH of about 5–6, such as acetate or citrate, with a surfactant that increases the solubility of the GH at this pH, such as 0.1–0.2% polysorbate 20 or poloxamer 188. The final preparation may be a stable liquid or lyophilized solid.

In one particularly preferred embodiment, the composition comprises IGF-I and GH in a weight ratio of IGF-I:GH of between about 2:1 and 100:1 (w/w), about 0.05–0.3 mM of an osmolyte, preferably an inorganic salt and/or sugar alcohol, about 0.1–10 mg/ml of at least one stabilizer, about 1–5 mg/ml of a surfactant, and about 5 to 100 mM of a buffer at about pH 5–6. The more preferred amounts of IGF-I and GH in this composition are about 2–20 mg/ml IGF-I and about 0.2–10 mg/ml GH. The more preferred weight ratio of IGF-I:GH is about 3:1 to 50:1, more preferably about 3:1 to 30:1, and still more preferably about 3:1 to 25:1, and most preferably about 5:1 to 20:1.

An "osmolyte" refers to an isotonic modifier or osmotic adjuster that lends osmolality to the buffered solution. Osmolality refers to the total osmotic activity contributed by ions and nonionized molecules to a solution. Examples include inorganic salts such as sodium chloride and potassium chloride, mannitol, polyethylene glycols (PEGs), polypropylene glycol, glycine, sucrose, glycerol, amino acids, and sugar alcohols such as mannitol known to the art that are generally regarded as safe (GRAS). The preferred osmolyte herein is sodium chloride or potassium chloride.

The "stabilizer" is any compound that functions to preserve the active ingredients in the formulation, i.e., GH and IGF-I, so that they do not degrade or otherwise become inactive over a reasonable period of time or develop pathogens or toxins that prevent their use. Examples of stabilizers include preservatives that prevent bacteria, viruses, and fungi from proliferating in the formulation, anti-oxidants, or other compounds that function in various ways to preserve the stability of the formulation.

For example, quaternary ammonium salts are useful stabilizers in which the molecular structure includes a central nitrogen atom joined to four organic (usually alkyl or aryl) groups and a negatively charged acid radical. These salts are useful as surface-active germicides for many pathogenic non-sporulating bacteria and fungi and as stabilizers. Examples include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of stabilizers include aromatic alcohols such as phenol and benzyl alcohol, alkyl parabens such as methyl or propyl paraben, and m-cresol. The most preferred stabilizer herein is phenol or benzyl alcohol.

The stabilizer is included in a stable liquid form of the GH and IGF-I formulation, but not in a lyophilized form of the formulation. In the latter case, the stabilizer is present in the bacteriostatic water for injection (BWFI) used for reconstitution. The surfactant is also optionally present in the reconstitution diluent.

The "inorganic salt" is a salt that does not have a hydrocarbon-based cation or anion. Examples include sodium chloride, ammonium chloride, potassium chloride, magnesium chloride, calcium chloride, sodium phosphate, calcium phosphate, magnesium phosphate, potassium phosphate, ammonium phosphate, sodium sulfate, ammonium sulfate, potassium sulfate, magnesium sulfate, calcium sulfate, etc. Preferably, the cation is sodium and the anion is chloride or sulfate, and the most preferred inorganic salt is potassium chloride or sodium chloride.

The "surfactant" acts to increase the solubility of the IGF-I and GH at a pH about 4–7. It is preferably a nonionic surfactant such as a polysorbate, e.g., polysorbates 20, 60, or 80, a poloxamer, e.g., poloxamer 184 or 188, or any others known to the art that are GRAS. More preferably, the surfactant is a polysorbate or poloxamer, more preferably a polysorbate, and most preferably polysorbate 20.

The "buffer" may be any suitable buffer that is GRAS and confers a pH of 5–6 on the GH+IGF-I formulation and a pH of about 5–5.5 on the IGF-I formulation. Examples include acetic acid salt buffer, which is any salt of acetic acid, including sodium acetate and potassium acetate, succinate buffer, phosphate buffer, citrate buffer, or any others known to the art to have the desired effect. The most preferred buffer is sodium acetate, optionally in combination with sodium citrate.

The most preferred composition containing both IGF-I and GH is the following: about 7–10 mg/ml of IGF-I, about 0.2–1.5 mg/ml of GH at a weight ratio of IGF-I:GH of about 3:1 to 20:1, about 5–7 mg/ml of sodium chloride, about 0.1–3 mg/ml of phenol and/or about 6–10 mg/ml of benzyl alcohol, about 1–3 mg/ml of polysorbate, about 2.5–4 mg/ml of sodium acetate, and about 0.1–1 mg/ml of sodium citrate, pH about 5.4.

The final formulation, if a liquid, is preferably stored at a temperature of about 2°–8° C. for up to about four weeks. Alternatively, the formulation can be lyophilized and provided as a powder for reconstitution with water for injection that is stored as described for the liquid formulation.

IGF-I and GH to be used for therapeutic administration must be sterile. Sterility is readily accomplished by filtration through sterile filtration membranes (e.g., 0.2 micron membranes).

Therapeutic IGF-I and GH compositions generally are placed into a container having a sterile access port, for example, an intravenous solution bag or vial having a stopper pierceable by a hypodermic injection needle.

IGF-I and GH ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous GH solution, and the resulting mixture is lyophilized. The infusion solution is prepared by reconstituting the lyophilized GH using bacteriostatic Water-for-Injection.

It was found that when whole body weight is to be increased without concomitant increases in kidney or thymus weights, the GH+IGF-I formulation is preferably injected. If, however, the object is to affect the body composition of the patient or to increase not only whole body weight but also selected organs such as the thymus and kidney, for example, in patients that are immunodeficient (such as AIDS patients) or in patients with kidney disorders (such as ischemic or nephrotoxic dysfunction or chronic or acute renal insufficiency), the GH+IGF-I formulation is preferably infused to the patient.

The formulation containing both the IGF-I and GH can be made by many different methods. One method comprises mixing an IGF-I-containing composition (having osmolyte, stabilizer, and buffer as described below) with a buffered solution comprising GH at a pH about 6 in a dose (mg) ratio of from about 2:1 to 100:1 IGF-I:GH up to a dose no greater than about 5 mg/ml of GH. Preferably, this buffered solution contains about 1–10 mg/ml of GH in about 5–15 mg/ml of an inorganic salt, about 1–5 mg/ml of a stabilizer, about 1–5 mg/ml of a surfactant, and sodium citrate buffer at pH about 6. More preferably, the liquid GH formulation contains about 3–5 mg/ml GH, about 8–9 mg/ml sodium chloride, about 1–3 mg/ml phenol, about 1–3 mg/ml polysorbate 20, and about 10 mM sodium citrate, pH about 6.

The IGF-I-containing solution useful for administering IGF-I separately from GH and for admixing with the GH solution as described above is as follows: about 2–20 mg/ml of IGF-I, about 2–50 mg/ml of an osmolyte, about 1–15 mg/ml of at least one stabilizer, and a buffer (preferably an acetic acid salt buffer, and most preferably sodium acetate) in an amount such that the composition has a pH of about 5–5.5. The osmolyte, stabilizer, and buffer, and the preferred compounds within these categories are defined above. Optionally, the formulation may also contain a surfactant selected from the types described above, preferably in an amount of about 1–5 mg/ml, more preferably about 1–3 mg/ml.

In a preferred embodiment, the osmolyte is an inorganic salt at a concentration of about 2–10 mg/ml or a sugar alcohol at a concentration of about 40–50 mg/ml, the stabilizer is benzyl alcohol, phenol, or both, and the buffered solution is an acetic acid salt buffered solution. More preferably, the osmolyte is an inorganic salt, most preferably sodium chloride.

In an even more preferred formulation, the amount of IGF-I is about 8–12 mg/ml, the amount of sodium chloride is about 5–6 mg/ml, the stabilizers are benzyl alcohol in an amount of about 8–10 mg/ml and/or phenol in an amount of about 2–3 mg/ml, and the buffer is about 50 mM sodium acetate so that the pH is about 5.4. Optionally, the formulation contains polysorbate as a surfactant in an amount of about 1–3 mg/ml. A 50-mM acetate concentration in the starting IGF-I solution before mixing with GH ensures that the final pH will not vary significantly from 5.4 in the final IGF-I/GH mixture to maintain good solubility of both proteins over a wide mixing ratio range. However, a broader pH range in terms of stability of both proteins is from about 5 to about 6.

The IGF-I formulation of this invention can be used to treat any condition that would benefit from treatment with IGF-I, including, for example, diabetes, chronic and acute renal disorders, such as chronic renal insufficiency, necrosis, etc., obesity, hyperinsulinemia, GH-insufficiency, Turner's syndrome, short stature, undesirable symptoms associated with aging such as increasing lean mass to fat ratios, immuno-deficiencies including increasing CD4 counts and increasing immune tolerance, catabolic states associated with wasting, etc., Laron dwarfism, insulin resistance, and so forth.

This IGF-I formulation especially was found by itself to have increased potency in treating mammals, especially humans, with hyperglycemic disorders by reducing their glucose levels. It was also found to increase the mammal's absorbance of the IGF-I if administered subcutaneously. For purposes herein, "hyperglycemic disorders" refers to all forms of diabetes, such as type I and type II diabetes, as well as hyperinsulinemia and hyperlipidemia, e.g., obese subjects. The preferred disorder is diabetes, especially type II diabetes:

For treating these various conditions, IGF-I is administered by any suitable means, including intravenously, intraperitoneally, subcutaneously, or intramuscularly. The effective amount of IGF-I for this purpose is generally adjusted in accordance with many factors, including the patient's specific disease, the route of administration, the individual weight and general condition of the patient to be treated, and the judgment of the medical practitioner. Caution must be taken to monitor blood glucose periodically to avoid hypoglycemia.

Generally, the dosing will range between about 1 µg/kg/day up to about 100 mg/kg/day, preferably 10 µg/kg/day up to about 10 mg/kg/day. If given continuously, the IGF-I is generally administered in doses of about 1 µg/kg/hour up to about 100 µg/kg/hour, either by two daily injections or by subcutaneous infusions, e.g., via minipump or a portable infusion pump. Preferably, the IGF-I is given subcutaneously or intravenously, and most preferably subcutaneously.

If the IGF-I is administered together with insulin, the latter is used in lower amounts than if used alone, down to amounts which by themselves have little effect on blood glucose, i.e., in amounts of between about 0.1 IU/kg/24 hour to about 0.5 IU/kg/24 hour.

The invention will be more fully understood by reference to the following examples. They should not, however, be construed as limiting the scope of the invention. All literature and patent citations are expressly incorporated by reference.

EXAMPLE I

I. Protocol

Hypophysectomized adult male rats weighing 85 to 105 grams (Taconic, N.Y.) were received 7 days after surgery and then weighed every 2–3 days for ten days to meet entry criteria of a weight gain of less than 7 grams and no overall body weight loss. The rats were maintained on Purina rat chow ad libitum. Each lot of animals was divided into a control (excipient), a IGF-I-supplemented group, a des(1–3)-IGF-I-supplemented group, a GH-supplemented group, a IGF-I/GH-supplemented group, and a des(1–3)-IGF-I/GH-supplemented group.

Alzet osmotic pumps (Alza, Palo Alto, Calif.) were implanted to deliver continuously either excipient (10mM citrate buffer and 126 mM NaCl, pH 6.0) or recombinant human IGF-I (produced in $E.$ $coli$ as a Z—Z fusion polypeptide by the process generally described in EP 230,869 published Aug. 5, 1987, or available commercially from KabiGen AB, Stockholm, Sweden (specific activity>14,000 U/mg by radioreceptor assay using placental membranes), or available for clinical investigations from Genentech, Inc., South San Francisco). The IGF-I was dissolved at 5 mg/ml in 10 mM citrate buffer and 126 mM NaCl, pH 6.0 and delivered to the rats at a rate of 120 µg/rat per day (equivalent to 1.2 mg/kg/day assuming that the rats weigh 100 g each). This rate represents a submaximal dose that gives a consistent body weight gain in this model.

Alternatively, the pumps were implanted to deliver continuously recombinant human des(1–3)-IGF-I (produced in $E.$ $coli$ as generally described by PCT WO 87/01038 published Feb. 26, 1987 and expected to have a specific activity of>about 14,000 U/mg by radioreceptor assay using placenta membranes, or available as brain IGF from KabiGen AB, Stockholm, Sweden, >14,000 U/mg by radioreceptor assay using placenta membranes). It was then formulated at 2 mg/ml in 20 mM acetic acid, pH 3.2, and delivered at a rate of 0.055, 0.166, or 0.5 mg/kg/day.

To the GH-supplemented groups was delivered recombinant methionyl human growth hormone (Protropin® brand, Genentech, Inc., South San Francisco, Calif.) dissolved at 2 mg/ml in 16 mg/ml mannitol and 5 mM phosphate, pH 7.8, as excipient. The hGH was injected subcutaneously each day, also at submaximal doses (15, 60, and 240 µg/kg per day) for the weight gain response. Moore et al., supra.

Alternatively, recombinant (metless) human growth hormone (Nutropin® brand, Genentech, Inc.) may be employed that is formulated at 2 mg/ml in 18 mg/ml mannitol, 0.68 mg/ml glycine, and 5 mM phosphate, pH 7.4.

At pump implant the animals received oxytetracycline in a single intraperitoneal injection as an intravital marker of longitudinal bone growth.

The growth rates of the hypophysectomized animals were determined by following daily body weights, organ weights at sacrifice, and tibial bone fixed for subsequent assessment of the growth plate. The bone was decalcified, bisected longitudinally, and embedded in paraffin for sectioning and staining with toluidine blue. The distance between the germinal cell layer and the transition from active chondrocytes to new bone deposits was measured microscopically with the aid of a calibrated ocular micrometer. In addition, undecalcified sections were prepared from the proximal tibia and the distance between the growth plate and the tetracycline line, laid down in calcified bone, was determined to assess cumulative longitudinal bone growth.

The remaining solution was removed from all osmotic pumps, and verified by immunoassay to contain either excipient, IGF-I, or des(1–3)-IGF-I. Furthermore, the amount of hormones remaining in the pump of each rat was that expected for continuous delivery over seven days at the rate of delivery specified by the manufacturer.

Independent replicate studies are designated as Study 1 and Study 2, performed a month apart. Statistical comparisons were made by an analysis of variance with follow-up comparisons made by Duncan's Multiple Range Test. A p value of less than 0.05 was considered significant. All data are represented as the mean±SD of 6–8 animals per group. Two other independent studies confirmed these data.

II. Results

FIGS. 1A and 1B represent the cumulative daily body weight increments for the hypophysectomized rats treated with either excipient, 60 µg/kg/day hGH, 1.2 mg/kg/day IGF-I, or the hGH/IGF-I combination for seven days for Studies 1 and 2, respectively. The mean±SD of 7–9 animals/group is shown in the graphs; statistical significance was assumed if p<0.05. The excipient control group did not gain or lose a significant amount of weight during the week, confirming the completeness of the hypophysectomy and the health of the animals in both studies. The mean body weight was increased by hGH in a dose-dependent manner such that on days 3–7 the responses to all hGH doses were significantly different from each other (see FIG. 7). Likewise, IGF-I produced a significant body weight gain that was first recognized on day 2 of dosing, and by day 7 was highly significantly different from excipient (2.9±3.5 g vs. 16.6±2.5 g, t=16.86, p<0.001).

The combination of hGH plus IGF-I yielded a body weight gain that was greater than either hormone alone and appeared to be at least additive. By day 7, the body weight increments for the excipient control, IGF-I, hGH, and combination treatments were, respectively: Study 1: 2.91±3.51 g, 16.6±2.5 g, 12.9±1.2 g, and 22.2±2.7 g; Study 2: −0.04±2.41 g, 10.8±3 g, 9.04±0.92 g, and 19.3±1.6 g. The weight increment of the combination group was statistically different from the means of the other three groups. For example, in Study 1 the mean weight gain at day 7 for the combination (22.2±2.7 g) was greater than that for GH alone (12.9±1.2 g, t=10.80, p<0.001) or for IGF-I alone (16.6±2.5 g, t=6.710, p<0.001). In the same experiment (data not shown on this FIG. 1), des-(1–3)-IGF-I also increased weight gain (to 19.9±2.6 g), which on the addition of GH was increased to 24.7±1.3 g (t=5.75, p<0.001).

In contrast, it was reported earlier that when native bovine GH (bGH) was delivered intravenously for four days to hypophysectomized rats, and then bGH plus methionine-IGF-I for four more days, there was no greater weight gain than that measured with bGH alone. Skottner, *J. Endocrin.*, supra. Beyond the different delivery routes and dosing regimens of these two studies, the methionyl-IGF-I itself produced no incremental weight gain in this earlier report. To the contrary, this experiment shows repeatedly that IGF-I and des(1–3)-IGF-I promote body weight gain in hypophysectomized rats and that there was an additive effect when GH was co-delivered.

In the hypophysectomized rat weight gain assay, there is an excellent correlation between the weight gain and the bone growth responses to GH. Therefore, an enhanced weight gain is likely to be accompanied by enhanced bone growth, as is the case below.

FIG. 2 illustrates a bar graph of the increase in width of the epiphyseal bone growth plate after seven days of hGH and/or IGF-I treatment in hypophysectomized rats. The mean±SD for 7–9 rats per group is illustrated for Study 1. Statistically significant differences were assumed if p<0.05.

Figure 3A:
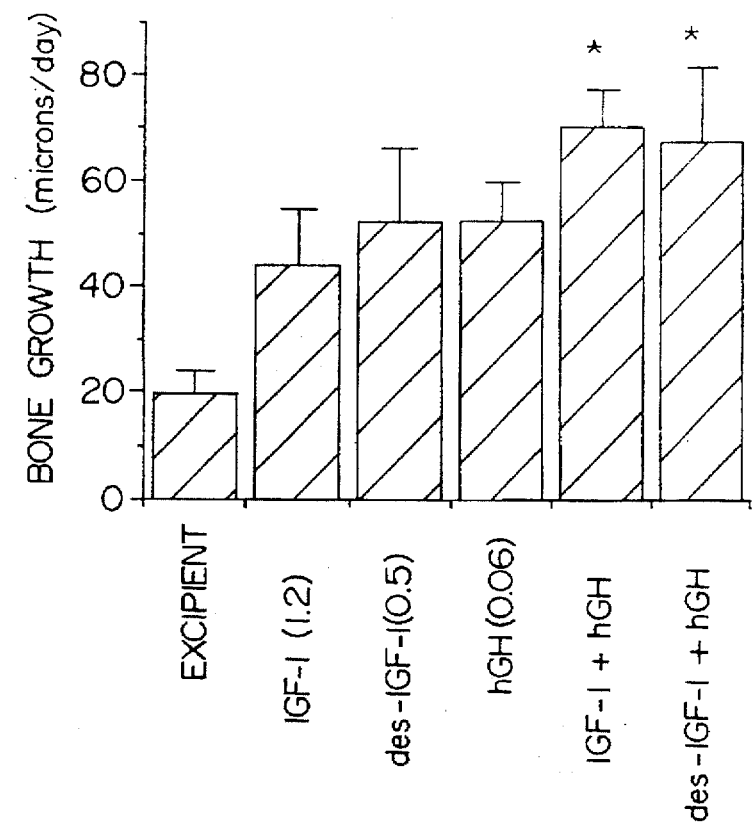
FIGS. 3(A and B) represent graphs of longitudinal bone growth and epiphyseal plate width (a separate study from FIG. 2), respectively, for each group of hypophysectomized rats treated with hGH alone, or IGF-I or des(1–3)-IGF-I alone or in combination with hGH (means±SD).
Figure 3B:
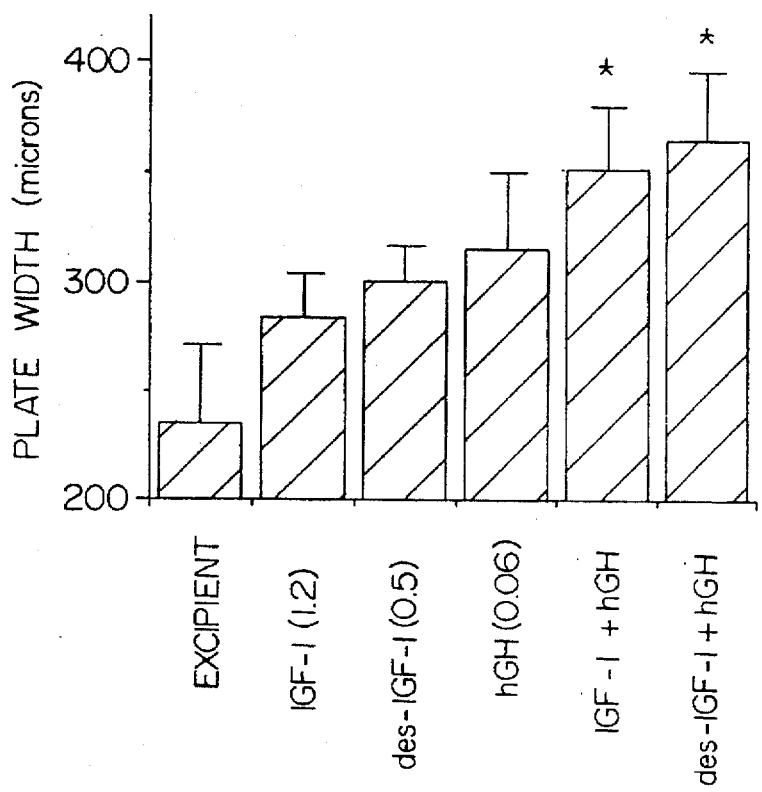

In Study 2, shown in FIG. 3B, the groups treated with 60 μg/kg/day of GH (315±35 μm) or with 120 μg/rat of IGF-I (284±20 μm) were significantly different (t=6.859, p<0.001; t=4.00, p<0.01, respectively) from the excipient group (235±36 μm); the plate width for GH plus IGF-I group (351±29 μm) differed from both the GH alone (t=3.069, p<0.05) and IGF-I alone (t=5.535, p<0.001). Thus, in both studies GH and IGF-I alone induced a significant widening of the tibial epiphysis as compared to the control group, whereas co-treatment with both hormones produced a greater width than treatment with either GH or IGF-I by itself, except at the high-dose GH level. In addition (FIG. 3B), des(1–3)-IGF-I also stimulated growth plate width to 300±17 μm compared to excipient (t=5.545, p<0.001), and once again co-administration of GH resulted in a further increase in plate width to 364±31 μm, which was greater than for des(1–3)-IGF-I alone (t=5,507, p<0.001) and GH alone (t=4.193, p<0.01). The epiphyseal cartilage widening in response to these hormone treatments was similar in pattern to the body weight changes (FIG. 1).

As with body weight gain, other investigators have tested the effects of such combination treatments on tibial bone growth. GH and IGF-I, delivered intravenously to rats by Skottner et al., *J. Endocrin.*, supra, induced no significantly greater response on tibial bone growth or epiphyseal cartilage width than that resulting from treatment with either hormone alone. The IGF-I did induce widening of the epiphyseal cartilage and lengthening of the bone, while having no effect on body weight, as noted above. In another experiment, direct administration of either of these hormones to the tibial epiphysis stimulated longitudinal bone growth. Isgaard et al., supra. However, the combination of IGF-I and GH yielded no greater growth than that achieved with GH alone.

FIG. 3 illustrates two measures of bone growth, longitudinal bone growth (FIG. 3A) and epiphyseal plate width (FIG. 3B, Study 2 as opposed to Study 1 shown in FIG. 2, where only epiphyseal plate width is shown), obtained in hypophysectomized rats treated for 7 days with IGF-I or des(1–3)-IGF-I alone or in combination with hGH. For both full-length IGF-I and des(1–3)-IGF-I, the results show that their combination with hGH yielded bone growth or cartilage expansion that was greater than the effect using either hormone alone and was additive.

The relevant changes in the weights of the five organs measured are as follows (Table 1). While GH inconsistently increased heart, thymus, and spleen, IGF-I and the combination of IGF-I and GH clearly increased all organ weights relative to the excipient group. The preferential effect of IGF-I on kidney, spleen, and thymus has been shown by others. Guler et al., *Proc. Natl. Acad. Sci. USA*, 85: 4889–4893 (1988). A significantly greater effect of the combination treatment was measured only in Study 2, for all organs except the thymus. Correcting for the body weight increment, the organ-to-body weight ratios were increased by IGF-I for kidneys, spleen, and thymus; the hormone combination did not amplify this effect in these three responsive tissues. In contrast, GH treatment did not alter the organ-to-body weight ratios.

These data indicate that at least a fraction of the hormone combination response can be attributed to weight increases in

TABLE 1

GH AND IGF-I ELICIT DIFFERENT ORGAN WEIGHT RESPONSES

| | Excipient | GH 60 ug/kg | IGF-I 1.2 mg/kg | GH + IGF-I |
|---|---|---|---|---|
| A. Absolute Wet Weights | | | | |
| Study 1 | | | | |
| Heart (mg) | 291 ± 20 | 324 ± 13[#] | 341 ± 24[#] | 344 ± 16[#] |
| Kidneys (mg) | 650 ± 46 | 686 ± 60[ab] | 849 ± 50[#a] | 869 ± 31[#b] |
| Liver (g) | 3.80 ± 0.17 | 4.00 ± 0.23[ab] | 4.43 ± 0.27[#a] | 4.44 ± 0.39[#b] |
| Spleen (mg) | 234 ± 56 | 244 ± 26[ab] | 369 ± 50[#a] | 389 ± 54[#b] |
| Thymus (mg) | 233 ± 24 | 317 ± 82[#a] | 391 ± 49[#] | 414 ± 110[#a] |
| Study 2 | | | | |
| Heart (mg) | 355 ± 22 | 374 ± 43[a] | 376 ± 24[b] | 440 ± 65[#ab] |
| Kidneys (mg) | 688 ± 37 | 736 ± 44[ab] | 871 ± 62[#ab] | 973 ± 45[#bc] |
| Liver (g) | 3.77 ± 0.25 | 4.04 ± 0.30[a] | 4.42 ± 0.41[#] | 4.58 ± 0.13[#a] |
| Spleen (mg) | 197 ± 16 | 260 ± 24[#a] | 297 ± 30[#b] | 342 ± 23[#ab] |
| Thymus (mg) | 257 ± 42 | 336 ± 50 | 436 ± 154[#] | 450 ± 113[#] |

TABLE 1-continued

GH AND IGF-I ELICIT DIFFERENT ORGAN WEIGHT RESPONSES

|  | Excipient | GH 60 ug/kg | IGF-I 1.2 mg/kg | GH + IGF-I |
|---|---|---|---|---|
| B. Organ to Body Weight (BW) Ratio (× $10^{-3}$) | | | | |
| Study 1 | | | | |
| Heart/BW | 3.00 ± 0.19 | 3.08 ± 0.17 | 3.10 ± 0.21 | 2.95 ± 0.15 |
| Kidneys/BW | 6.71 ± 0.52 | 6.51 ± 0.57[ab] | 7.70 ± 0.38[#a] | 7.45 ± 0.38[#b] |
| Liver/BW | 39.2 ± 1.8 | 37.9 ± 1.7 | 40.2 ± 2.1 | 38.0 ± 2.2 |
| Spleen/BW | 2.42 ± 0.65 | 2.31 ± 0.27[ab] | 3.35 ± 0.47[#a] | 3.33 ± 0.42[#b] |
| Thymus/BW | 2.41 ± 0.28 | 3.00 ± 0.72 | 3.55 ± 0.97[#] | 3.55 ± 0.97[#] |
| Study 2 | | | | |
| Heart/BW | 3.91 ± 0.22 | 3.72 ± 0.34 | 3.69 ± 0.25 | 3.98 ± 0.51 |
| Kidneys/BW | 7.57 ± 0.27 | 7.33 ± 0.30[ab] | 8.56 ± 0.64[#a] | 8.80 ± 0.37[#b] |
| Liver/BW | 41.4 ± 2.2 | 40.2 ± 1.9 | 43.4 ± 4.2 | 41.4 ± 1.0 |
| Spleen/BW | 2.16 ± 0.13 | 2.69 ± 0.52[#a] | 2.92 ± 0.28[#] | 3.09 ± 0.21[#a] |
| Thymus/BW | 2.83 ± 0.43 | 3.35 ± 0.48 | 4.28 ± 1.48[#] | 4.06 ± 0.99[#] |

Mean ± SD (7–9 rats/group): the # denotes statistically different from excipient and similar letter superscripts denote group differences by Duncan's test after analysis of variance (ANOVA) at p < 0.05 specific organs. In addition, they indicate that the additive effect of IGF-I and GH was not seen on all tissues, for example, for the absolute weight of thymus (Table 1), or for all the organ/body weight ratios. This varying sensitivity of different tissues to the combination of GH and IGF-I was unexpected. In some tissues, notably in whole body growth and on bone and cartilage, IGF-I and GH are both effective and additive. In other tissues, i.e., thymus, IGF-I and GH are both effective but not additive, indicating a selective effect.

EXAMPLE II

A. Combination Studies

In the two experiments described below, hypophysectomized rats as described in Example I (Study 3) or female dwarf rats (60–70 days of age, 100–140 g, Study 4) were anesthetized with ketamine/xylazine. Then 2 (for the dwarf rats) or 2 (for the hypophysectomized rats) osmotic minipumps (Alza 2001, delivery rate 1 μl/hour/pump) were placed subcutaneously. The pumps contained either the excipient (10 mM citrate buffer and 126 mM NaCl, pH 6) or IGF-I (5 mg/ml) so that the approximate dose administered was 240 μg/rat/day (2.4 mg/kg assuming a 100 g rat) for both types of rats. The hGH formulation employed was that described in Example I. The IGF-I was prepared by direct secretion of the IGF-I gene from *E. coli* as in accordance with EP 128,733 published Dec. 19, 1984 or EP 288,451 published Oct. 26, 1988, and expected to have a specific activity of>about 14,000 U/mg by radioreceptor assay using placental membranes, or was obtained from KabiGen AB (specific activity>14,000 U/mg) or from Genentech, Inc. as described in Example I. It was formulated as described in Example I. In Study 3 the solubility of hGH was increased by adding 0.1% Tween 20 to the 5 mM phosphate buffer (pH 7.8). The hGH in both studies was given daily as a single 0.1-ml subcutaneous injection.

In Study 3 (hypophysectomized rats) the experimental groups were:

1) Excipient pump, excipient injections
2) IGF-I pump (2.4 mg/kg), excipient injections
3) Excipient pump, hGH injections (50.0 mg/kg)
4) Excipient pump, hGH injections (10.0 mg/kg)
5) Excipient pump, hGH injections (2 mg/kg)
6) Excipient pump, hGH injections (0.4 mg/kg)
7) Excipient pump, hGH injections (0.08 mg/kg)
8) IGF-I pump (2.4 mg/kg), hGH injections (50.0 mg/kg)
9) IGF-I pump (2.4 mg/kg), hGH injections (10.0 mg/kg)
10) IGF-I pump (2.4 mg/kg), hGH injections (2.0 mg/kg)
11) IGF-I pump (2.4 mg/kg), hGH injections (0.4 mg/kg)
12) IGF-I pump (2.4 mg/kg), hGH injections (0.08 mg/kg).

In Study 4 (dwarf rats) the experimental groups were:

1) Excipient pump, excipient injections
2) IGF-I pump (2.4 mg/kg), excipient injections
3) Excipient pump, hGH injections (2.0 mg/kg)
4) Excipient pump, hGH injections (0.5 mg/kg)
5) Excipient pump, hGH injections (0.125 mg/kg)
6) IGF-I pump (2.4 mg/kg), hGH injections (2.0 mg/kg)
7) IGF-I pump (2.4 mg/kg), hGH injections (0.5 mg/kg)
8) IGF-I pump (2.4 mg/kg), hGH injections (0.125 mg/kg).

Figure 4:
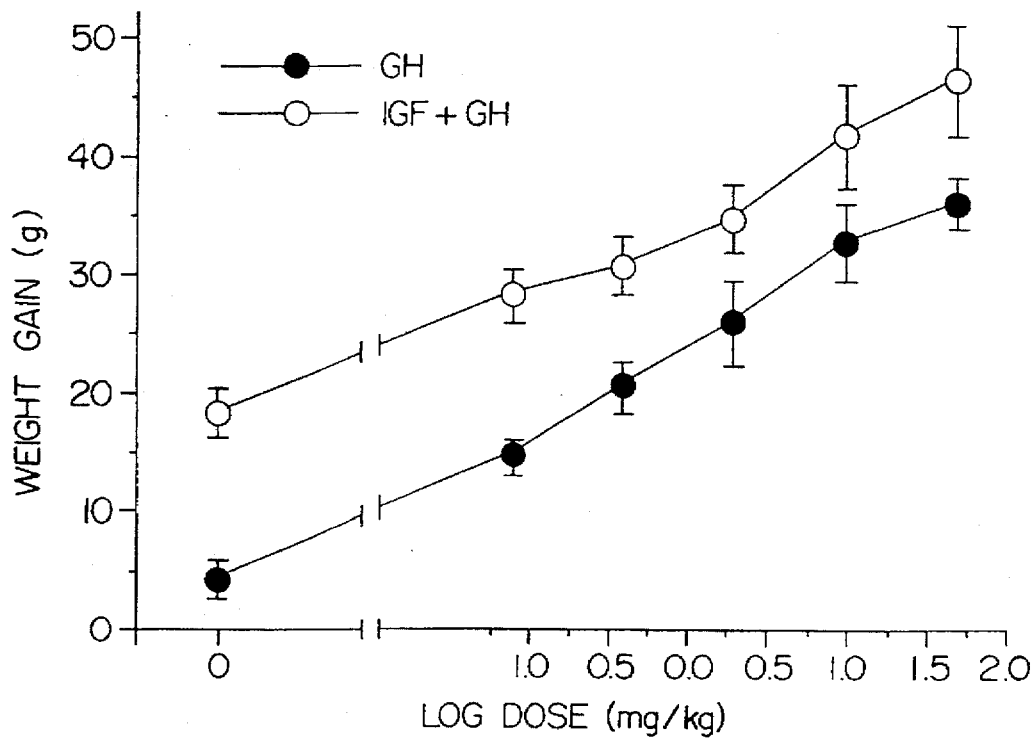
FIG. 4 illustrates a graph of weight gain in hypophysectomized rats over one week as a function of hGH concentration (log dose), where rats were treated with IGF-I (2.4 mg/kg/day) using minipumps and with hGH daily injections (means±SD).

FIG. 4 shows the results from Study 3 for the 7-day weight gains in the hypophysectomized rat. The excipient gave a weight gain of 4.46±1.66 g and IGF-I at 240 μg/day gave a weight gain of 8.23±1.98 g. Once more, the inclusion of IGF-I in the minipumps greatly enhanced the potency of daily injections of hGH in promoting weight gain. The weight gain responses to hGH or hGH plus IGF-I were analyzed as a parallel line bioassay against log dose of hGH. The two dose-response lines fulfilled the criteria for a bioassay, as they were statistically proved to be linear and parallel. The potency of hGH plus IGF-I was 26.6 times that of hGH alone (95% confidence, 14.8 to 51.7), with the difference between the two dose-response lines being highly significant (1,49 degrees of freedom (d.f.), F=169.4, p<0.0001).

Figure 5:
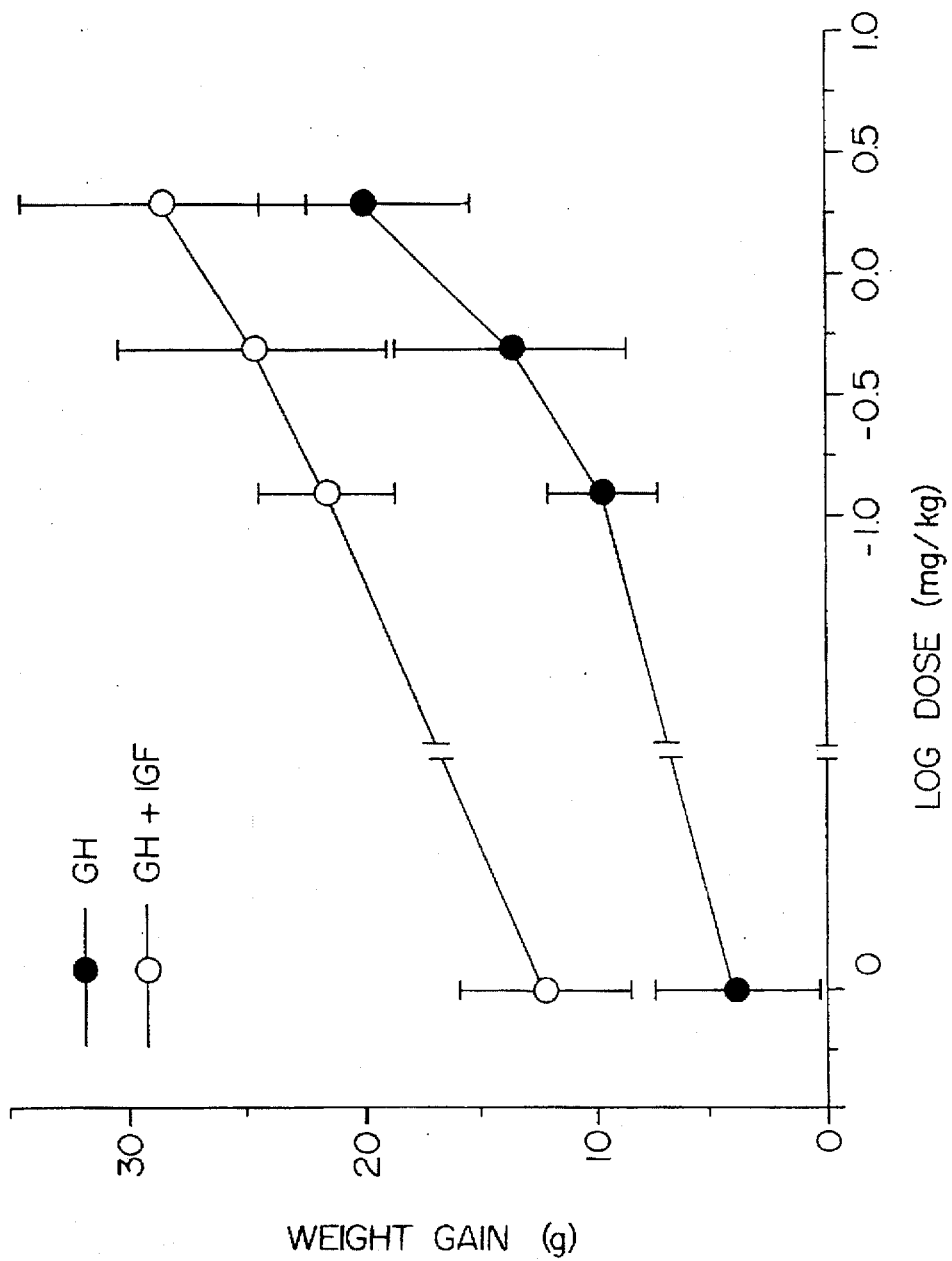
FIG. 5 illustrates a graph of weight gain in dwarf rats over one week as a function of hGH concentration (log dose), where rats were treated with IGF-I (1.2 mg/kg/day) using minipumps and with hGH daily injections (means±SD).

FIG. 5 shows the weight gains over 7 days from Study 4. The excipient gave a weight gain of 3.95±3.56 g and IGF-I at 240 μg/day gave a weight gain of 12.15±3.76 g. The weight gain responses to hGH or hGH plus IGF-I were analyzed as a parallel line bioassay against log dose of hGH. The two dose-response lines fulfilled the criteria for a bioassay, as they were statistically proved to be linear and parallel. Individually, IGF-I and hGH gave substantial weight gains in the dwarf rat. The relative potency of the hGH plus IGF-I was 28.9 times that of the hGH alone (95% confidence limits, 7.7 to 514.6), with the difference between the two dose-response lines being highly significant (1,30 d.f., F=45.75, p<0.0001).

B. Dose Response Curve of IGF-I Alone

Figure 6:
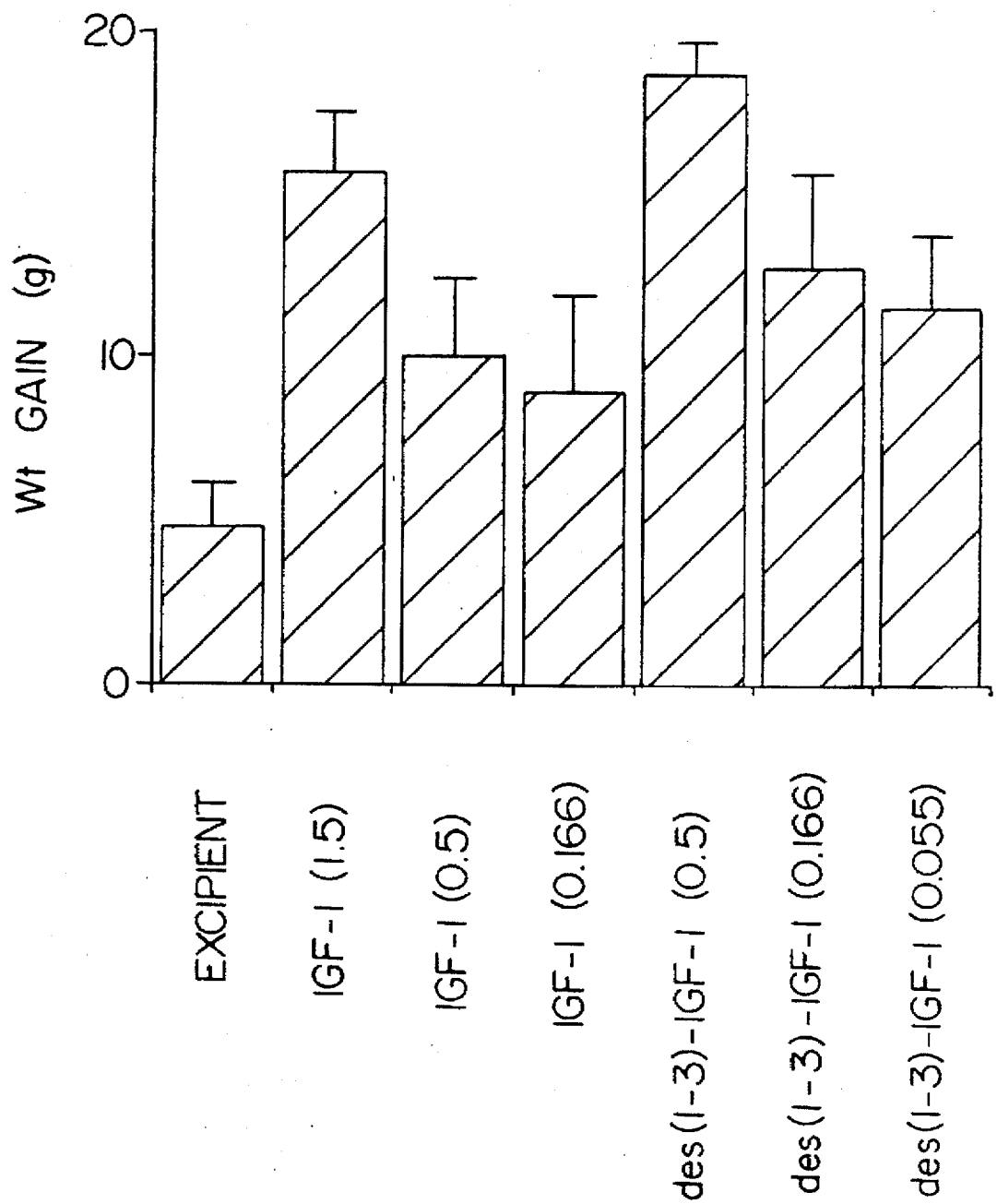
FIG. 6 depicts a graph of weight gain in hypophysectomized rats using three different doses of IGF-I or des(1–3)-IGF-I infused subcutaneously by minipumps for seven days (means±SD).

FIG. 6 illustrates the weight gain of hypophysectomized rats treated with excipient (citrate buffer as described above), or the IGF-I or des(1-3)-IGF-I used in Example I at three different doses subcutaneously using minipumps for seven days, following the general protocol described in Example I. This figure illustrates the minimal doses of IGF-I and des(1-3)-IGF-I for bioactivity in the rat.

C. Dose Response Curve of hGH Alone

Figure 7:
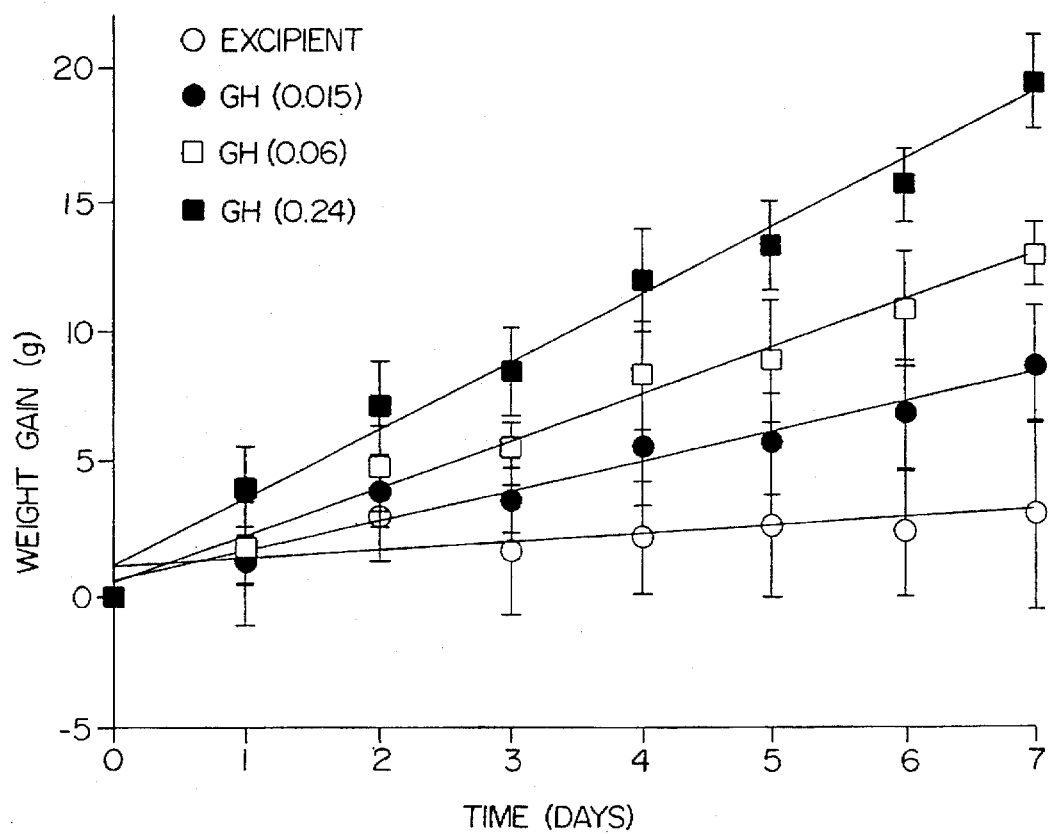
FIG. 7 depicts a graph of weight gain in hypophysectomized rats using three different doses of hGH injected daily subcutaneously for seven days (means±SD).

FIG. 7 illustrates the weight gains of hypophysectomized rats treated with excipient or three different doses of the hGH of Examples I and II daily subcutaneously for seven days, following the general protocol described in Example I. This figure illustrates the minimal doses of GH for bioactivity in the rat. At day 7, low-dose GH showed a greater weight gain than excipient (2.9±3.5 g vs. 8.6±2.3 g, t=7.03, p<0.001), which was in turn less than medium-dose GH (12.9±1.2 g, t=4.91, p<0.01).

In the two animal models of GH deficiency (Studies 3 and 4), the potency of hGH administered as a daily subcutaneous injection was increased over 25 fold by co-treatment with IGF-I. This result in the hypophysectomized rat might be explained by the relative lack of hormones (thyroid and glucocorticoids) known to be permissive for hGH action leading to a poor IGF-I generation. However, the result in the dwarf rat, where only hGH appears to be lacking, with all the other hormone systems (especially the thyroid and adrenal hormones) being normal, indicates that the additive effect of hGH and IGF-I occurs independent of the status of thyroid or adrenal hormones. However, the close agreement in the two models of the enhanced potency of hGH due to IGF-I and the magnitude of the effect (about 25×) is surprising.

The doses of hGH that were used in Study 3 have rarely been used in the hypophysectomized rat, and the literature is unclear as to the dose of hGH that gives a maximal growth response. Doses of 10 and 50 mg/kg/day given as single daily subcutaneous injections for one week produce a maximal growth response. But the dose responses for the two regimes (hGH and hGH plus IGF-I) were parallel, even over this 625-fold dose range of five doses of hGH, including the two maximal doses of hGH. Therefore, the maximal growth response to hGH can clearly be increased if IGF-I is co-administered. This is surprising, as the maximal weight gain response to IGF-I in the hypophysectomized rat appears to be less than the weight gain in response to hGH.

The range of doses of hGH over which IGF-I would be predicted to have an additive effect on weight gain is clearly the full range of effective GH dose, in the hypophysectomized rat from 0.01 to 50 mg/kg. In the dwarf rat the maximal effective doses of hGH are not known, but 50 mg/kg would also be assumed to be an effective maximal dose of hGH. The previous work in the hypophysectomized rat has shown 2.4 mg/kg of IGF-I delivered as a subcutaneous infusion for one week to be near to maximal, as higher doses of IGF-I cause fatal hypoglycemia. The minimal effective dose of IGF-I in the hypophysectomized rat is around 0.1 mg/kg per day.

In the dwarf rat, 2.4 mg/kg of IGF-I was used, while in the hypophysectomized rat both 1.2 mg/kg and 2.4 mg/kg doses of IGF-I were used (Examples I and II), yet an additive effect of IGF-I and GH was observed despite different doses of IGF-I being used. The full dose-response curves for GH alone and GH plus IGF-I were parallel, which implies that at any dose of hGH, even at a very small dose of hGH that by itself might not give a measurable response, the effects of IGF-I and GH would be additive. It would therefore be expected that at any daily dose of GH (from 0.01 to 50 mg/kg) or IGF-I (from 0.1 to 2.4 mg/kg) the two molecules would have additive effects on body growth.

EXAMPLE III

Two Clinical Scenarios for the Combination Treatment

Two examples of pertinent clinical scenarios are described below that will undoubtedly benefit from concomitant administration of GH and IGF-I.

1. Patients who exhibit a slowing in growth rate after at least twelve months of GH administration.

Figure 8A:
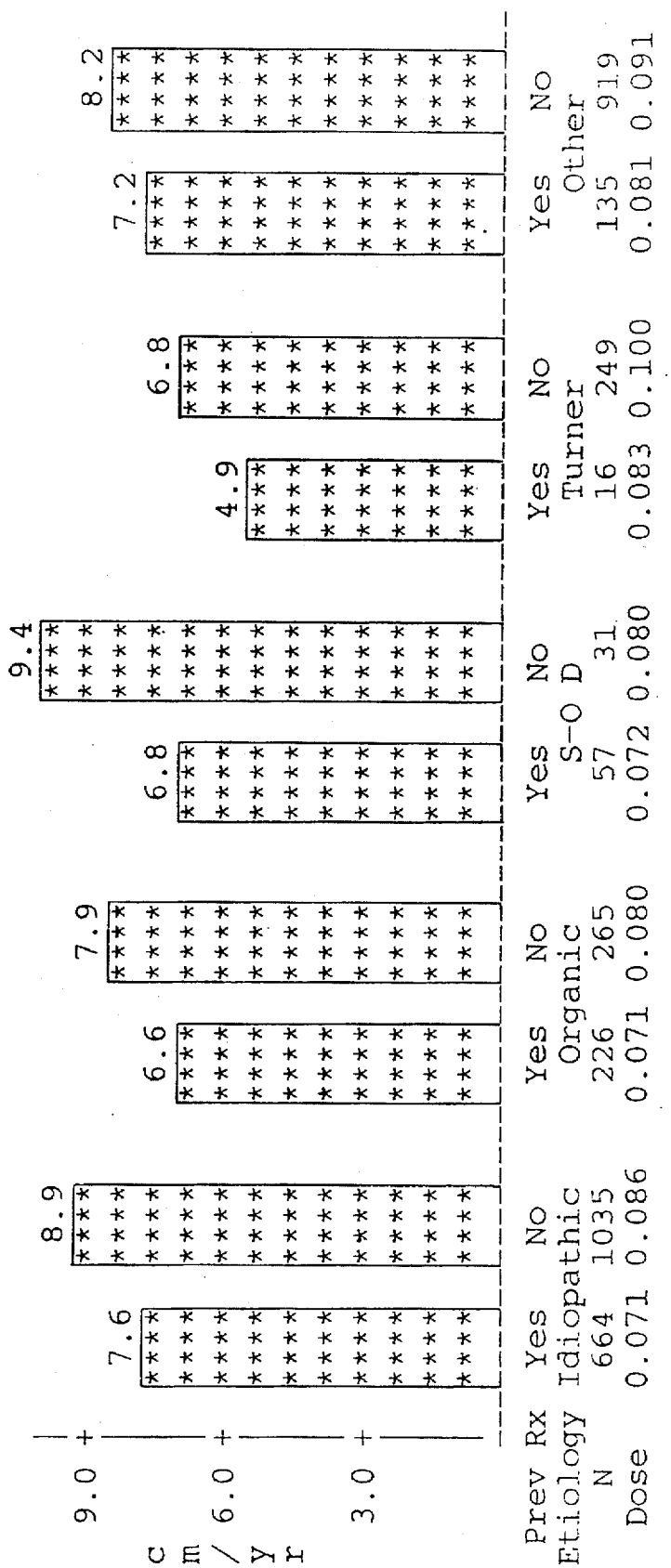
Figure 8B:
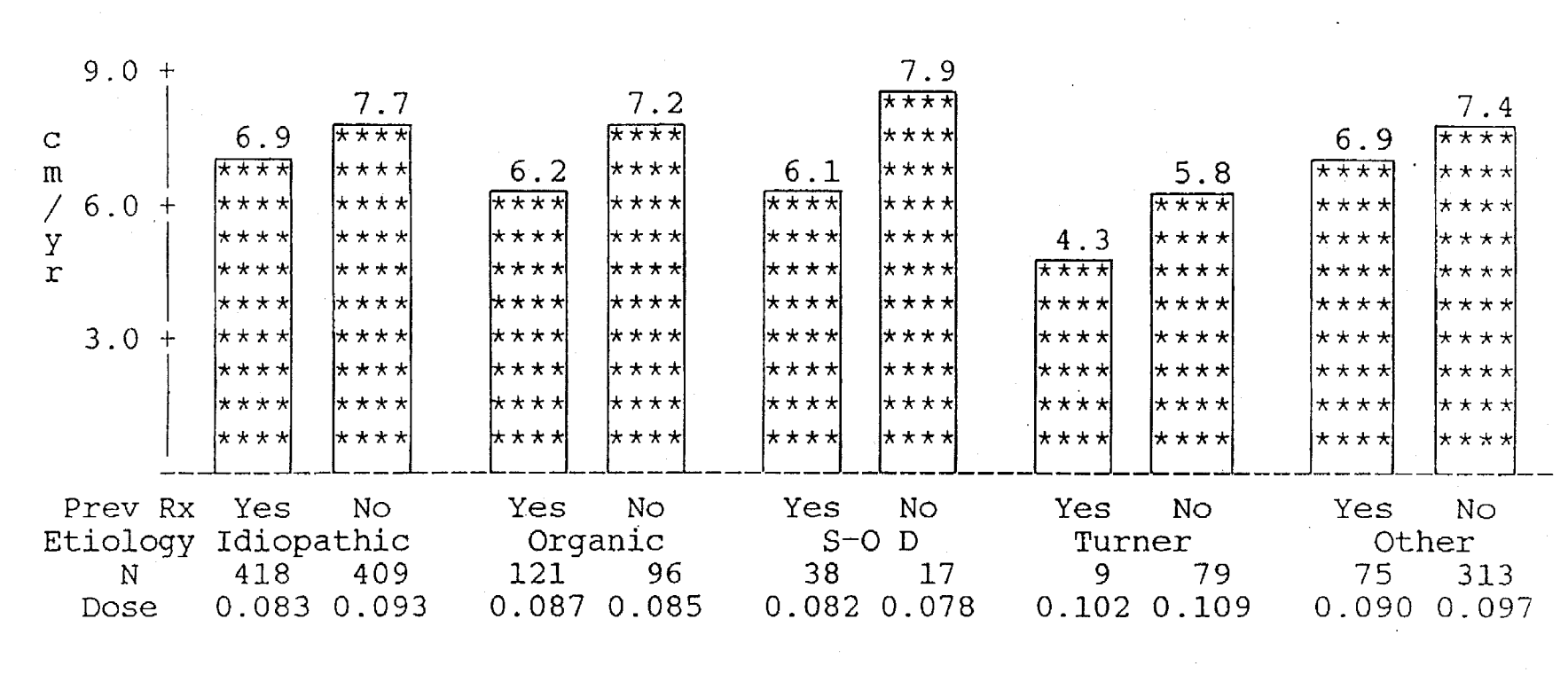

It is well recognized by pediatric endocrinologists that either naive (no previous treatment) or previously treated patients (following a break in GH administration) exhibit a second-year fall in growth rate. This phenomenon is independent of the etiology of the type of short stature or GH deficiency (e.g., whether idiopathic, organic, septo-optic dysplasia (S—O D), Turner, or other). See FIG. 8.

Thus, during the period where the growth rate is slowing, IGF-I treatment together with GH treatment would increase the annualized rate to compensate for this second-year loss in response.

2. Patients who have little time for GH administration to be maximally effective.

Figure 9:
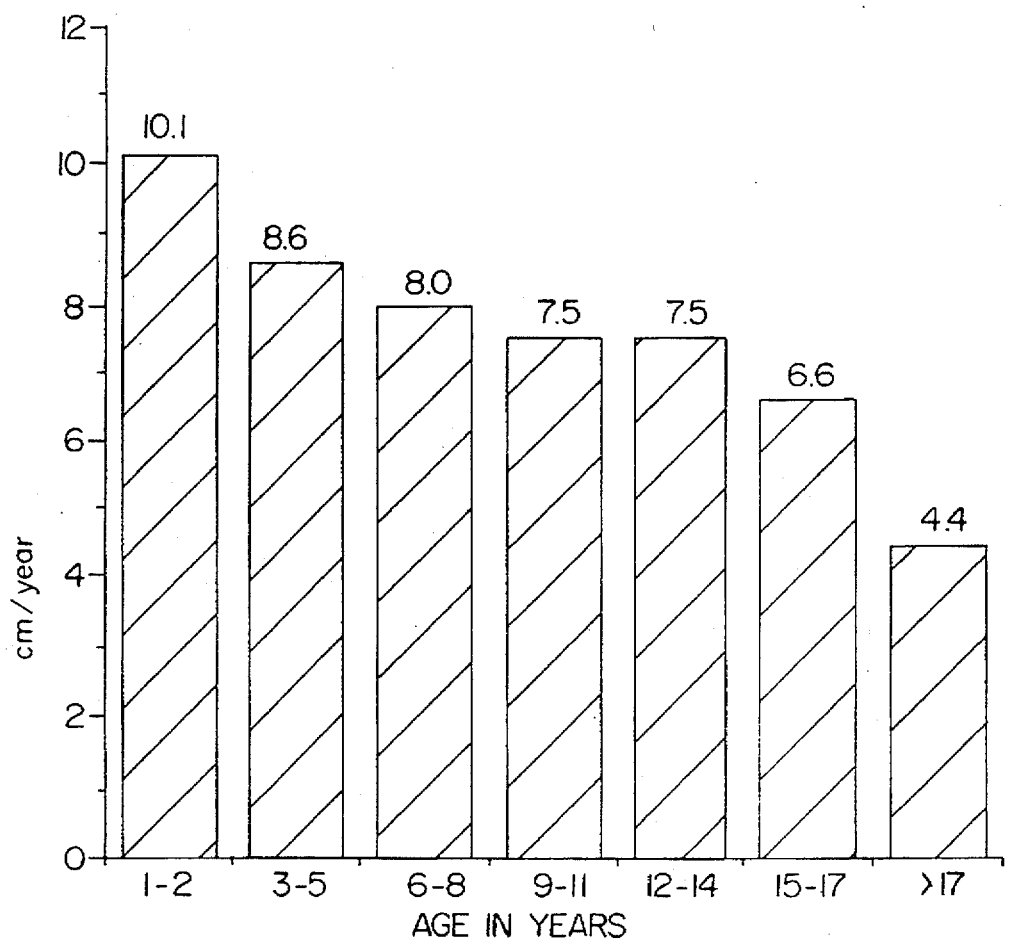
FIG. 9 illustrates bar graphs of the annualized (12-month) growth rate in cm/year of patients treated with the indicated dose of hGH in the 1–2, 3–5, 6–8, 9–11, 12–14, 15–17, and more than 17 year ranges. N indicates the number of patients in each age group.

If patients are older when they are diagnosed with GH deficiency, less time is available to correct their resultant short stature. This is illustrated in FIG. 9, where the annualized growth rate is reported for patients in seven age groups. Older patients have only, for example, 2–3 years left before their growth plates close, making further linear growth unlikely. These patients could be treated with the combination of IGF-I and hGH to allow optimization of their growth rates.

DISCUSSION AND SUMMARY

The results shown herein have significance in medicine and agriculture in any situation where GH or IGF-I treatment is used. This regime of combined IGF-I and GH treatment would allow smaller doses of GH (approximately 25-fold less) to be given to produce equivalent responses to treatment with GH alone. This would be of particular importance in situations where the side effects of GH treatment (i.e., hyperinsulinemia, hyperglycemia) should be minimized. In diabetes, combined GH and IGF-I treatment, with smaller GH doses being possible, would minimize the insulin-resistant effect of the administered GH. In patients where the anabolic effect of GH is reduced, possibly by a reduced ability to produce an IGF-I response to the administered GH, co-treatment with GH and IGF-I would also be expected to give a larger anabolic response.

A broad class of patients where the regime of combined GH and IGF-I treatment would be beneficial is in adult patients where the IGF-I response to GH is naturally reduced. In adults, the unwanted effects of GH (insulin resistance) may be a direct consequence of a reduced IGF-I response to administered GH. In adults, the co-administration of GH and IGF-I might be viewed as restoring the situation in a younger animal where there is a more vigorous IGF-I response to GH treatment.

The mode of administration of the GH in the present studies was intermittent, by daily subcutaneous injection. However, at the largest doses used (50 mg/kg), considerable concentrations of hGH would have persisted in the blood at physiologically effective concentrations, making the blood concentrations of hGH always at a level that would provide a stimulus to GH receptors. Therefore, at the highest dose the tissue exposure to hGH was in essence one of continuous exposure, so that the growth response to administering hGH as a continuous infusion would likely be enhanced by the co-administration of IGF-I. The potency of hGH delivered in any manner that would stimulate body growth or be anabolic would be expected to increase if IGF-I were co-administered. Also, it is likely that the improved potency of co-administered hGH and IGF-I would allow less frequent injections of hGH or IGF-I than for hGH alone.

IGF-I was delivered as a continuous infusion, because previous studies showed that IGF-I given alone as injections is less effective at enhancing body growth. However, the combination of GH plus IGF-I would allow the use of sub-optimal regimes of IGF-I administration, such as injections, when combined with GH treatment.

In conclusion, cotreatment of hypophysectomized or dwarf rats with GH and IGF-I or des(1–3)-IGF-I amplifies the body weight gain, longitudinal bone growth, and tibial epiphyseal widening relative to the response to either hormone alone. This finding indicates for the first time that exogenous IGF-I can increase some growth responses initiated by GH in a manner that is at least additive. Thus, the IGF-I is effective at increasing the responses to GH treatment or at decreasing the amount of GH needed to produce a significant response.

EXAMPLE IV

Preparation of IGF-I Formulation and Combination of IGF-I and GH

It was desired to produce a formulation of IGF-I that could be mixed with hGH in dose ratios of IGF-I:hGH of greater than about 2:1 to provide a stable co-mix of both proteins. In this example, the IGF-I formulation used to achieve this was:

10 mg/ml IGF-I 5.84 mg/ml NaCl 9.0 mg/ml benzyl alcohol 2.0 mg/ml polysorbate 20

50 mM sodium acetate pH 5.4.

The intended final product configuration contained 7 ml (70 mg) of the above solution in a 10-ml glass vial, which is generally stored refrigerated (2°–8° C.) to maximize its lifetime. This product is designed to be a ready-to-use liquid for subcutaneous or intravenous administration using a conventional needle and syringe.

For administration of GH and IGF-I together rather than separately, the above formulation (70 mg IGF-I vial) was mixed with a liquid formulation of hGH (5 mg/ml hGH, 8.77 mg/ml NaCl, 2.5 mg/ml phenol, 2.0 mg/ml polysorbate 20, and 10 mM sodium citrate, pH 6.0), available from Genentech, Inc. The hGH was added up to about 10 mg (2 ml) hGH. The formulations were mixed in dose ratios of 7:1, 14:1, and 28:1 IGF-I:hGH. The resulting formulations were generally stored at 2°–8° C. and used within a two-week period. These final formulations had concentration ranges as follows:

IGF-I 7.1–9.6 mg/ml hGH 0.2–1.4 mg/ml

NaCl 6.0–6.7 mg/ml

Phenol 0.1–0.7 mg/ml

Benzyl alcohol 6.4–8.7 mg/ml

Polysorbate 20 2.0 mg/ml

Sodium citrate 0.1–0.7 mg/ml

Sodium acetate 2.8–3.8 mg/ml

The aim of the metabolic studies reported in Examples V–XIII below was to investigate the hypoglycemic effects of different formulations of recombinant human IGF-I and their pharmacokinetics, alone or in combination with GH, on plasma glucose levels in the anesthetized dwarf (dw/dw) rat or the normal rat. The aim of the growth study reported in Example XIV below was to investigate the anabolic effect of a formulation containing the combination of GH and IGF-I in the dw/dw rat and to compare this effect with that of formulations with either agent alone.

EXAMPLE V

The fall in blood glucose caused by an injection of IGF-I is a rapid response that can be easily measured and can serve as a reasonable bioassay for the "insulin-like" activity, or bioactivity in vivo, of IGF-I.

It had been found in the dw/dw rat that doses of 750 and 250 μg of IGF-I formulated in a citrate buffer at pH 6.0 and given subcutaneously reduced blood glucose by a moderate and maximal amount, respectively. Therefore, in this Example these doses of IGF-I were given.

Experimental Design

Sixteen 11-week-old female dw/dw rats (138–162 g; Simonsen Labs, Gilroy Calif.) were anesthetized using Ketamine (62.5 mg/kg)/Rompun™ Xylazine (12.5 mg/kg) anesthesia, intraperitoneally. An additional dose was given as needed to maintain anesthesia throughout the study. The right jugular vein was cannulated using Microrenathane™ 0.033 OD×0.014 ID (Braintree Scientific, Braintree, Ma.) inserted 23 mm into the jugular. The free end of the cannula was attached to an automated blood sampling machine to collect blood samples at various timepoints.

Four treatment groups, four rats per group, were dosed subcutaneously with one of the four IGF-I formulations below:

A. pH 6.0 formulation of IGF-I (5 mg/ml in 10 mM sodium citrate buffer and 126 mM NaCl, pH 6.0):
 1) 750 μg in 150 μl of solution
 2) 250 μg in 150 μl of solution B. pH 5.0 formulation of IGF-I (10 mg/ml in 20 mM sodium acetate buffer, 2.5 mg/ml (0.25%) phenol, 45 mg/ml mannitol, pH 5.0):
 3) 750 μg in 150 μl of solution
 4) 250 μg in 150 μl of solution Three blood samples were taken before the injections at −15, −10, and −5 minutes; then samples were taken at 20, 40, 60, 80, 100, 120, 150, 180, and 210 minutes post-injection. The plasma was immediately separated by centrifugation. The glucose concentration in the plasma was subsequently determined by a coupled hexokinase procedure using a Monarch 2000 chemical systems instrument. Statistical comparisons were made by an analysis of variance with a Duncan's Multiple Range test. A p value of less than 0.05 was considered as being statistically significant. All data are represented as the mean±standard deviation with four animals per treatment group.

Results

There was considerable variation between animals in their basal blood glucose, but much less variation within an animal for the three initial blood glucose measurements. Therefore, it was decided to express the blood glucose measurements for each individual animal as a percentage of the mean of the three initial pre-injection basal blood glucose values of that animal.

Figure 10:
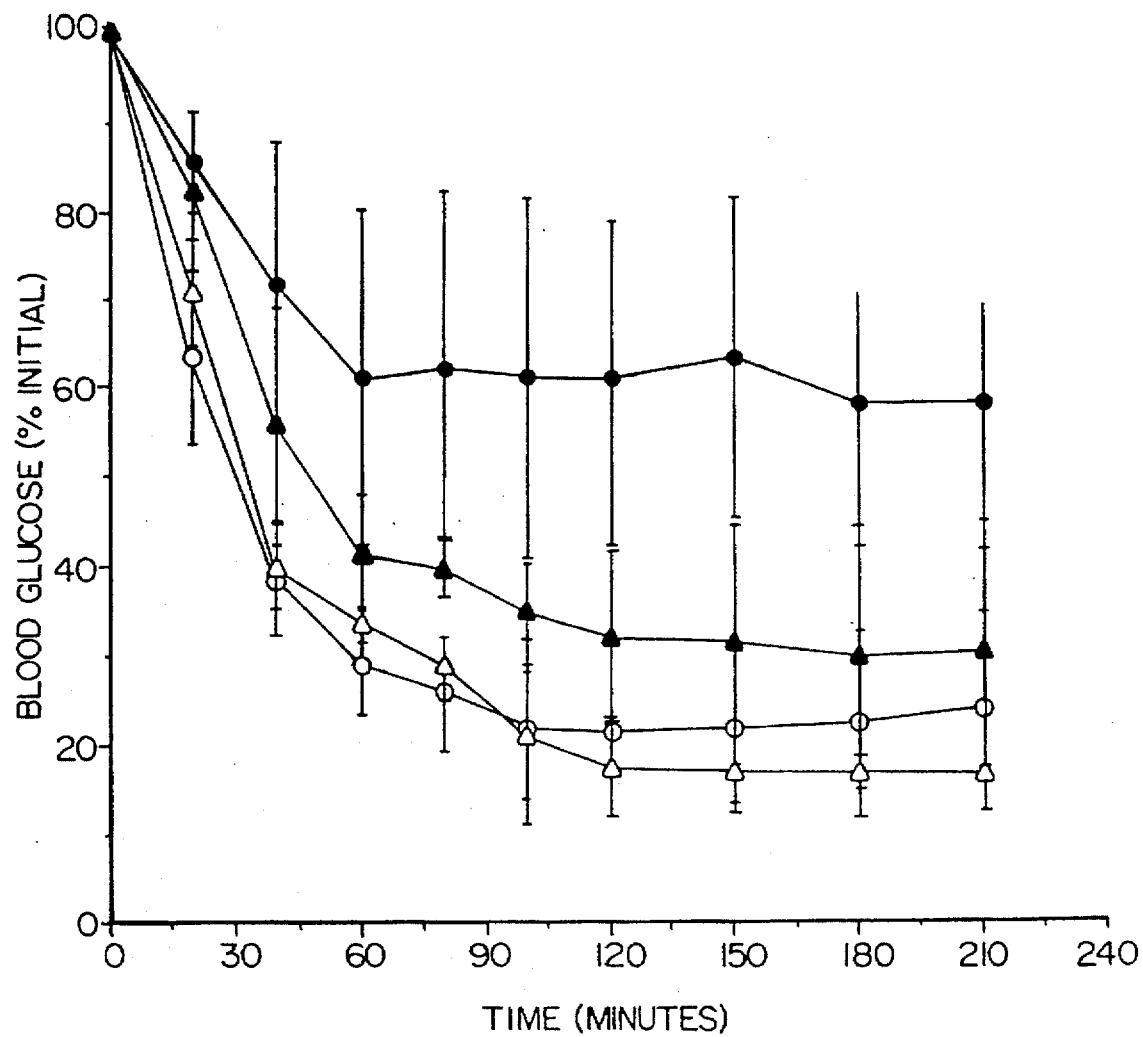
FIG. 10 illustrates the percent change in blood glucose levels with time when either 750 (open) or 250 (filled) µg/rat of IGF-I is given subcutaneously in two different formulations: pH 6.0 citrate (circles) and pH 5.0 acetate (triangles).

FIG. 10 shows the mean percentage changes in blood glucose with time after a subcutaneous injection of IGF-I given at time zero. There was a clear dose-related reduction in blood glucose. The 750-μg dose of IGF-I gave equal decreases in blood glucose for both formulations of IGF-I. However, at the lower dose of IGF-I (250 μg) there was a clear difference between the two preparations of IGF-I that remained statistically significant at each time point from 60 to 210 minutes post-injection. The formulation in sodium acetate at pH 5.0 therefore was more potent.

EXAMPLE VI

In Example V it was found that the re-formulated IGF-I at pH 5.0 appeared to be more potent, as it had a greater effect on blood glucose than the citrate-buffered formulation of pH 6.0. As the response to the 750-μg dose appeared to be maximal, and because the re-formulated IGF-I was more potent, the doses of IGF-I were reduced in this example to 450 and 150 μg/rat.

Experimental Design

Female dw/dw rats (122–138 g) were anesthetized with ketamine/Rompun™ anesthesia, a jugular catheter was inserted, and blood samples were taken as described for Example V.

Four treatment groups, four rats per group, were dosed subcutaneously with one of the four solutions of two IGF-I formulations below:

A. pH 6.0 formulation of IGF-I (5 mg/ml in 10 mM sodium citrate buffer and 126 mM NaCl, pH 6.0):
 1) 450 μg in 150 μl of solution
 2) 150 μg in 150 μl of solution
B. pH 5.0 formulation of IGF-I (10 mg/ml in 20 mM sodium acetate buffer, 2.5 mg/ml phenol, 45 mg/ml mannitol, pH 5.0):
 3) 450 μg in 150 μl of solution
 4) 150 μg in 150 μl of solution Three blood samples were taken before the injections at −15, −10, and −5 minutes; then samples were taken at 20, 40, 60, 80, 100, 120, 150, 180, and 210 minutes post-injection. The experiment was otherwise conducted in an identical manner to Example V.

Results

The blood glucose measurements for each individual animal were expressed as a percentage of the mean of the three initial pre-injection basal blood glucose values of that animal.

Figure 11:
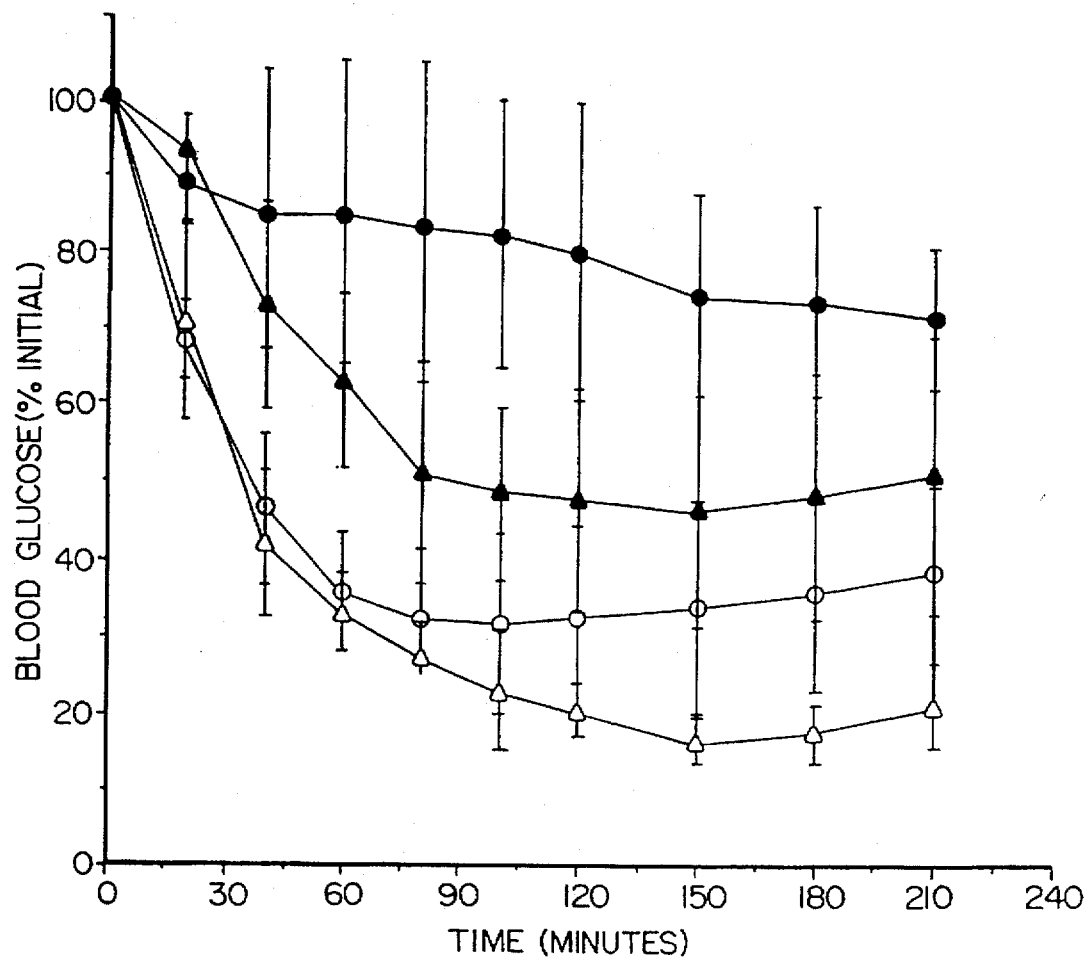
FIG. 11 illustrates the percent change in blood glucose levels with time when either 450 (open) or 150 (filled) µg/rat of IGF-I is given subcutaneously in two different formulations: pH 6.0 citrate (circles) and pH 5.0 acetate (triangles).

FIG. 11 shows the mean percentage changes in blood glucose with time after a subcutaneous injection of IGF-I given at time zero. As in Example V, there was a clear dose-related reduction in blood glucose. The 450-μg dose of IGF-I gave similar initial reductions in blood glucose for both formulations of IGF-I. However, at later time points the blood glucose values for the pH 6.0 formulation at 450 μg rose above those for the pH 5.0 re-formulated IGF-I, although this difference approached but did not reach statistical significance ($p<0.1$). However, at the lower dose of IGF-I (150 μg) there was once more a clear difference between the two preparations of IGF-I that remained statistically significant at each time point from 60 to 210 minutes post-injection.

EXAMPLE VII

In Examples V and VI it was established that the re-formulated pH 5.0 IGF-I had an increased potency over the pH 6.0 formulation. The present example was performed to determine if this increase in potency was due to the IGF-I being better absorbed from the subcutaneous injection site or whether the IGF-I was in some way inherently more bioactive. Both formulations of IGF-I were given as a 150-μl bolus at 150 μg per dose either subcutaneously or intravenously. The intravenous injection was given via the jugular catheter and blood samples were taken as described in Example V.

Experimental Design

Four treatment groups of female dw/dw rats, four rats per group, were dosed as indicated with one of the four solutions of two IGF-I formulations below:

A. pH 6.0 formulation of IGF-I (5 mg/ml in 10 mM sodium citrate buffer and 126 mM NaCl, pH 6.0):
 1) 150 μg in 150 μl of solution subcutaneously
 2) 150 μg in 150 μl of solution intravenously
B. pH 5.0 formulation of IGF-I (10 mg/ml in 20 mM sodium acetate buffer, 2.5 mg/ml phenol, 45 mg/ml mannitol, pH 5.0):
 3) 150 μg in 150 μl of solution subcutaneously
 4) 150 μg in 150 μl of solution intravenously Three blood samples were taken before the injections at −15, −10, and −5 minutes. Then samples were taken at 5, 10, 15, 20, 30, 60, 90, 120, and 150 minutes post-injection, as the instant exposure to an intravenous injection gives more rapid responses than to a subcutaneous injection. The experiment was otherwise conducted in an identical manner to Example V.

Results

The blood glucose measurements for each individual animal were again expressed as a percentage of the mean of the three initial pre-injection basal blood glucose values of that animal.

Figure 12:
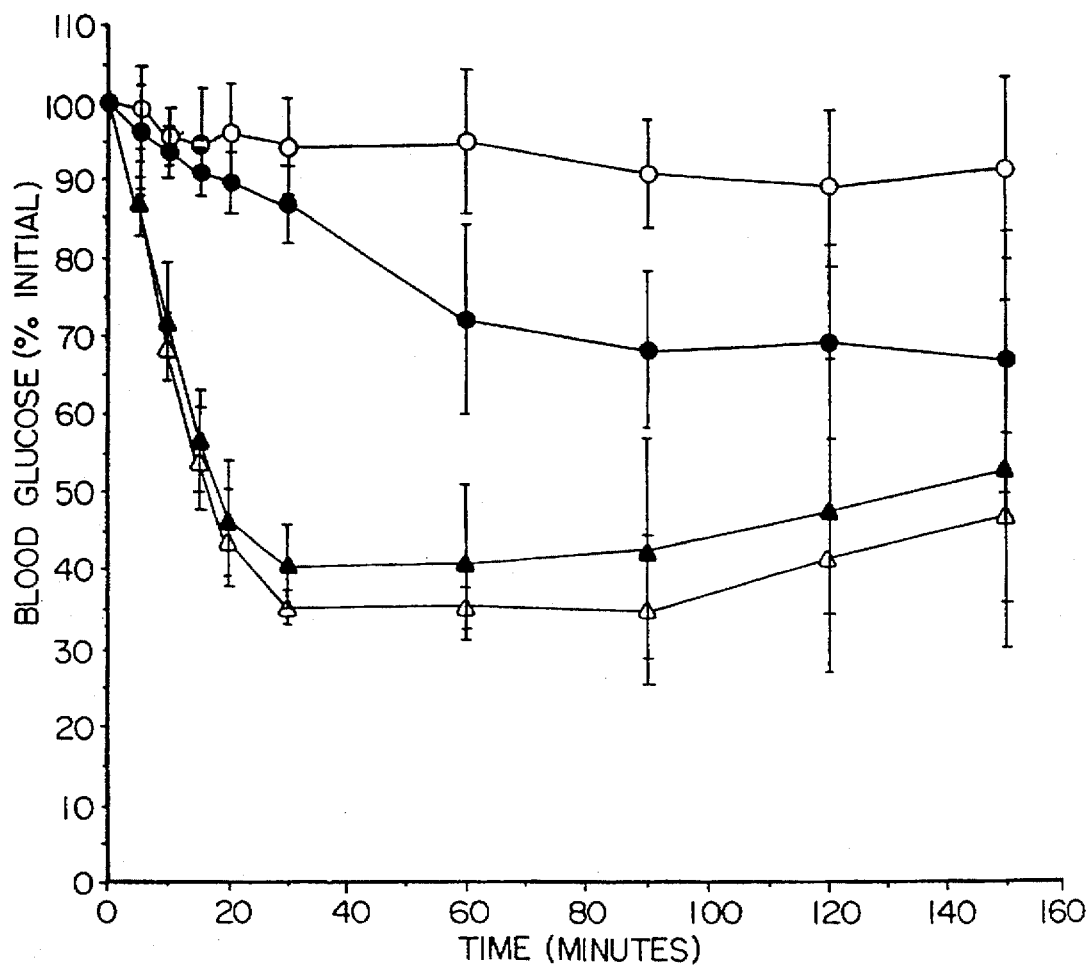
FIG. 12 illustrates the percent change in blood glucose levels with time when 150 µg/rat of IGF-I in either the pH 6.0 citrate formulation (open) or pH 5.0 acetate formulation (filled) is given subcutaneously (circles) or intravenously (triangles).

FIG. 12 shows the mean percentage changes in blood glucose with time after a subcutaneous or an intravenous injection of IGF-I given at time zero. In this experiment the results in Example VI were confirmed, as there was a clear difference between the blood glucose responses to the two formulations given subcutaneously at the 150-μg dose of IGF-I. However, the blood glucose values for the two formulations of IGF-I were nearly identical if they were delivered intravenously.

Therefore, a clear difference was seen in the bioactivity of the IGF-I when given subcutaneously, but little or no difference when it was given intravenously. These data suggest that the difference between the two formulations was primarily an effect on the amount, or nature, of the IGF-I absorbed into the blood from the site of subcutaneous injection.

EXAMPLE VIII

In Examples V–VII it was established that the pH 5.0 re-formulated IGF-I had increased potency when given by subcutaneous injection, and that this was probably related to an increased absorption of the IGF-I in the pH 5.0 formulation. The present example questions whether this increase in potency was due to the IGF-I being better absorbed from the subcutaneous injection site at the lower pH (6 versus 5). Therefore, the pH 6.0 formulation of IGF-I in citrate buffer, but at low pHs (dose 150 μg), was given subcutaneously. Blood samples were taken as described in Example V.

Experimental Design

Four treatment groups of female dw/dw rats, four rats per group, were dosed subcutaneously with one of the four solutions of two IGF-I formulations below:

A. pH 6.0 formulation of IGF-I (5 mg/ml in 10 mM sodium citrate buffer and 126 mM NaCl, pH 6.0):
   1) 450 µg in 150 µl of solution
   2) 150 µg in 150 µl of solution
B. pH 5.0 formulation of IGF-I (5 mg/ml in 10 mM sodium citrate buffer and 126 mM NaCl, pH 5.0):
   3) 450 µg in 150 µl of solution
   4) 150 µg in 150 µl of solution Three blood samples were taken before the injections at −15, −10, and −5 minutes; then samples were taken at 20, 40, 60, 80, 100, 120, 150, 180, and 210 minutes. The experiment was otherwise conducted in an identical manner to Example V.

Results

The blood glucose measurements for each individual animal were again expressed as a percentage of the mean of the three initial pre-injection basal blood glucose values of that animal.

Figure 13:
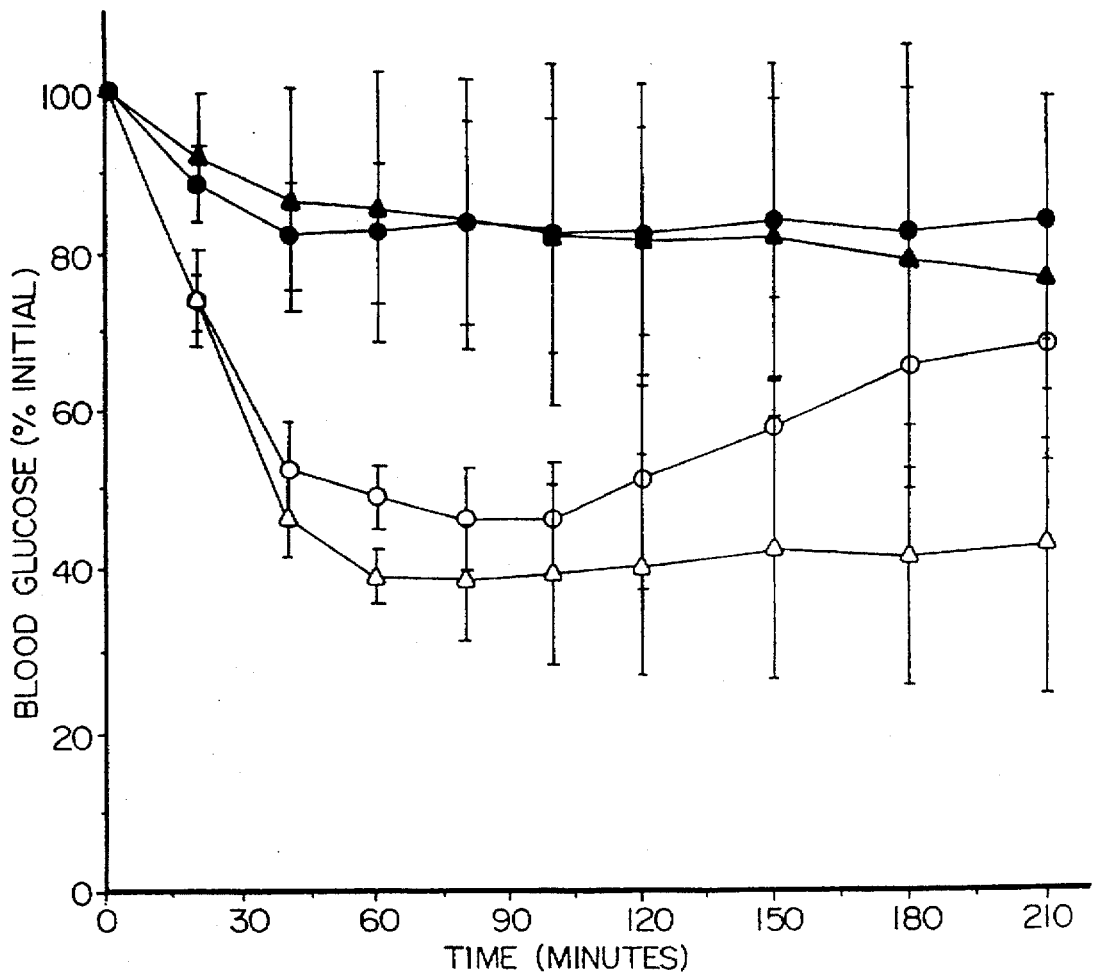
FIG. 13 illustrates the percent change in blood glucose levels with time when either 450 (open) or 150 (filled) µg/rat of IGF-I is given subcutaneously in two different formulations: pH 6.0 citrate (circles) and pH 5.0 citrate (triangles).

FIG. 13 shows the mean percentage changes in blood glucose with time after a subcutaneous injection of IGF-I given at time zero. In this experiment there was no clear difference between the blood glucose responses to the two formulations given at the 150-µg dose of IGF-I. However, the blood glucose values for the two formulations of IGF-I given at the 450-µg dose appeared to be different at later time points: this difference approached statistical significance ($p < 0.1$).

Thus, some evidence was obtained showing that a difference in pH between IGF-I formulations could affect the absorption of IGF-I. However, changing the pH of the citrate-buffered formulation from pH 6 to pH 5 did not produce the large difference in potency that was seen between the two formulations of IGF-I in Examples V–VII. Therefore, the absorption of IGF-I from the pH 6.0 formulation can unexpectedly be improved by a combination of pH and formulation changes.

EXAMPLE IX

In Examples V–VIII it was established that a re-formulation of IGF-I could change its bioactivity. In this example, a new formulation of IGF-I is devised that can be co-mixed with hGH. The bioactivity of this new IGF-I formulation is tested to assess the effects of a different pH (5.4) and different additives and ions.

The design of Example VII was repeated to discover if there was an increased potency of the pH 5.4 formulation given subcutaneously and if this was due to the IGF-I being better absorbed from the subcutaneous injection site or whether the IGF-I was in some way inherently more bioactive (tested by intravenous injection). Both formulations of IGF-I were therefore given at one dose (150 µg) either subcutaneously or intravenously. The intravenous injection was given via the jugular catheter and blood samples were taken as described in Example V.

Experimental Design

Four treatment groups of female dw/dw rats, four rats per group, were dosed as indicated with one of the two IGF-I formulations below:

A. pH 6.0 formulation of IGF-I (5 mg/ml in 10 mM sodium citrate buffer and 126 mM NaCl, pH 6.0):
   1) 150 µg in 150 µl of solution subcutaneously
   2) 150 µg in 150 µl of solution intravenously
B. pH 5.4 formulation of IGF-I (10 mg/ml in 50 mM sodium acetate buffer, 2.5 mg/ml phenol, 5.84 mg/ml NaCl, and 9 mg/ml benzyl alcohol, pH 5.4):
   3) 150 µg in 150 µl of solution subcutaneously
   4) 150 µg in 150 µl of solution intravenously Blood samples were taken before the injections at −15, −10, and −5 minutes; then samples were taken at 10, 20, 30, 45, 60, 90, and 120 minutes. The experiment was otherwise conducted in an identical manner to Example V.

Results

The blood glucose levels for each individual animal were expressed as a percentage of the mean of the three initial pre-injection basal blood glucose values of that animal.

Figure 14:
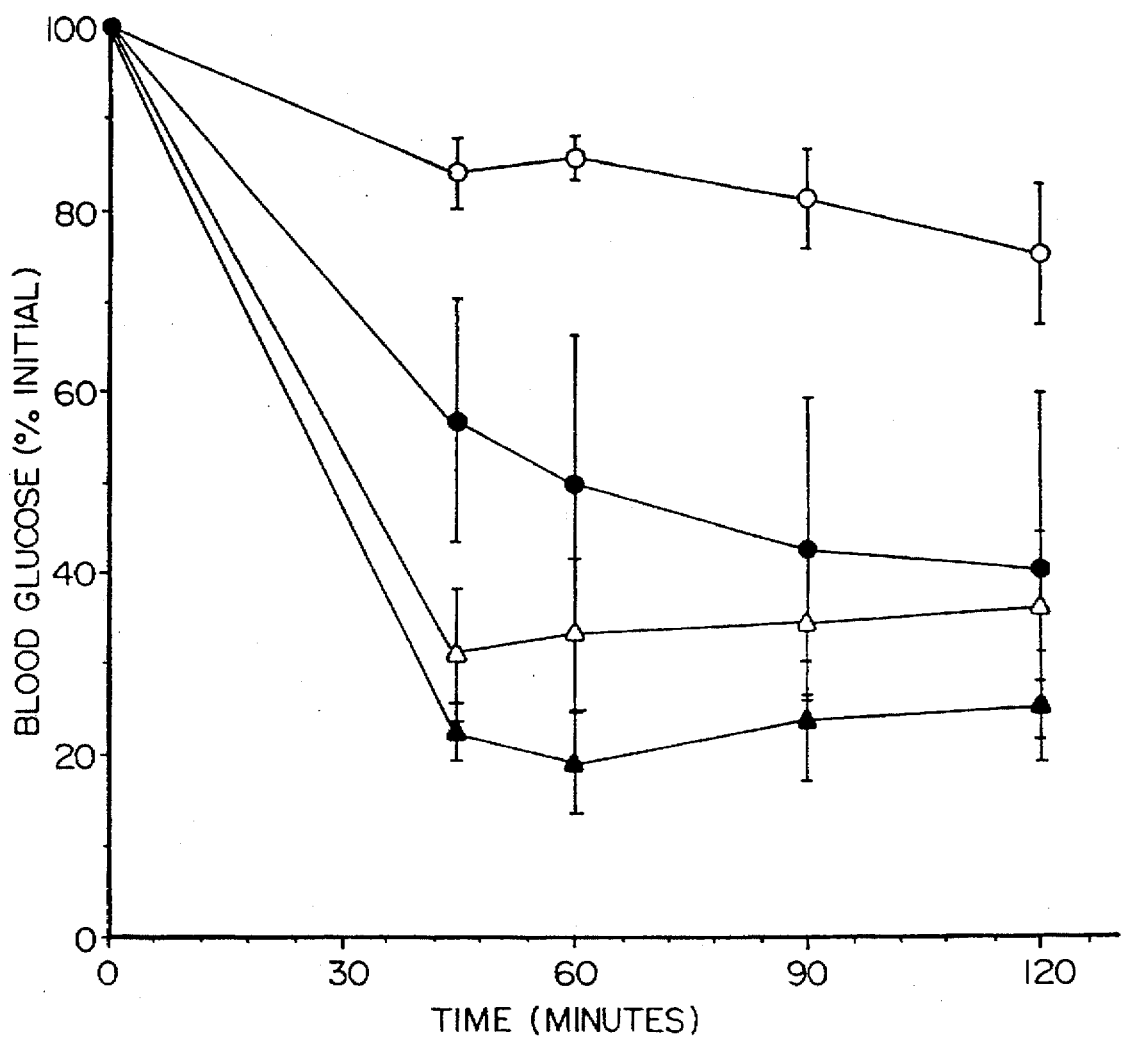
FIG. 14 illustrates the percent change in blood glucose levels with time when 150 µg/rat of IGF-I in either the pH 6.0 citrate formulation (open) or pH 5.4 acetate formulation (filled) is given subcutaneously (circles) or intravenously (triangles).

FIG. 14 shows the mean percentage changes in blood glucose with time after a subcutaneous injection of IGF-I given at time zero. In this experiment samples at 10, 20, and 30 minutes were lost, due to overdilution, so only the data from 45 minutes onward is shown. In this example, there was a clear difference between the blood glucose responses to the two formulations given subcutaneously at the 150-µg dose of IGF-I. However, the blood glucose values for the two formulations of IGF-I given intravenously at the 150-µg dose were not significantly different. It can also be seen that the response at 120 minutes for the subcutaneously delivered pH 5.4 formulation IGF-I approached that of the intravenously delivered dose.

Therefore, the pH 5.4 IGF-I formulation also was very well absorbed compared to the pH 6.0 formulation of IGF-I. A comparison of FIGS. 12 and 14 indicates that the pH 5.4 formulation used in the present study was probably superior to the pH 5.0 formulation used in Example VII. Changing the pH of the formulation from pH 6 to pH 5.4 and changing the components of the formulation unexpectedly led to marked increases in biopotency.

EXAMPLE X

This example repeats the design of Example IX to attempt to duplicate the results showing an increased potency of the pH 5.4 formulation given subcutaneously but a similar effectiveness when given intravenously. Therefore, both formulations of IGF-I were given at one dose (150 µg) either subcutaneously or intravenously. The intravenous injection was given via the jugular catheter and blood samples were taken as described in Example V.

Experimental Design

Four treatment groups of female dw/dw rats, four rats per group, were dosed with one of the two IGF-I formulations below:

A. pH 6.0 formulation of IGF-I (5 mg/ml in 10 mM sodium citrate buffer and 126 mM NaCl, pH 6.0):
   1) 150 µg in 150 µl of solution subcutaneously
   2) 150 µg in 150 µl of solution intravenously
B. pH 5.4 formulation of IGF-I (10 mg/ml in 50 mM sodium acetate buffer, 2.5 mg/ml phenol, 5.84 mg/ml NaCl, and 9 mg/ml benzyl alcohol, pH 5.4):
   3) 150 µg in 150 µl of solution subcutaneously
   4) 150 µg in 150 µl of solution intravenously Blood samples were taken before the injections at −15, −10, and −5 minutes; then samples were taken at 10, 20, 30, 60, 90, and 120 minutes. The experiment was otherwise conducted in an identical manner to Example V. However, in addition to blood glucose levels, the plasma IGF-I concentration was measured to determine directly its absorption and clearance from the blood. The IGF-I concentration in the plasma samples was measured after acid-ethanol extraction to remove the IGF binding proteins) by radioimmunoassay.

Results

Figure 15:
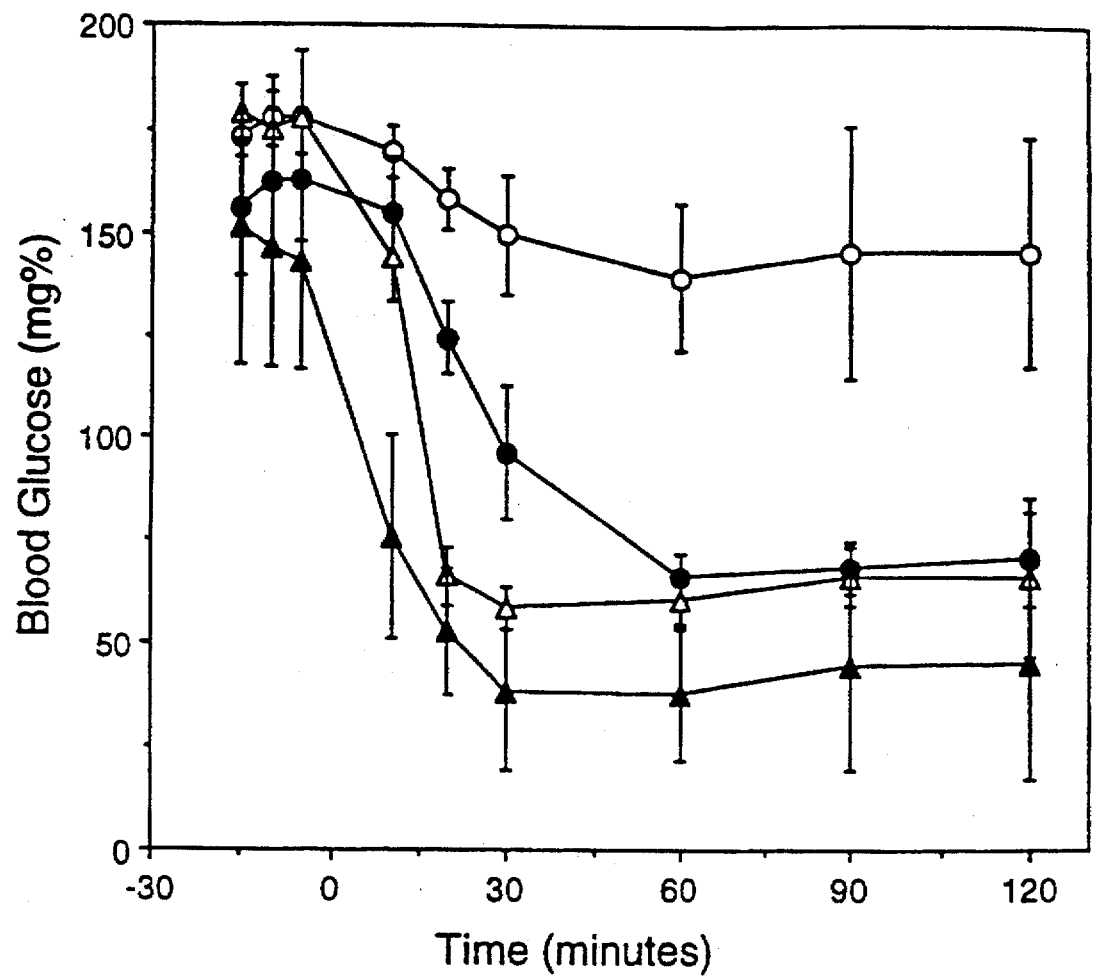
FIG. 15 shows the absolute glucose levels (mg %) when 150 µg/rat of IGF-I is given in four different formulations: pH 6.0 citrate, administered subcutaneously (open circles), pH 5.4 acetate, administered subcutaneously (filled circles), pH 6.0 citrate, administered iv (open triangles), and pH 5.4 acetate, administered iv (filled triangles).
Figure 16:
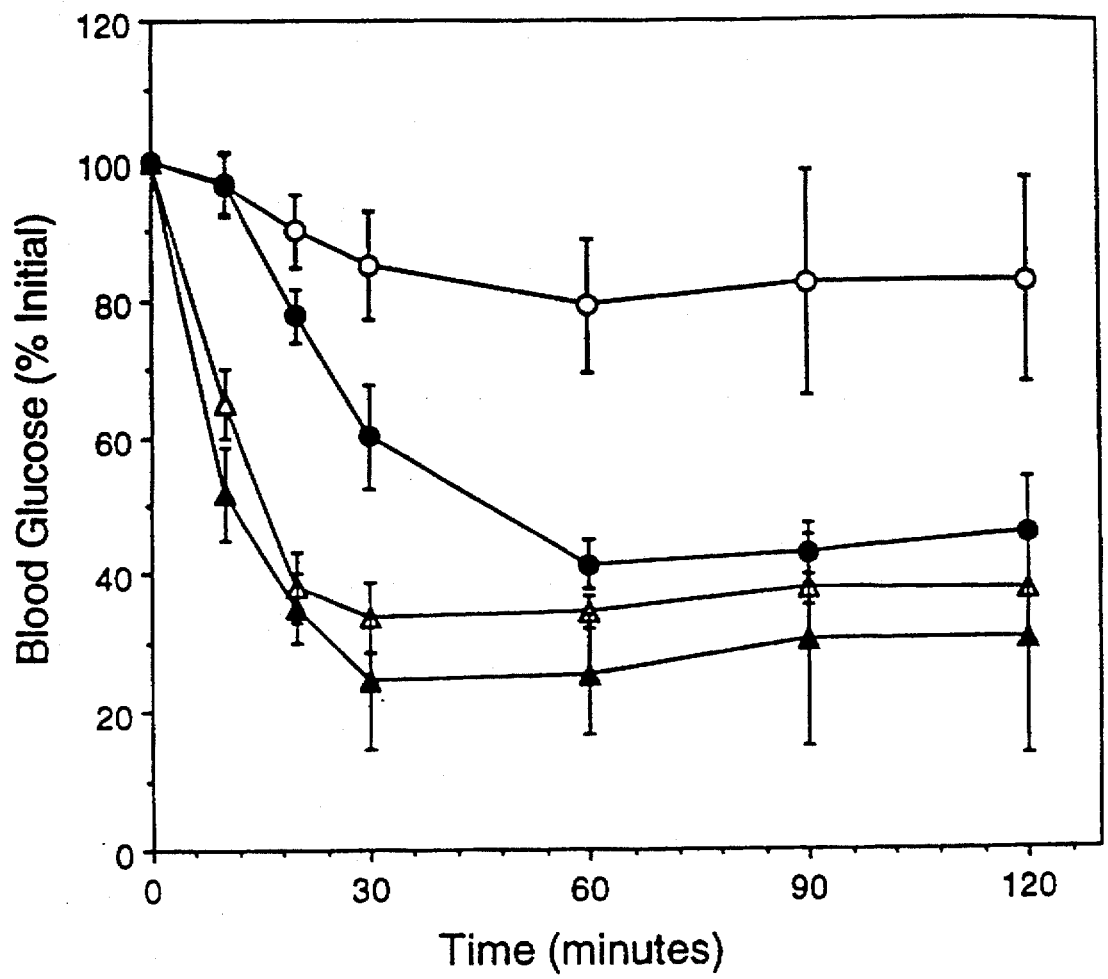
FIG. 16 shows the percent change in blood glucose levels with time using the four different formulations, with the symbols being the same as for FIG. 15.

This example shows the absolute (FIG. 15) and the mean percentage (FIG. 16) changes in blood glucose with time after subcutaneous or intravenous injections of IGF-I given at time zero. A clear difference existed between the blood glucose responses to the two formulations given subcutaneously at the 150-µg dose of IGF-I. However, the blood glucose values for the two formulations of IGF-I given intravenously at the 150-µg dose were not significantly different. It can also be seen that the response at 60 minutes for the subcutaneously delivered pH 5.4 IGF-I formulation approached that of the intravenous dosing.

Figure 17:
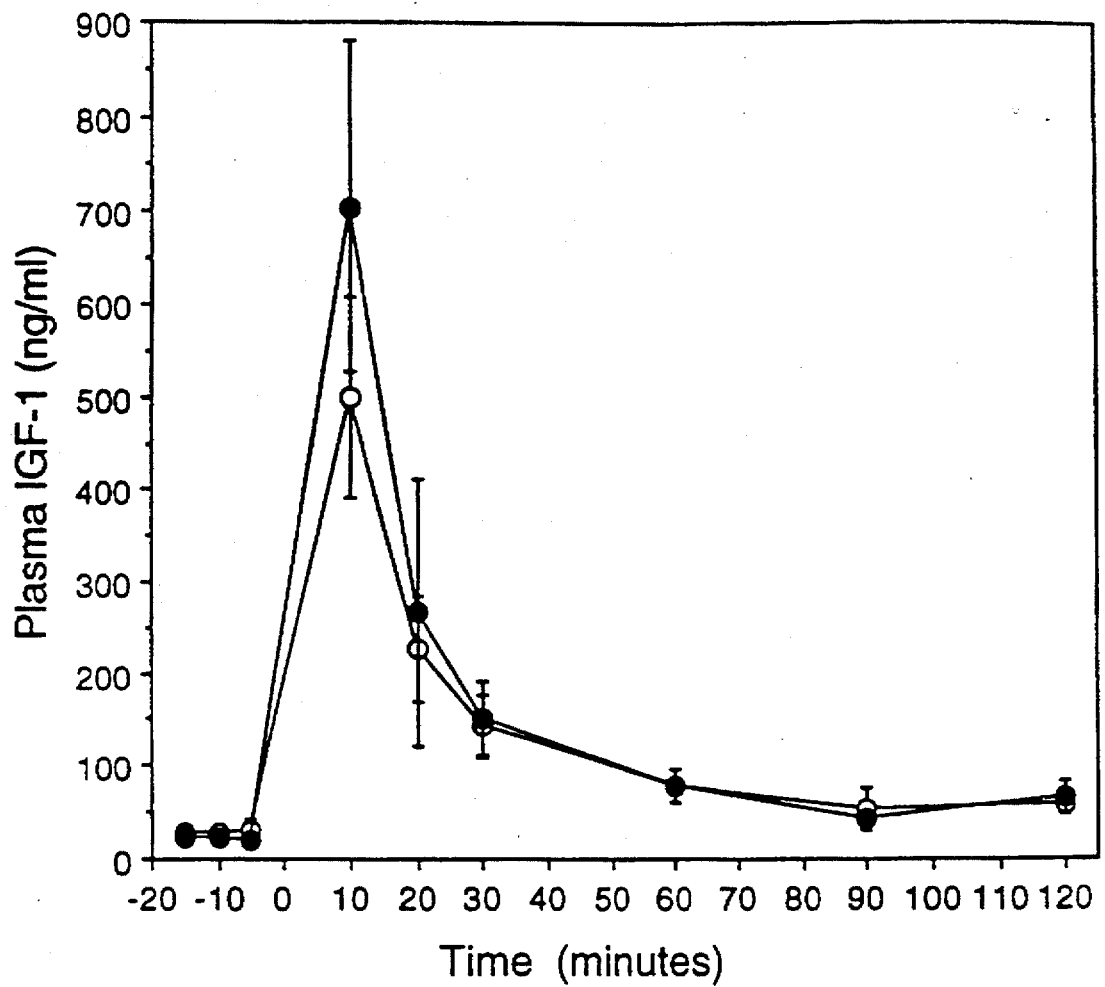
FIG. 17 shows the level of plasma IGF-I (ng/ml) versus time after injection of IGF-I (150 µg/rat iv) using either pH 6.0 citrate formulation (open circles) or pH 5.4 acetate formulation (filled circles).
Figure 18:
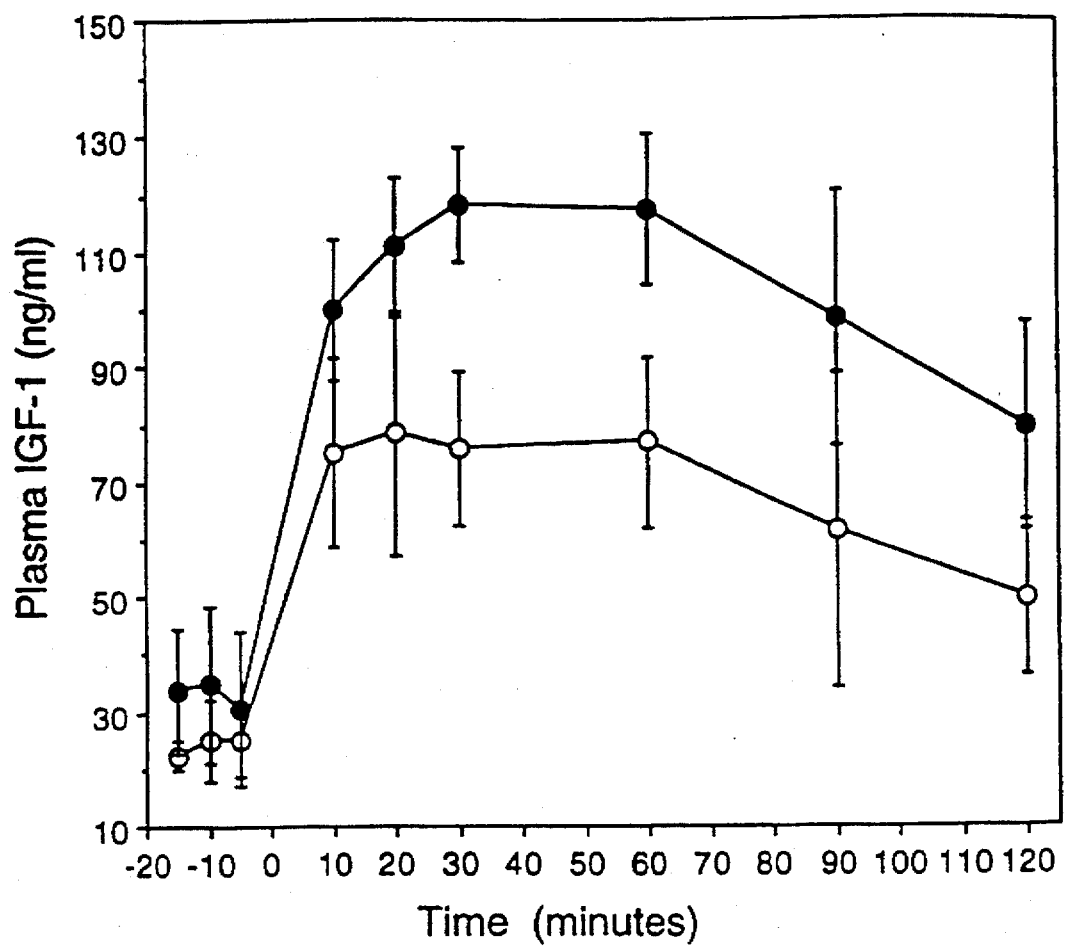
FIG. 18 is the same as FIG. 17 except that the IGF-I was administered subcutaneously instead of intravenously.

Also shown are the plasma IGF-I concentrations after intravenous (FIG. 17) or subcutaneous (FIG. 18) injections of IGF-I given at time zero. There was a clear difference between the plasma IGF-I concentrations for the two formulations given subcutaneously. The concentration of IGF-I was increased by about 40 ng/ml (from about 30 to about 70 ng/ml) by the pH 6.0 formulation, but was increased by about 80 ng/ml (from about 30 to about 110 ng/ml) by the pH 5.4 formulation. However, the plasma IGF-I concentrations for the two formulations of IGF-I (FIG. 17) given intravenously were not significantly different.

This experiment confirmed and extended the results of Example IX. Once again, the pH 5.4 IGF-I formulation was very well absorbed compared to the pH 6.0 formulation of IGF-I. The improved absorption is now directly shown, as the plasma IGF-I concentrations were doubled when the same dose of IGF-I was given subcutaneously in the pH 5.4 formulation. The pH 5.4 formulation of IGF-I gave a hypoglycemic response that was nearly identical to that of the same dose of IGF-I given intravenously. These data suggest that the IGF-I delivered in the pH 5.4 formulation is nearly 100% bioavailable to the rat. These data confirm that the absorption of IGF-I from the pH 5.4 formulation is unexpectedly improved over that from the pH 6.0 formulation by a combination of pH and formulation changes.

Summary

By measuring the hypoglycemic response to intravenous and subcutaneous dosing of the two formulations of the IGF-I, it may be concluded that:

1. The pH 5.4 formulation is more potent and better absorbed than the pH 6.0 formulation when given subcutaneously.
2. The two formulations give statistically equivalent hypoglycemic responses-when dosing is intravenous.
3. There is a suggestion that the mean fall in blood glucose is greater with the pH 5.4 formulation even with intravenous dosing, although this does not reach statistical significance.

EXAMPLE XI

In Example X it was established that the re-formulated pH 5.4 IGF-I had an increased potency when given by subcutaneous injection. This example was designed to determine the relative potency of the two preparations of IGF-I by giving two doses of IGF-I by subcutaneous injection and measuring hypoglycemia and the serum IGF-I concentrations. It appeared that the pH 5.4 formulation was about 3-fold more effective as a hypoglycemic agent than the pH 6.0 formulation. Therefore, the pH 6.0 formulation of IGF-I was given by subcutaneous injection at two doses (150 µg and 450 µg) and the pH 5.4 formulation of IGF-I at two doses (50 µg and 150 µg), such that matching effects on blood glucose and serum IGF-I might be expected. In addition, the rapid absorption of IGF-I was measured by taking samples at very frequent intervals immediately following the injection of the respective IGF-I formulations.

Experimental Design

Four treatment groups of female dw/dw rats, four rats per group, were injected subcutaneously with one of the four solutions of the two IGF-I formulations below:

A. pH 6.0 formulation of IGF-I (5 mg/ml in 10 mM sodium citrate buffer and 126 mM NaCl, pH 6.0):
 1) 150 µg in 100 µl of solution
 2) 450 µg in 100 µl of solution B. pH 5.4 formulation of IGF-I (10 mg/ml in 50 mM sodium acetate buffer, 2.5 mg/ml phenol, 5.84 mg/ml NaCl, and 9 mg/ml benzyl alcohol, pH 5.4):
 3) 50 µg in 100 µl of solution
 4) 150 µg in 100 µl of solution Three blood samples were taken before the injections at −15, −10, and −5 minutes; then samples were taken at 3, 6, 9, 20, 30, 45, 60, 90, and 120 minutes. The experiment was otherwise conducted in an identical manner to Example V.

Results

Figure 19:
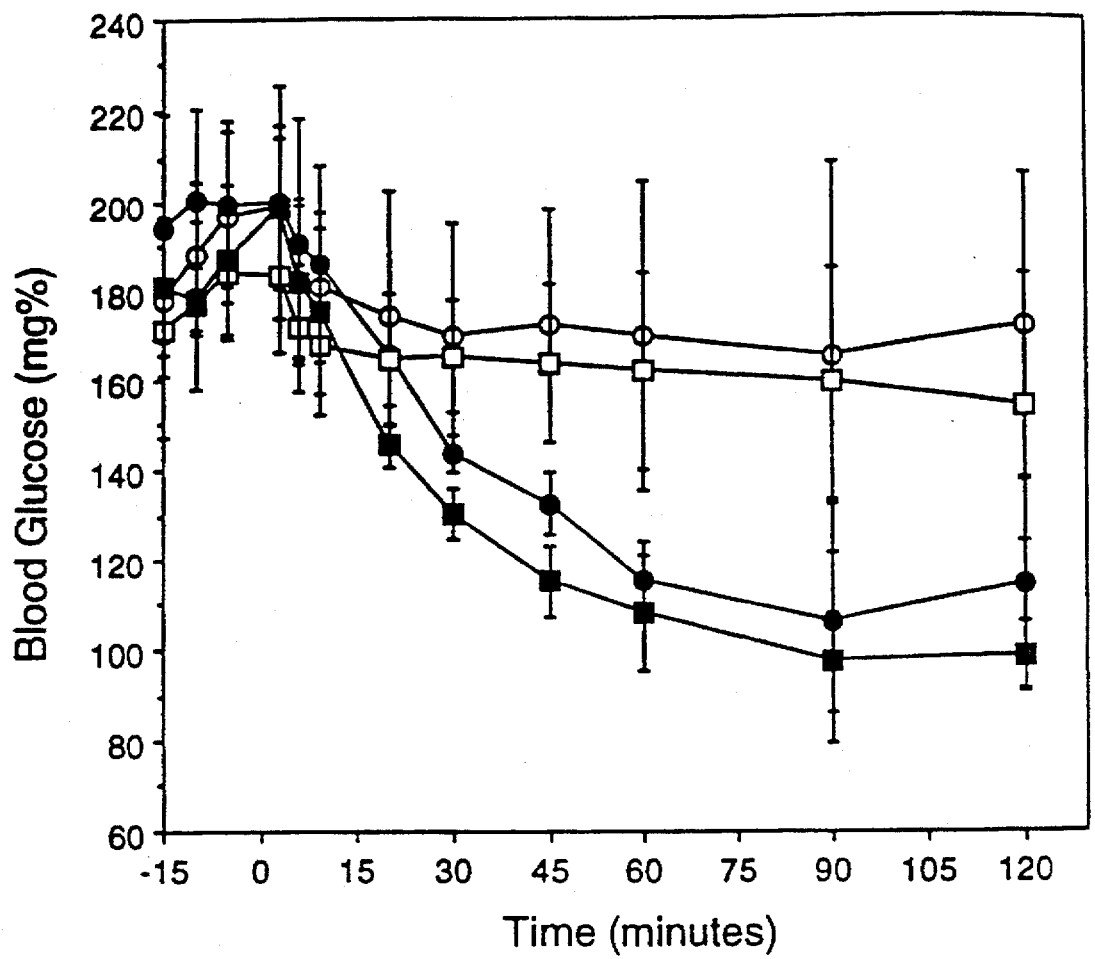
FIG. 19 shows the absolute glucose levels (mg %) when a pH 6.0 citrate IGF-I formulation (circles) was administered subcutaneously in doses of 150 µg (open) and 450 µg (filled) and when a pH 5.4 acetate IGF-I formulation (squares) was administered subcutaneously in doses of 50 µg (open) and 150 µg (filled).
Figure 20:
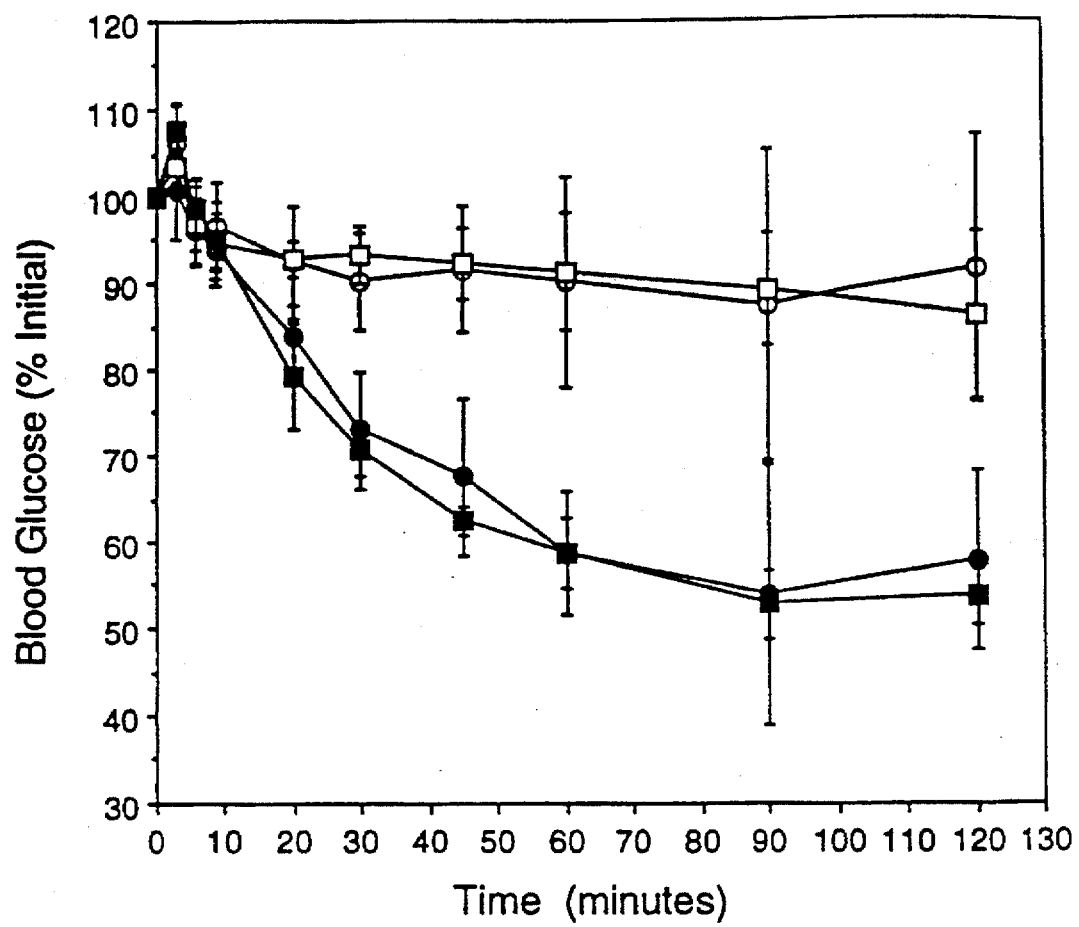
FIG. 20 shows the percent change in blood glucose levels with time using the four different formulations, with the symbols being the same as for FIG. 19.

In this example the absolute (FIG. 19) and the mean percentage (FIG. 20) changes in blood glucose with time after subcutaneous injections of IGF-I given at time zero are shown. There was a clear difference between the blood glucose responses to the two formulations given subcutaneously. At three-fold different doses of IGF-I, equivalent hypoglycemic responses were obtained, as the 150-µg dose of the pH 6.0 formulation and the 50-µg dose of the pH 5.4 formulation were equivalent, as were the 450-µg dose of the pH 6.0 formulation and the 150-µg dose of the pH 5.4 formulation.

Figure 21:
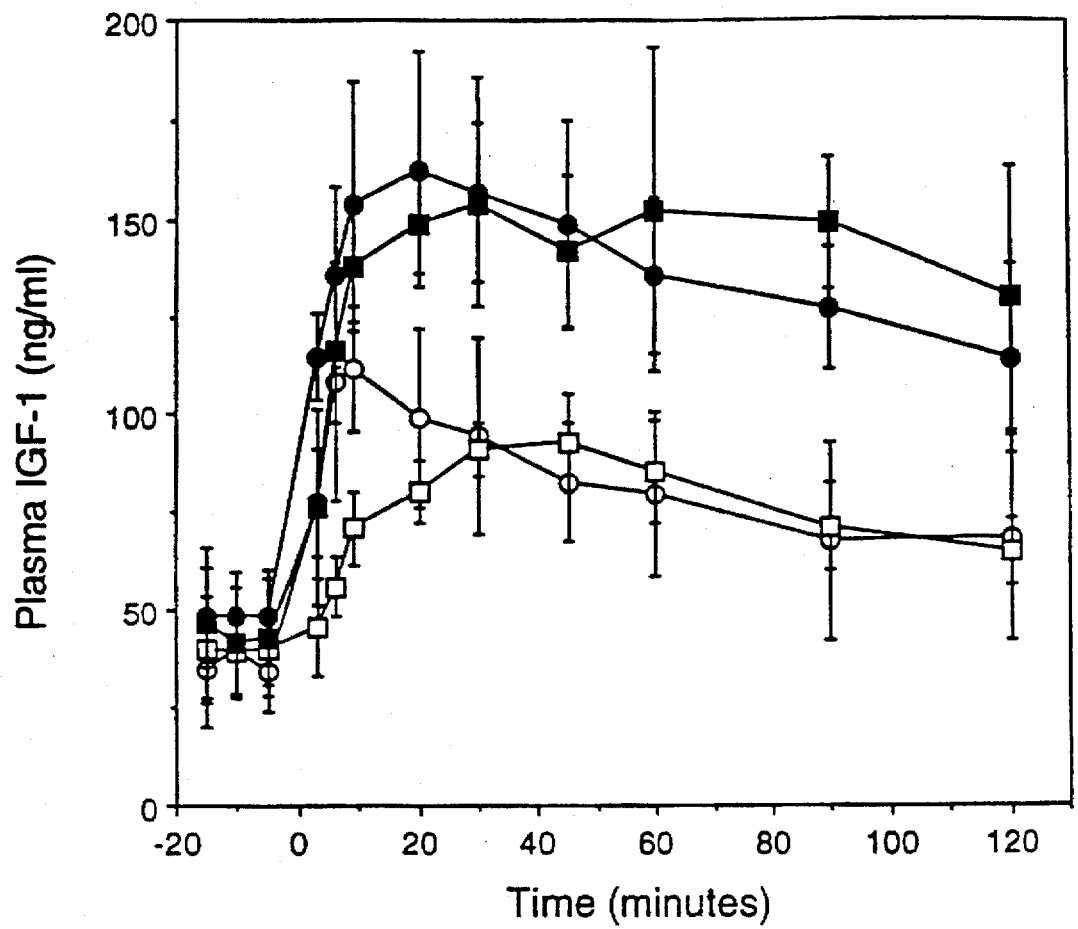
FIG. 21 shows the level of plasma IGF-I (ng/ml) versus time after subcutaneous injection of the four different formulations, with the symbols being the same as for FIG. 19.

FIG. 21 shows the plasma IGF-I concentrations after the subcutaneous injections of IGF-I given at time zero. The pre-injection IGF-I concentrations were not different for the four groups. The IGF-I concentrations achieved were dose related and directly mirrored the blood glucose concentrations. At three-fold different doses of IGF-I, equivalent plasma IGF-I concentrations were obtained for the 150-µg dose of the pH 6.0 formulation and the 50-µg dose of the pH 5.4 formulation and for the 450-µg dose of the pH 6.0 formulation and the 150-µg dose of the pH 5.4 formulation.

In conclusion, following a subcutaneous injection, the absorption and therefore the efficacy of the IGF-I was improved about 3-fold using the pH 5.4 formulation of IGF-I.

EXAMPLE XII

The previous examples established that the re-formulated pH 5.4 IGF-I had an increased potency in terms of a hypoglycemic response when given by subcutaneous injection. In addition, the examples showed that after a subcutaneous injection a three-fold increase in the absorption and efficacy of the IGF-I was measured using the re-formulated pH 5.4 IGF-I.

All these experiments were conducted in the dw/dw rat. It is possible that such rats, which are GH-deficient and IGF-I-deficient compared to a normal GH-sufficient and IGF-I-sufficient rat, might in some way allow IGF-I to be absorbed much better in the pH 5.4 formulation. In the present example, IGF-I was given by subcutaneous injection in a normal rat, and blood glucose and serum IGF-I concentrations were measured. As these normal rats weighed twice as much (230–250 grams) as the dw/dw rats, and might be expected to have higher concentrations of plasma IGF binding proteins, the doses of IGF-I were doubled, compared to those used in the earlier examples in the dw/dw rat.

Experimental Design

Four groups of normal male Sprague-Dawley rats (230–250 g), four rats per group, were dosed subcutaneously with one of the four solutions of the two IGF-I formulations below:

A. pH 6.0 formulation of IGF-I (5 mg/ml in 10 mM sodium citrate buffer and 126 mM NaCl, pH 6.0):

1) 300 μg in 200 μl of solution
2) 900 μg in 200 μl of solution

B. pH 5.4 formulation of IGF-I (10 mg/ml in 50 mM sodium acetate buffer, 2.5 mg/ml phenol, 5.84 mg/ml NaCl, and 9 mg/ml benzyl alcohol, pH 5.4):

3) 100 μg in 200 μl of solution
4) 300 μg in 200 μl of solution

Three blood samples were taken before the injections at −15, −10, and −5 minutes; then samples were taken at 3, 6, 9, 20, 30, 45, 60, and 90 minutes. The experiment was otherwise conducted in an identical manner to Example V.

Results

Figure 22:
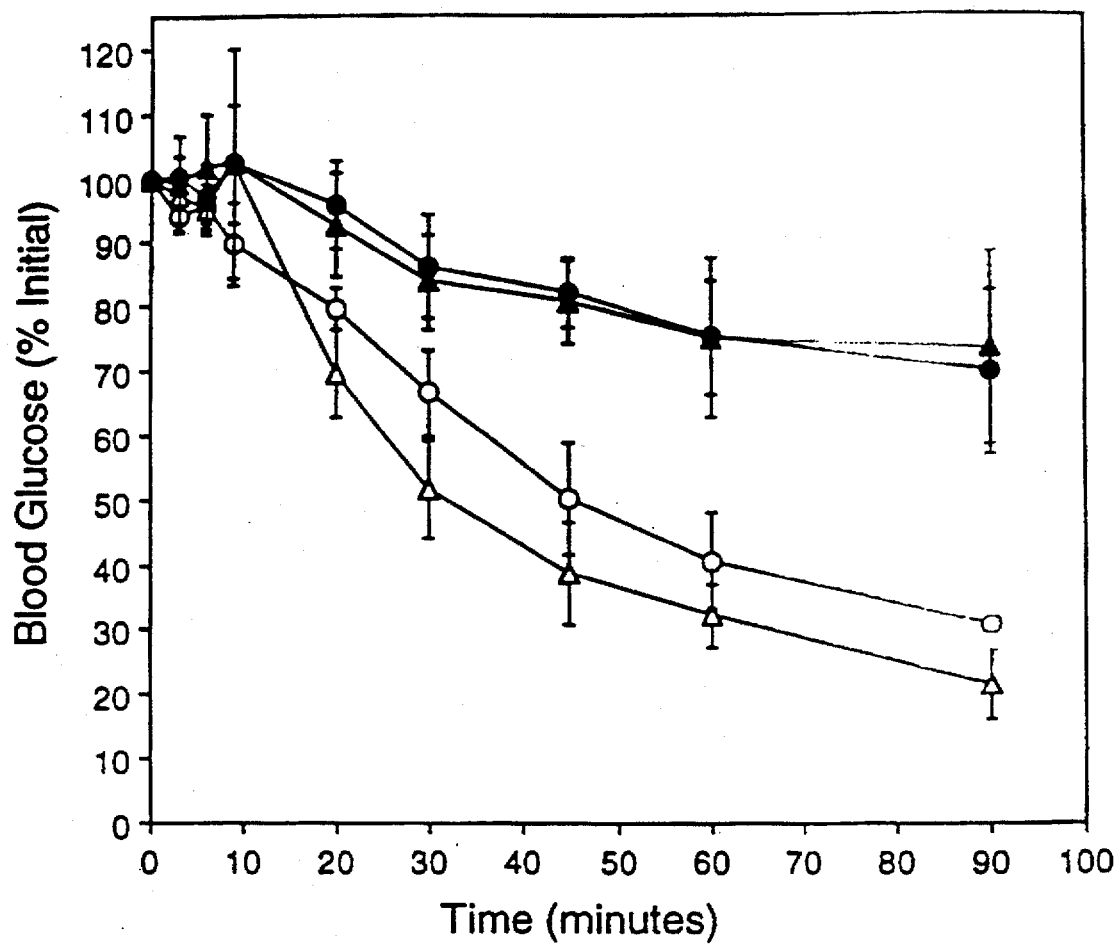
FIG. 22 shows the percent change in blood glucose levels with time in normal rats when a pH 6.0 citrate IGF-I formulation (triangles) was administered subcutaneously in doses of 900 µg (open) and 300 µg (filled) and when a pH 5.4 acetate IGF-I formulation (circles) was administered subcutaneously in doses of 300 µg (open) and 100 µg (filled).

FIG. 22 shows the mean percentage changes in blood glucose with time after a subcutaneous injection of IGF-I given at time zero. There was a clear difference between the blood glucose responses to the two formulations given subcutaneously at the 300 μg dose of IGF-I. The hypoglycemic response induced by 300 μg of the pH 6.0 formulation of IGF-I was nearly identical to that induced by 100 μg of the pH 5.4 formulation of IGF-I. The response to 900 μg of the pH 6.0 formulation was also similar to the response to 300 μg of the pH 5.4 formulation of IGF-I.

Therefore, the pH 5.4 formulation of IGF-I showed improved efficacy compared to the pH 6.0 formulation when injected subcutaneously in a normal rat. Data obtained in GH- and IGF-I-deficient dwarf animals could thus be extrapolated to a GH- and IGF-I-sufficient normal animal.

EXAMPLE XIII

The previous examples established that the re-formulated pH 5.4 IGF-I had an increased potency in terms of a hypoglycemic response when given by subcutaneous injection in normal rats. After a subcutaneous injection a threefold increase in the absorption and efficacy of the IGF-I was measured using the re-formulated pH 5.4 IGF-I.

In these normal male rats weighing 230–250 grams it was established that a dose of 300 μg of IGF-I caused a small reduction in blood glucose when given in the pH 6.0 formulation or a large reduction when given in the pH 5.4 formulation. An object of this example was to develop a formulation in which IGF-I was stable, and which also could be co-mixed with hGH.

In this example, therefore, IGF-I was co-delivered with hGH, and the effect of the hGH and its formulation on the absorption of the IGF-I was studied. The efficacy of the co-mix was tested when given by subcutaneous injection, the usual route of injection for these therapeutic drugs. This example tested the acute hypoglycemic efficacy of the co-mix. In the next example, the long-term anabolic efficacy of the co-mix on body growth was tested.

Experimental Design

Four groups of normal male Sprague-Dawley rats (230–250 g), four rats per group, were dosed subcutaneously with one of the four IGF-I or IGF-I/GH formulations below:

A. pH 6.0 formulation of IGF-I (5 mg/ml in 10 mM sodium citrate buffer and 126 mM NaCl, pH 6.0):

1) 300 μg IGF-I in 200 μl of solution

B. pH 5.4 formulation of IGF-I (10 mg/ml in 50 mM sodium acetate buffer, 2.5 mg/ml phenol, 5.84 mg/ml NaCl, and 9 mg/ml benzyl alcohol, pH 5.4) and/or pH 6.0 formulation of hGH (5 mg/ml in 10 mM sodium citrate buffer, 2.5 mg/ml phenol, 8.77 mg/ml NaCl, and 2.0 mg/ml polysorbate 20, pH 6.0):

2) 300 μg IGF-I in 200 μl of solution
3) 300 μg IGF-I+100 μg hGH in 200 μl of solution
4) 300 μg IGF-I+10 μg hGH in 200 μl of solution Three blood samples were taken before the injections at −15, −10, and −5 minutes; then samples were taken at 3, 6, 9, 20, 30, 45, 60, 90, and 120 minutes. The experiment was otherwise conducted in an identical manner to Example V.

Results

Figure 23:
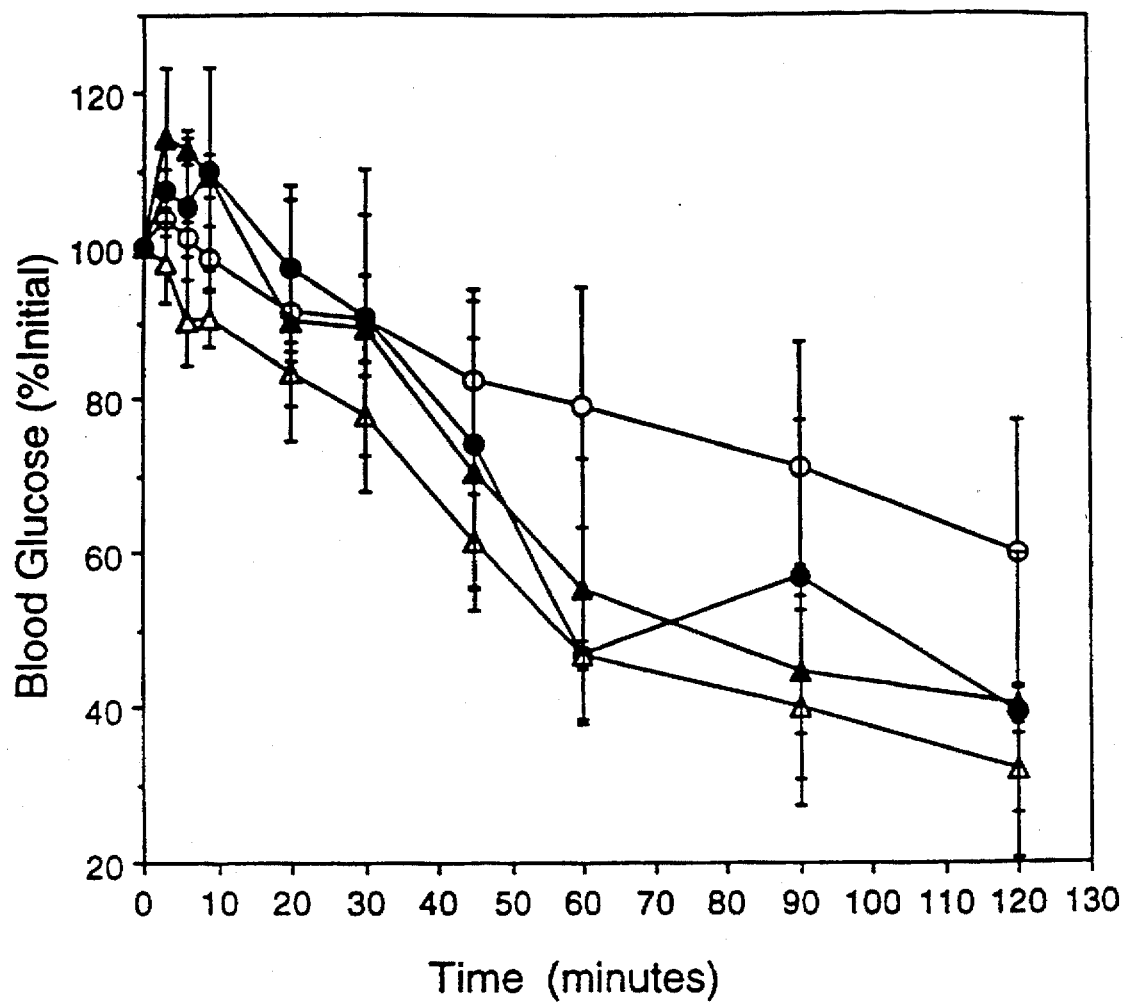
FIG. 23 shows the percent change in blood glucose levels with time in normal rats when a pH 6.0 citrate IGF-I formulation (open circles) was administered subcutaneously in a dose of 300 µg, when a pH 5.4 acetate IGF-I formulation (filled circles) was administered subcutaneously in a dose of 300 µg, and when a pH 5.4 acetate IGF-I and GH co-mixed formulation (triangles) was administered subcutaneously in doses of 100 µg (open) and 10 µg (filled) of hGH and 300 µg IGF-I.

FIG. 23 shows the mean percentage changes in blood glucose with time after a subcutaneous injection of IGF-I given at time zero. There was a small reduction in blood glucose when the pH 6.0 formulation was given but a much larger fall when the pH 5.4 formulation was given. The hypoglycemia induced by the co-mixes of hGH and IGF-I formulation was similar to that induced by the pH 5.4 IGF-I formulation alone. At the 60-minute timepoint all three groups receiving the pH 5.4 formulation had significantly lower blood glucose levels than the group that received the pH 6.0 formulation of IGF-I.

Figure 24:
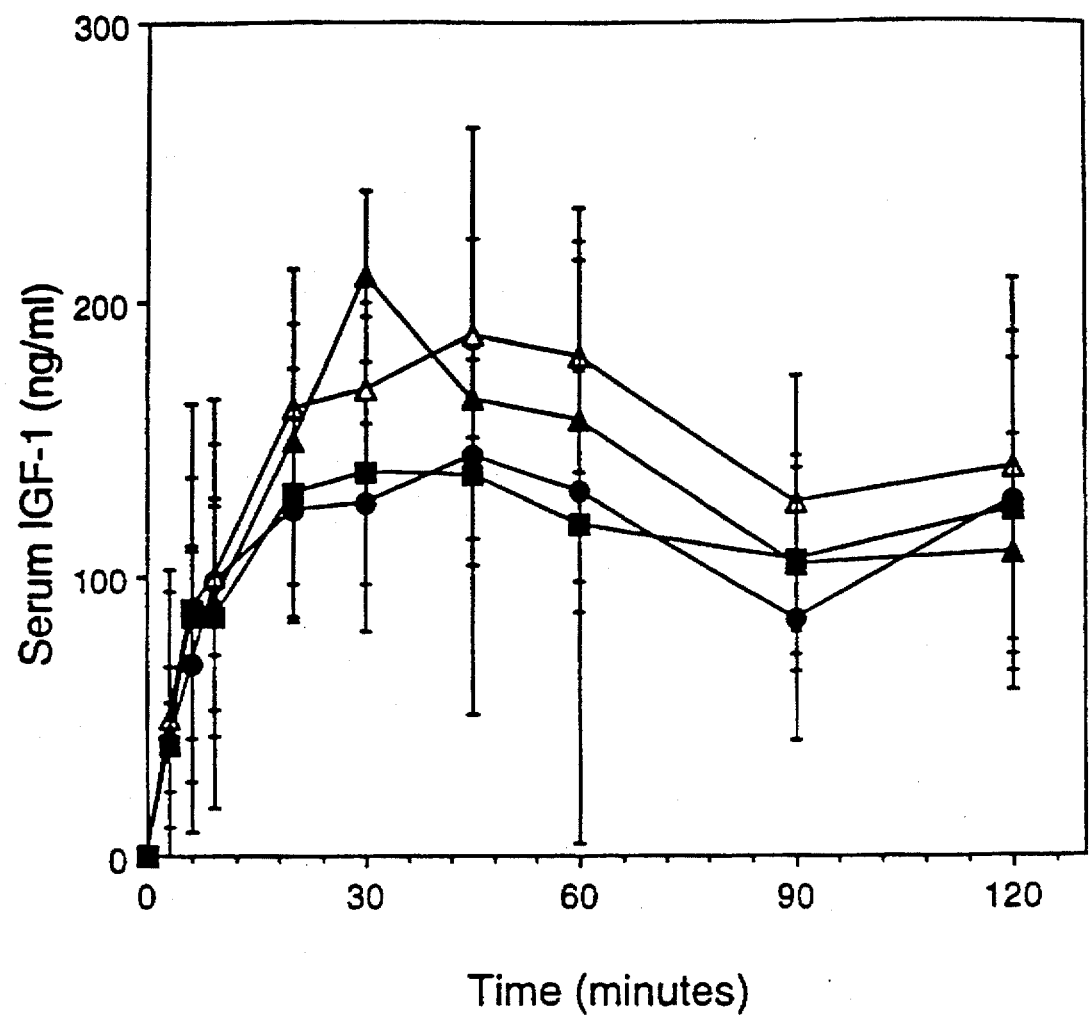
FIG. 24 shows the level of plasma IGF-I (ng/ml) versus time after subcutaneous injection of the four different formulations, with the symbols being the same as for FIG. 22 for the comix, and with the filled circles being the pH 6.0 IGF-I formulation and the filled squares being the pH 5.4 IGF-I formulation alone.

FIG. 24 shows the plasma IGF-I concentrations after the subcutaneous injections of IGF-I given at time zero. The pre-injection IGF-I concentrations were not different for the four groups. The IGF-I concentrations tended to mirror the blood glucose concentrations, with the pH 6.0 formulation of IGF-I tending to be more poorly absorbed compared to the pH 5.4 IGF-I formulation. The co-mix of hGH and IGF-I led to similar blood IGF-I concentrations to that of the pH 5.4 IGF-I formulation alone.

Changing the formulation to one that was mixable with hGH led to the best IGF-I formulation in terms of hypoglycemic activity and IGF-I absorption, even when co-mixed with hGH.

EXAMPLE XIV

The previous examples have shown that the re-formulated pH 5–5.5 IGF-I formulations enhance the absorption and bioactivity of IGF-I. In addition, these re-formulations of IGF-I can be co-mixed with hGH while maintaining IGF-I absorption. In this example, the anabolic activity of the co-mixed combination is studied using two doses of hGH and a fixed dose of IGF-I.

In Examples I and II it was established that subcutaneous injections of hGH and infusions of IGF-I gave additive growth responses in the rat. Now it was desired to known if the co-formulation of IGF-I and hGH could be delivered to an animal with the additive anabolic effects of IGF-I and hGH being retained. The options were to deliver the mixture either as an injection (as with hGH) or as an infusion (as with IGF-I).

First, the co-formulation could be delivered as a co-mix by injection. It was shown in Examples I and II that infused IGF-I and injected GH had an additive effect. Since it was found that infused GH did not have such an effect with IGF-I, injections were the obvious method of delivering the hGH. However, IGF-I had been given by infusion in these examples to show additive effects. It had not been shown that the pH 6.0 IGF-I formulation given by injection was efficacious in terms of inducing an additive anabolic response with co-injected hGH.

Nevertheless, when it was attempted to induce growth responses in GH-deficient rats by delivering the pH 6.0 formulation alone by injection, it was found that IGF-I injections were very poor at inducing an anabolic effect, but very effective at inducing a hypoglycemic response. U.S. Pat. No. 5,187,151. The poor anabolic effect of IGF-I injections had also been shown in the mouse. Woodall et al., *Horm. Metab. Res.*, 23: 581–584 (1991). Four daily injections of IGF-I (two daily injections had marginal effects) were needed to induce anabolic effects approaching those seen with IGF-I infusions.

Therefore, it was unclear whether the improved glycemic potency of injections of the pH 5.4 formulation of IGF-I also would be translated into an improved anabolic efficacy of injections of IGF-I. In this example, hGH and IGF-I were co-injected twice daily to determine the results.

Methods

1. Compounds

All solutions of IGF-I and GH alone or together were prepared on day 0 so that sufficient drug was made for the entire example and stored at 4° C. during the seven-day experiment. The separate hGH and IGF-I formulations employed were the pH 5.4 IGF-I formulation and the pH 6.0 hGH formulation described in Example XIII.

2. Animals

Sixty female dw/dw rats of 60–70 days of age were obtained from Simonsen (Gilroy, Calif.). They were group housed in a room with controlled lighting and temperature and fed a grain diet and water ad libitum. They were weighed twice and the largest and the smallest animals were discarded to leave 48 rats ranging in body weight from 105 to 135 grams at their first injection.

3. Experimental Design

The rats were randomly assigned to six groups of eight rats per group based on their body weight, so that the average weight per group (119 g) was not different.

The six treatment groups were:

1) two excipient injections/day
2) pH 5.4 IGF-I formulation alone, 300 µg twice daily= 600 µg/day
3) pH 6.0 hGH formulation alone, 15 µg twice daily=30 µg/day
4) pH 6.0 hGH formulation alone, 60 µg twice daily=120 µg/day
5) co-mix of pH 5.4 IGF-I formulation, 300 µg twice daily, plus pH 6.0 hGH formulation, 15 µg twice daily
6) co-mix of pH 5.4 IGF-I formulation, 300 µg twice daily, plus pH 6.0 hGH formulation, 60 µg twice daily 100-µl injections of each formulation were given subcutaneously in the nape of the neck twice daily either at the time the animals were weighed (8–9AM) or in the late afternoon (4–5PM).

The last injection was a PM injection, with all the animals being sacrificed approximately 18 hours later. At sacrifice, a large blood sample was taken, and the liver, heart, spleen, thymus, and kidneys were dissected and weighed. Serum was assayed for IGF-I after extraction with acid-ethanol and a subsequent conventional RIA for IGF-I.

All data shown are Mean±SD with eight rats per group. Treatment groups were compared by ANOVA and then by Duncan's Multiple Range Test.

Results

1. Body Weight Gain

The dose of IGF-I (300 µg/injection) was chosen as a near maximally effective hypoglycemic dose of IGF-I (based on the earlier examples) when given in the pH 5.4 formulation. These earlier examples used only one dose, so it was uncertain if a second or third dose would be more or less effective at inducing hypoglycemia. However, it was assumed that the 300 µg/injection dose would be nearly maximal as a hypoglycemic dose when given repeatedly, and that it also would be nearly maximal as an anabolic dose. The doses of hGH were based on effective doses established in other experiments of twice daily hGH dosing in the dw/dw rat.

In addition, the doses of hGH and of IGF-I were chosen to attempt to obtain growth responses similar to those found with daily hGH dosing in the dw/dw rat in Example II. Finally, the doses were also chosen to give a broad range of the hGH to IGF-I weight ratio (1:5 to 1:20) in the range where the hGH and IGF-I in the co-mix were shown to be chemically stable.

A comparison of the results in the present example with the results in Example II show that comparable effects of IGF-I and hGH were found with the dosing regimes chosen.

Figure 25:
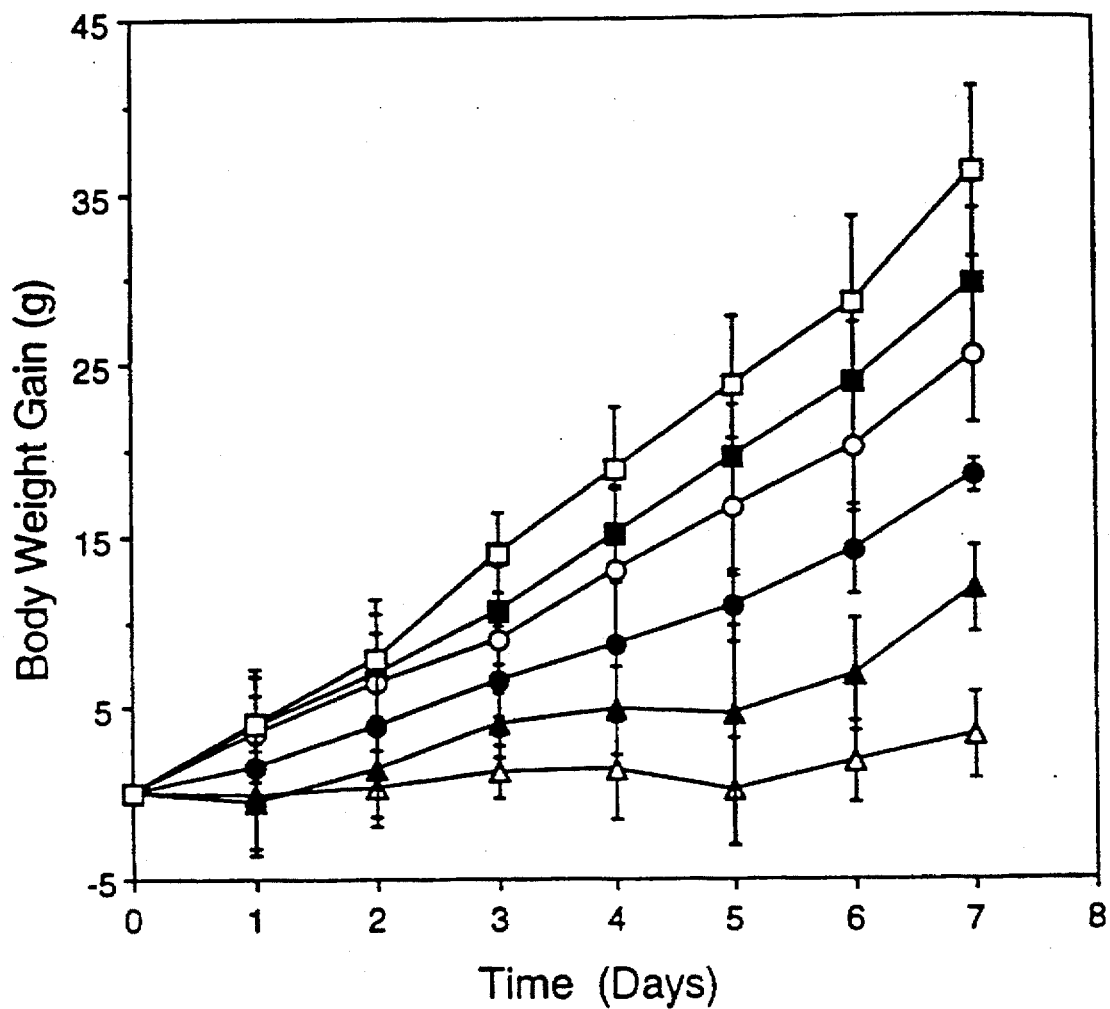
FIG. 25 shows the body weight gain (g) in dw/dw rats administered by subcutaneous injection excipient (open triangles), IGF-I at a dose of 600 µg (filled triangles), rhGH at a dose of 30 µg (filled circles), rhGH at a dose of 120 µg (filled squares), IGF-I+hGH at doses of 600 µg and 30 µg IGF-I and hGH, respectively (open circles), and IGF-I +hGH at doses of 600 µg and 120 µg IGF-I and hGH, respectively (open squares).

The animals appeared to tolerate the repeated injections of IGF-I with no overt signs of hypoglycemia. The anabolic or growth-promoting activity of hGH and IGF-I was gauged primarily by measuring the weight gain in the rats. FIG. 25 and Table 2 show the weight gains of the dw/dw rats over the seven-day study. The control excipient-injected rats showed a very small weight gain (3.4±2.5 g over the 7-day study). In other words, their growth reflected the GH- and IGF-deficient state expected of dwarf rats.

Twice daily IGF-I injections induced a surprisingly large, and statistically significant ($p<0.001$), amount of body weight gain (11.9±2.5 g). These data are very similar to the data in FIG. 14, where 240 µg/day of rhIGF-I was infused for seven days in dw/dw rats and resulted in a weight gain of 12.15±3.75 g.

The two doses of rhGH both induced significant ($p<0.001$) weight gain (18.5±2.9 and 29.6±4.4 g for the 30 and 120 µg/day doses, respectively). The weight gain in Example II in the dw/dw rat with 200 µg/day of hGH given once daily was 19.9±4.5 g, which was similar to the response to 30 µg/day of hGH in the present example.

There was an additive effect of the co-mixed IGF-I and hGH treatments. Thus, the weight gains for the co-mixed formulations of hGH and IGF-I were 25.4±3.9 and 36.1±4.9 g, for 30 and 120 µg hGH/day groups, respectively, compared to the 18.5±2.9 and 29.6±4.4 g gains for these doses given alone. The comparison of hGH alone to hGH+IGF-I was statistically significant ($p<0.01$) for both hGH doses.

In Example II, the weight gain with the 200 µg/day dose of hGH injected once daily along with an IGF-I infusion was 28.4±6.0 g, again similar to the response to the 30 µg/day dosing of the hGH+IGF-I formulation in the present example. These data therefore indicate that with equivalent growth responses induced by hGH injection (whether given once or twice a day) the co-administration of IGF-I gives an additive growth response, irrespective of whether the IGF-I is given by infusion or by injection.

TABLE 2

Dw/dw rats treated with IGF-I + hGH; twice daily injection

| Group | Wt Gain (g) | Serum IGF-I (ng/ml) | Kidney Wt (% Bwt) | Thymus Wt (% Bwt) | Spleen Wt (% Bwt) |
|---|---|---|---|---|---|
| Excipient | 3.4 ± 2.5 | 129 ± 49 | 0.86 ± .10 | 0.16 ± .02 | 0.23 ± .02 |
| IGF-I (600 µg) | 11.9 ± 2.5* | 140 ± 42 | 0.83 ± .05 | 0.17 ± .03 | 0.25 ± .02 |
| hGH (30 µg) | 18.5 ± 2.9* | 163 ± 47 | 0.81 ± .07 | 0.17 ± .04 | 0.25 ± .02 |
| hGH (120 µg) | 29.6 ± 4.4* | 189 ± 50* | 0.84 ± .10 | 0.18 ± .03 | 0.27 ± .03* |

TABLE 2-continued

Dw/dw rats treated with IGF-I + hGH; twice daily injection

| Group | Wt Gain (g) | Serum IGF-I (ng/ml) | Kidney Wt (% Bwt) | Thymus Wt (% Bwt) | Spleen Wt (% Bwt) |
|---|---|---|---|---|---|
| IGF-I (600 µg) + hGH (30 µg) | 25.4 ± 3.9* | 120 ± 29 | 0.77 ± .04 | 0.16 ± .04 | 0.27 ± .02* |
| IGF-I (600 µg) + hGH (120 µg) | 36.1 ± 4.9* | 152 ± 41 | 0.77 ± .05 | 0.17 ± .03 | 0.31 ± .04* |

Wt = weight
Bwt = body weight
* = statistically significant
(n = 8, p < 0.05 vs Excipient)

2. Serum IGF-I Concentrations

The serum samples obtained at sacrifice 18 hours after the last injection were extracted and IGF-I was measured (Table 2). There was a small but statistically significant rise in IGF-I after the injection of hGH at the high dose. However, there was no maintained rise in serum IGF-I after the injection of IGF-I or after the injection of the co-mix, since IGF-I when given by injection is quite rapidly cleared in the rat. Sampling at times closer to the time of injection would be expected to show the higher blood IGF-I concentrations seen in the earlier examples. The greater efficacy of the co-mix therefore could not be directly tied to a higher serum concentration of IGF-I.

3. Organ Growth

The data in Table 2 for the growth of the different body organs gave surprising results. In animals infused with IGF-I clear overgrowth of the spleen, thymus, and kidney has been shown in many studies, in hypophysectomized, dwarf, and normal animals. For example, see the data in Examples I and II above. However, in the present example, injections of IGF-I at doses that induced additive anabolic effects with hGH on whole body growth gave surprisingly little organ overgrowth. These data are quite different from the data with IGF-I infusions in the earlier examples.

For instance, with IGF-I infusions in dw/dw rats in Example II, the relative size of the kidney increased significantly as a percent of body weight from 0.79±0.05 in excipient-treated controls to 1.0±0.09 in IGF-I-treated rats. However, in the present example (Table 2) when IGF-I was given by injection, with or without hGH, there was a tendency for the relative size of the kidney to show, in fact, a reduction from 0.86±0.10 in excipient-treated controls to 0.83±0.05 in IGF-I-treated rats.

In Example II the thymus showed a vigorous growth response to IGF-I infusions, increasing well out of proportion to the rest of the body its relative size as a percent of body weight from 0.14±0.04 in excipient-treated controls to 0.18±0.09 in IGF-I-treated rats. However, in the present Example (Table 2) IGF-I injections had no significant effect on relative thymus weight whether IGF-I was given alone or with hGH.

The relative size of the spleen did show a significant increase with IGF-I treatment, but only when given along with high-dose hGH treatment. In comparison, in Example II the relative size of the spleen increased dramatically as a percent of body weight from 0.23±0.01 in excipient-treated controls to 0.47±0.12 in rats treated with IGF-I alone. In the present example, when IGF-I injections were given alone there was no significant effect on absolute or relative spleen size, yet there was a clear effect of IGF-I increasing spleen size when the IGF-I was given along with the hGH. This evidence suggests that the IGF-I injections in some way synergized with the hGH to induce spleen growth.

This relative lack of an effect of the IGF-I injections on the growth of the different tissues, compared to the effect of IGF-I infusions, made the additive whole body effect of hGH and IGF-I even more surprising. Without being limited to any one theory, it appears that injections and infusions of IGF-I cause a different spectrum of growth responses in different tissues. All the tissues measured seemed to respond to the IGF-I injections with a growth response more like that of GH in that they grew in proportion to the increase in whole body size. In the earlier examples, it might have been reasoned that GH and IGF-I might synergize to cause a whole body anabolic response because they caused selective and differential organ growth. However, when the IGF-I is given by injection there is much less evidence of selective or differential organ growth. It was surprising that the overgrowth of some organs was lost when IGF-I was injected, yet when hGH was added to the formulation to be injected, the additive whole body anabolic activity was retained.

Conclusion

Injections of the pH 5.4 formulation of IGF-I induced a very significant whole body growth response with little organ overgrowth. In addition, when the IGF-I was co-injected with GH there was an additive anabolic or growth-promoting effect very similar to that seen previously with IGF-I infusions.

What is claimed is:

1. An IGF-I-containing composition for subcutaneous administration comprising about 8–12 mg/ml of IGF-I, about 5–6 mg/ml of sodium chloride, a stabilizer consisting of about 8–10 mg/ml of benzyl alcohol or about 2–3 mg/ml of phenol, or both about 8–10 mg/ml of benzyl alcohol and about 2–3 mg/ml of phenol, and an about 50 mM sodium acetate buffered solution at a pH of about 5.4.

2. The composition of claim 1 additionally comprising about 1–5 mg/ml of a surfactant.

3. The composition of claim 2 wherein the surfactant is polysorbate or poloxamer in an amount of about 1–3 mg/ml.

4. The composition of claim 3 wherein the surfactant is polysorbate.

5. A method for treating diabetes comprising administering subcutaneously to a mammal having diabetes an amount of the composition of claim 1 effective to treat diabetes.

6. A method for treating diabetes comprising administering subcutaneously to a mammal having diabetes an amount of the composition of claim 2 effective to treat diabetes.

7. A method for treating diabetes comprising administering subcutaneously to a mammal having diabetes an amount of the composition of claim 3 effective to treat diabetes.

8. A method for treating diabetes comprising administering subcutaneously to a mammal having diabetes an amount of the composition of claim 4 effective to treat diabetes.

* * * * *